United States Patent [19]
Matsui et al.

[11] Patent Number: 6,030,545
[45] Date of Patent: *Feb. 29, 2000

[54] TERCYCLOHEXANE, LIQUID-CRYSTALLINE COMPOUND AND LIQUID CRYSTAL COMPOSITION COMPRISING SAME

[75] Inventors: Shuichi Matsui; Kazutoshi Miyazawa; Takashi Kato; Yasuko Sekiguchi; Etsuo Nakagawa, all of Chiba, Japan

[73] Assignee: Chisso Corporation, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/663,925

[22] Filed: Jun. 14, 1996

[30] Foreign Application Priority Data

Jun. 16, 1995 [JP] Japan ................................... 7-174089

[51] Int. Cl.$^7$ ............................ C09K 19/30; C07C 22/00
[52] U.S. Cl. ....................................... 252/229.63; 570/144
[58] Field of Search ........................ 252/299.63; 570/144

[56] References Cited

U.S. PATENT DOCUMENTS

| | | | |
|---|---|---|---|
| 4,534,883 | 8/1985 | Sugimori et al. | 252/299.63 |
| 4,606,845 | 8/1986 | Romer et al. | 252/299.63 |
| 4,663,073 | 5/1987 | Sucrow et al. | 252/299.63 |
| 4,719,032 | 1/1988 | Wachtler et al. | 252/299.63 |
| 4,724,097 | 2/1988 | Romer et al. | 252/299.63 |
| 4,871,470 | 10/1989 | Wachtler et al. | 252/299.63 |
| 4,877,547 | 10/1989 | Weber et al. | 252/299.61 |
| 5,030,383 | 7/1991 | Scheuble et al. | 252/299.61 |
| 5,308,537 | 5/1994 | Coates et al. | 252/299.6 |

Primary Examiner—C. H. Kelly
Attorney, Agent, or Firm—Wenderoth, Lind & Ponack, L.L.P.

[57] ABSTRACT

The present invention provides a liquid-crystalline compound which has a reduced viscosity, a wide liquid crystal temperature range (high clearing point), a high chemical stability (extremely high specific resistance, high voltage holding ratio) and a high solubility with other liquid-crystalline compound(s) and preferably has a proper refractive index anisotropy. The present invention also provides a liquid crystal composition having excellent properties. The liquid-crystalline compound is represented by the following general formula (1):

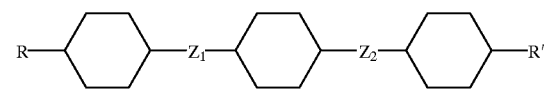

(1)

wherein R and R' each independently represents a $C_{1-20}$ alkyl or halogenated alkyl group or a group obtained by replacing one or more —$CH_2$— groups in the alkyl group by any of —O—, —S—, —CH=CH— or —C≡C—, provided that two or more —$CH_2$— groups are not consecutively replaced by either —O— or —S—; and $Z_1$ and $Z_2$ each independently represents a covalent bond or 1,2-ethylene group, provided that when both $Z_1$ and $Z_2$ are a covalent bond, R and R' are not straight-chain alkyl groups each having the same chain length.

19 Claims, No Drawings

TERCYCLOHEXANE, LIQUID-CRYSTALLINE COMPOUND AND LIQUID CRYSTAL COMPOSITION COMPRISING SAME

FIELD OF THE INVENTION

The present invention relates-to a liquid-crystalline compound. More particularly, the present invention relates to a novel liquid-crystalline compound having three cyclohexane rings in the molecule, a liquid crystal composition comprising such a novel liquid-crystalline compound and to a liquid crystal display element comprising such a liquid crystal composition.

BACKGROUND OF THE INVENTION

A liquid crystal display element is incorporated in watches, electric calculators, various measuring instruments, automobile panels, word processors, electronic notes, printers, computers, televisions, etc. The liquid crystal display element utilizes the optical anisotropy and dielectric anisotropy inherent to a liquid-crystalline compound. Examples of known displaying methods include dynamic scattering system (DS type), guest host type system (GH type), twisted nematic type system (TN type), supertwisted nematic type system (STN type), thin film transistor type system (TFT type) and ferroelectric liquid crystal (FLC). Examples of known means for driving these liquid crystal display elements include static driving system, time-division driving system, active matrix driving system and two-frequency driving system.

Among these known liquid crystal displaying systems, STN system and TFT system are most popular because they have the best display properties.

Liquid crystalline compounds for use in STN system and TFT system must meet various requirements. Particularly important among these requirements are the following five requirements:

(1) It has a low viscosity;
(2) It has a wide temperature range within which it assumes a liquid crystal phase, particularly a high clearing point, or causes no reduction of the nematic phase temperature range when incorporated in a liquid crystal composition;
(3) It is stable to external factors such as heat and light;
(4) It has a good solubility with other liquid-crystalline compounds; and
(5) It has an appropriate refractive index anisotropy.

In particular, viscosity is an extremely important factor governing the response speed of a liquid crystal molecule oriented in a liquid crystal panel to an electric field as described in Phys. Lett., 39A, 69 (1972). A liquid crystal composition which can quickly respond to an electric field exhibits a high display quality and is now most desirable.

To provide a liquid crystal composition which can be used in various operating environments, it is necessary that a liquid crystal composition which assumes a liquid crystal phase in a wide liquid crystal temperature range be prepared. In particular, in order to allow the use under high temperature conditions, a liquid crystal composition having a highest allowable temperature of liquid crystal phase, i.e., high clearing point is required.

In order to provide a liquid crystal composition having a high clearing point, a liquid-crystalline compound having a high clearing point is required as a constituent.

Further, a liquid-crystalline compound to be incorporated in a liquid crystal composition, particularly for TFT, is required to be stable to external environmental factors such as moisture, air, heat and light.

In particular, an active matrix liquid crystal display is suitable for advanced data display for televisions or computers and advanced data display inside automobiles and airplanes. However, in the case where a liquid-crystalline compound or liquid crystal composition which does not possess an extremely high specific resistance (high voltage holding ratio) and a good ultraviolet stability is used, as the electric resistance in the liquid crystal panel falls, the contrast falls, thereby causing a problem in the "erasure of afterimage". The high electric resistance of a liquid crystal composition is an extremely important factor governing the life of the liquid crystal composition particularly when it is driven at a low voltage. Therefore, the extremely high specific resistance (high voltage holding ratio) and good ultraviolet stability are extremely important requirements of the liquid-crystalline compound used.

Further, the liquid-crystalline composition is made of, from a few kinds of to twenty or more kinds of, liquid-crystalline compounds to exhibit optimum properties required for individual elements. Accordingly, the liquid-crystalline compound must exhibit a good solubility with other liquid crystal compound(s), particularly at low temperatures under the recent necessity of use in various conditions.

In other words, in order to allow the use within a wide temperature range, particularly at low temperatures, the liquid crystal composition is required to have a nematic phase even at low temperatures. Therefore, the liquid-crystalline compound to be used essentially must exhibit a high solubility with other liquid crystal compound(s) at low temperatures.

In order to realize the high response, it is preferred that a liquid crystal composition having not only a low viscosity, but also a high refractive index anisotropy be used. The thickness of a cell can be reduced by using such a liquid crystal composition having a high refractive index anisotropy while the product of the cell thickness and the refractive index anisotropy value are kept constant. This makes it possible to prepare a liquid crystal display element which can quickly respond while keeping a high display quality.

In order to obtain a liquid crystal composition having a high refractive index anisotropy, of course, a liquid-crystalline compound having a high refractive index anisotropy is required.

In order to realize a liquid crystal composition having better properties, particularly liquid crystal composition for STN and TFT, it has been keenly desired to provide a liquid-crystalline compound which has a reduced viscosity, a wide liquid crystal temperature range (high clearing point), a high chemical stability (extremely high specific resistance, high voltage holding ratio) and a high solubility with other liquid-crystal compound(s) and preferably has a proper refractive index anisotropy.

SUMMARY OF THE INVENTION

It is therefore an object of the present invention to provide a liquid-crystalline compound which has a reduced viscosity, a wide liquid crystal temperature range (high clearing point), a high chemical stability (extremely high specific resistance, high voltage holding ratio) and a high solubility with other liquid-crystal compound(s) and preferably has a proper refractive index anisotropy.

The inventors made extensive studies to solve the above described problems. As a result, the inventors have found a liquid crystalline compound having a novel structure which exhibits improved properties as compared with known liquid-crystalline compounds.

A first embodiment of the present invention is a liquid-crystalline compound represented by the following general formula (1):

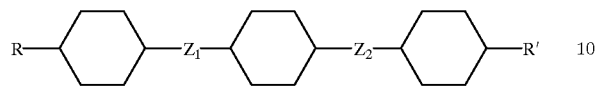

(1)

wherein R and R' each independently represents a $C_{1-20}$ alkyl or halogenated alkyl group or a group obtained by replacing one or more —$CH_2$— groups in the alkyl group by any of —O—, —S—, —CH=CH— or —C≡C—, provided that two or more —$CH_2$— groups are not consecutively replaced by either —O— or —S—; and $Z_1$ and $Z_2$ each independently represents a covalent bond or 1,2-ethylene group, provided that when both $Z_1$ and $Z_2$ are a covalent bond, R and R' are not straight-chain alkyl groups each having the same chain length.

A second embodiment of the present invention is a liquid-crystalline compound according to the first embodiment, wherein R and R' are independently an alkyl group or a group obtained by replacing one or more —$CH_2$— groups in the alkyl group by any of —O—, —S—, —CH=CH— or —C≡C—, provided that two or more —$CH_2$— groups are not consecutively replaced by either —O— or —S—.

A third embodiment of the present invention is a liquid-crystalline compound according to the first embodiment, wherein R and R' are independently an alkyl group or halogenated alkyl group.

A fourth embodiment of the present invention is a liquid-crystalline compound according to the first embodiment of the present invention, wherein at least one of R and R' is a halogenated alkyl group.

A fifth embodiment of the present invention is a liquid-crystalline compound according to the first embodiment of the present invention, wherein both R and R' are a halogenated alkyl group.

A sixth embodiment of the present invention is a liquid crystal composition, comprising at least one liquid-crystalline compound according to any one of the first to fifth embodiments of the present invention.

A seventh embodiment of the present invention is a liquid crystal composition, comprising as a first component at least one liquid-crystalline compound according to any one of the first to fifth embodiments of the present invention and as a second component at least one compound selected from the group consisting of compounds represented by the following general formulae (2), (3) and (4):

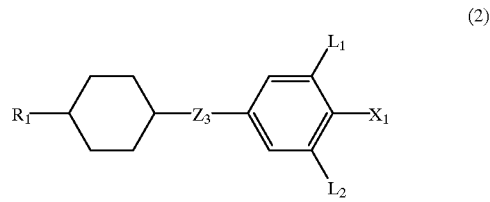

(2)

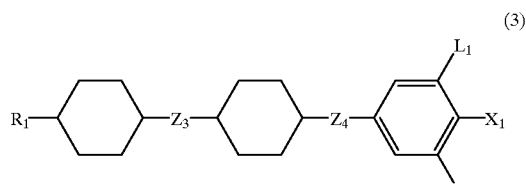

(3)

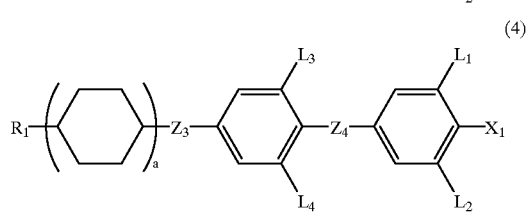

(4)

wherein $R_1$ represents a $C_{1-10}$ alkyl group; $X_1$ represents —F, —Cl, —$OCF_3$, —$OCF_2H$, —$CF_3$, —$CF_2H$ or —$CFH_2$; $L_1$, $L_2$, $L_3$ and $L_4$ each independently represents —H or —F; $Z_3$ and $Z_4$ each independently represents —$(CH_2)_2$—, —CH=CH— or a covalent bond; and a represents an integer of from 1 or 2.

An eighth embodiment of the present invention is a liquid crystal composition, comprising as a first component at least one liquid-crystalline compound according to any one of the first to fifth embodiments of the present invention and as a second component at least one compound selected from the group consisting of compounds represented by the following general formulae (5), (6), (7), (8) and (9):

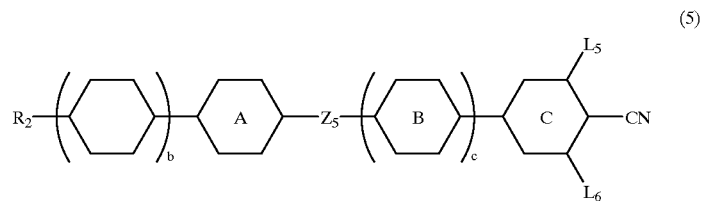

(5)

wherein $R_2$ represents —F, a $C_{1-10}$ alkyl group, a $C_{2-10}$ alkenyl group or a group obtained by replacing one or more methylene groups (—$CH_2$—) in the alkyl or alkenyl group by an oxygen atom (—O—), provided that two or more methylene groups are not consecutively replaced by an oxygen atom; the ring A represents trans-1,4-cyclohexylene group, 1,4-phenylene group or 1,3-dioxane-2,5-diyl group; the ring B represents trans-1,4-cyclohexylene group, 1,4-phenylene group or pyrimidine-2,5-diyl group; the ring C represents trans-1,4-cyclohexylene group or 1,4-phenylene group; $Z_5$ represents —$(CH_2)_2$—, —COO— or a covalent bond; $L_5$ and $L_6$ each independently represents —H or —F; and b and c each independently represents an integer of 0 or 1;

(6)

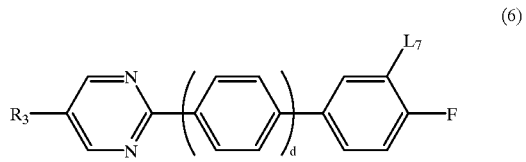

wherein $R_3$ represents a $C_{1-10}$ alkyl group; $L_7$ represents —H or —F; and d represents an integer of 0 or 1;

(7)

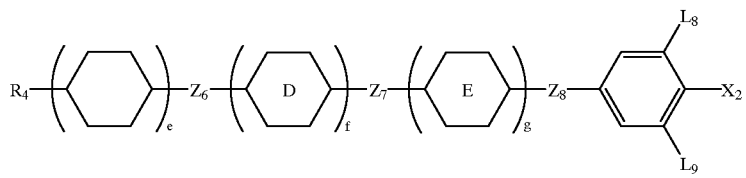

wherein $R_4$ represents a $C_{1-10}$ alkyl group; the rings D and E each independently represents trans-1,4-cyclohexylene group or 1,4-phenylene group; $Z_6$ and $Z_7$ each independently represents —COO— or a covalent bond; $Z_8$ represents —COO— or —C≡C—; $L_8$ and $L_9$ each independently represents —H or —F; $X_2$ represents —F, —$OCF_3$, —$OCF_2H$, —$CF_3$, —$CF_2H$ or —$CFH_2$, provided that when $X_2$ represents —$OCF_3$, —$OCF_2H$, —$CF_3$, —$CF_2H$ or —$CFH_2$, both $L_8$ and $L_9$ represent H; and e, f and g each independently represents an integer of 0 or 1;

(8)

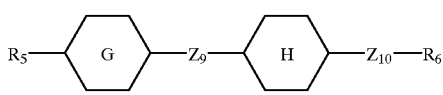

wherein $R_5$ and $R_6$ each independently represents a $C_{1-10}$ alkyl group, a $C_{2-10}$ alkenyl group or a group obtained by replacing one or more methylene groups (—$CH_2$—) in the alkyl or alkenyl group by an oxygen atom (—O—), provided that two or more methylene groups are not consecutively replaced by an oxygen atom; the ring G represents trans-1,4-cyclohexylene group, 1,4-phenylene group or pyrimidine-2,5-diyl group; the ring H represents trans-1,4-cyclohexylene group or 1,4-phenylene group; $Z_9$ represents —C≡C—, —COO—, —$(CH_2)_2$—, —CH=CH—C≡C— or a covalent bond; and $Z_{10}$ represents —COO— or a covalent bond; and wherein $R_7$ and $R_8$ each independently represents a $C_{1-10}$ alkyl group, a $C_{2-10}$ alkenyl group or a group obtained by replacing one or more methylene groups (—$CH_2$—) in the alkenyl group by an oxygen atom (—O—), provided that two or more methylene groups are not consecutively replaced by an oxygen atom; the ring I represents trans-1,4-cyclohexylene group, 1,4-phenylene group or pyrimidine-2,5-diyl group; the ring J represents trans-1,4-cyclohexylene group, or 1,4-phenylene group or pyrimidine-2,5-diyl group one or more hydrogen atoms on which ring may be substituted by a fluorine atom; the ring K represents trans-1,4-cyclohexylene group or 1,4-phenylene group; $Z_{11}$ and $Z_{13}$ each independently represents —COO—, —$(CH_2)_2$— or a covalent bond; $Z_{12}$ represents —CH=CH—, —C≡C—, —COO— or a covalent bond; and h represents an integer of 0 or 1.

A ninth embodiment of the present invention is a liquid crystal composition, comprising as a first component at least one liquid-crystalline compound according to any one of the first to fifth embodiments of the present invention, as a second component at least one compound selected from the group consisting of compounds represented by the general formulae (2), (3) and (4) according to the seventh embodiment of the present invention and as another component at least one compound selected from the group consisting of compounds represented by the general formulae (5), (6), (7), (8) and (9) according to the eighth embodiment of the present invention.

The tenth embodiment of the present invention is a liquid crystal display element, comprising a liquid crystal composition according to any one of the sixth to ninth embodiments of the present invention.

DETAILED DESCRIPTION OF THE INVENTION

The term "liquid crystal compound" as used herein means a compound having a liquid crystal phase. The term "liquid-crystalline compound" as used herein means a compound which can be used as a constituent of a liquid crystal composition. Therefore, a liquid-crystalline compound does not necessarily need to have a liquid crystal phase.

In the compound represented by general formula (1) of the present invention, R and R' each represent a $C_{1-20}$ alkyl or halogenated alkyl group or a group obtained by replacing one or more —$CH_2$— groups in said alkyl group by any one of —O—, —S—, —CH=CH— and —C≡C—, provided that two or more —$CH_2$— groups are not consecutively (9)

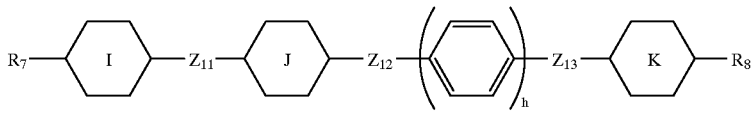

replaced by either —O— or —S—. The term "alkyl group" as used herein means a hydrocarbon group made of carbon and hydrogen. The hydrocarbon group may have a branched structure.

The term "halogenated alkyl group" as used herein means a group obtained by substituting one or more hydrogen atoms in the above described alkyl group by a halogen atom.

Examples of R and R' in the compound represented by the general formula (1) of the present invention include alkyl groups, alkenyl groups (e.g., 1-alkenyl, 2-alkenyl and 3-alkenyl), alkoxy groups, alkylthio groups, alkoxyalkyl groups (e.g., alkoxymethyl and 2-alkoxyethyl), alkylthioalkyl groups (alkylthiomethyl and 2-alkylthioethyl), alkoxyalkoxy groups (e.g., alkoxymethoxy and 2-alkoxyethoxy), alkylthioalkylthio groups (e.g., alkylthiomethylthio and 2-alkylthioethylthio), alkylthioalkoxy groups (e.g., alkylthiomethoxy and 2-alkylthioethoxy), alkoxyalkylthio groups (e.g., alkoxymethylthio and 2-alkoxyethylthio), alkenyloxy groups (e.g., 2-alkenyloxy and 3-alkenyloxy), alkinyl groups (e.g., 1-alkinyl, 2-alkinyl and 3-alkinyl), haloalkyl groups (e.g., ω-haloalkyl groups wherein the halogen atom is preferably a fluorine or chlorine atom, more preferably a fluorine atom).

Specific examples thereof include methyl group, ethyl group, propyl group, butyl group, pentyl group, hexyl group, heptyl group, octyl group, nonyl group, decyl group, undecyl group, dodecyl group, tridecyl group, tetradecyl group, fluoromethyl group, 2-fluoroethyl group, 3-fluoropropyl group, 4-fluorobutyl group, 5-fluoropentyl group, 6-fluorohexyl group, 7-fluoroheptyl group, 8-fluorooctyl group, 9-fluorononyl group, 10-fluorodecyl group, 11-fluoroundecyl group, 12-fluorododecyl group, 13-fluorotridecyl group, 14-fluorotetradecyl group, chloromethyl group, 2-chloroethyl group, 3-chloropropyl group, 4-chlorobutyl group, 5-chloropentyl group, 6-chlorohexyl group, 7-chloroheptyl group, 8-chlorooctyl group, 9-chlorononyl group, 10-chlorodecyl group, 11-chloroundecyl group, 12-chlorododecyl group, 13-chlorotridecyl group and 14-chlorotetradecyl group.

The compound represented by general formula (1) of the present invention is characterized by the possession of three cyclohexane rings. Specific examples of the compound represented by general formula (1) include compounds represented by the following formulae (1-1) to (1-4):

(1-1)

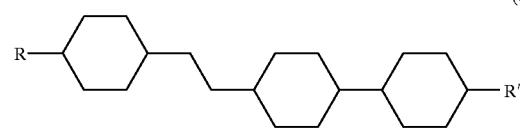

(1-2)

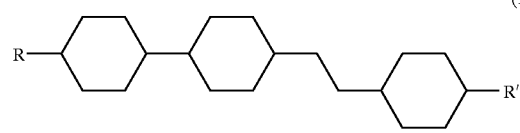

(1-3)

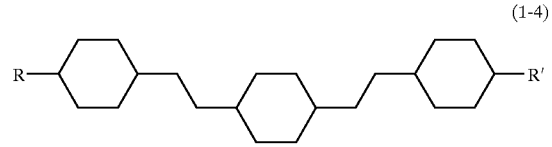

(1-4)

wherein R and R' are as defined above.

Particularly preferred examples of the compound represented by general formula (1) include compounds represented by the following formulae (1-1-1) to (1-4-3). In the formulae, X represents a fluorine or chlorine atom; and m and n each independently represent an integer of from 0 to 19 provided that n≠m in formula (1-1-1).

(1-1-1)

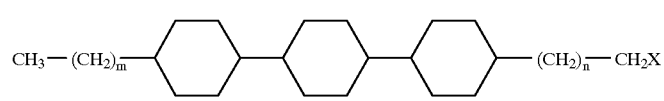

(1-1-2)

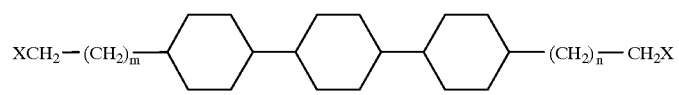

(1-1-3)

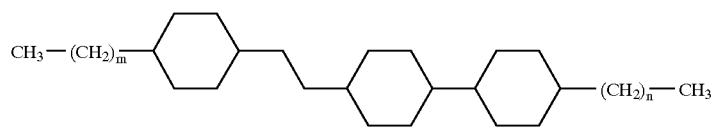

(1-2-1)

-continued

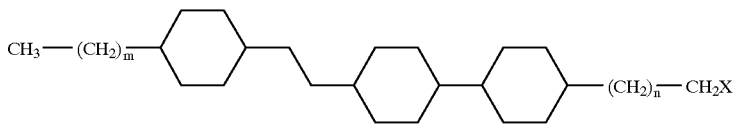
(1-2-2)

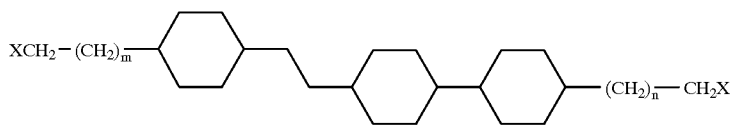
(1-2-3)

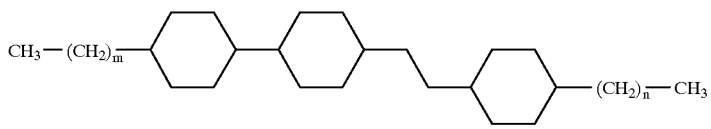
(1-3-1)

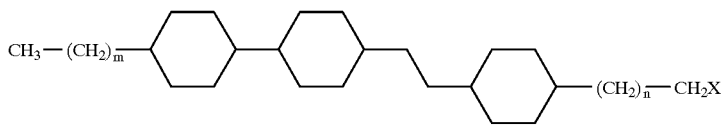
(1-3-2)

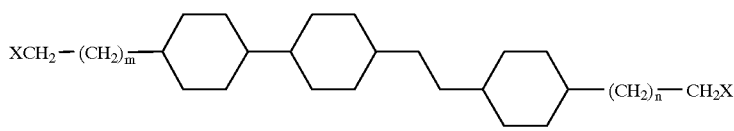
(1-3-3)

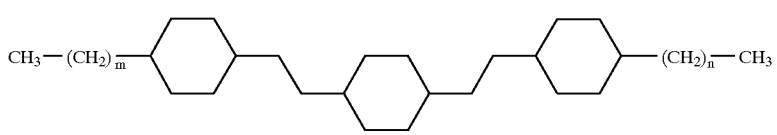
(1-4-1)

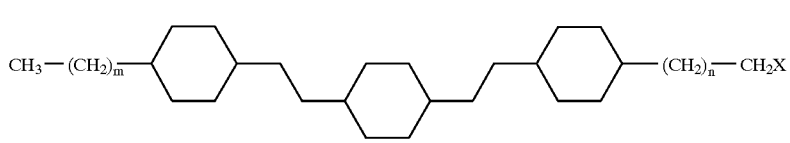
(1-4-2)

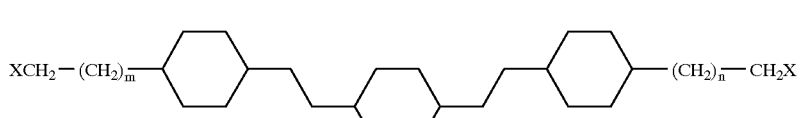
(1-4-3)

The compound represented by the general formula (1) has an extremely low viscosity. As shown in Examples below, it is a surprising fact that the compound of the present invention (Compound No. 10) has an extrapolated viscosity of 20.4 while tricyclic compounds which are now most often used, i.e., comparative Compounds 1 and 2, which are described in JP-B-62-39136 (The term "JP-B" as used herein means an "examined Japanese patent publication"), which correspond to U.S. Pat. No. 4,422,951, have an extrapolated viscosity of 27.1 and 36.1, respectively.

| | Extrapolated viscosity |
|---|---|
| Comparative Compound 1 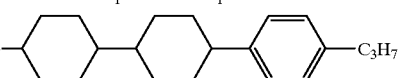 | 27.1 |
| Comparative Compound 2  | 36.1 |
| Compound No. 10 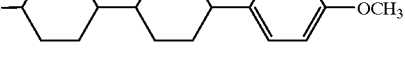 | 20.4 |

The compound represented by general formula (1) of the present invention has an extremely high clearing point. As shown in Examples below, it is a surprising fact that the compound of the present invention (Compound No. 10) has a clearing point of 223.7° C. and an extrapolated clearing point of 189.7° C. while low viscosity compounds which are now widely used, i.e., comparative Compound 3, which is described in JP-B-63-10137 and the above described Comparative Compound 1 have a clearing point of 95.2° C. and 177.5° C., respectively, and an extrapolated clearing point of 60.8° C. and 130.1° C., respectively.

| | Clearing point | Extrapolated Clearing point |
|---|---|---|
| Comparative Compound 3 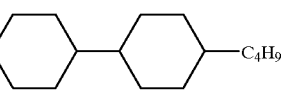 | 95.2° C. | 60.8° C. |
| Comparative Compound 1 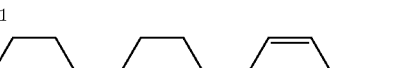 | 177.5° C. | 130.1° C. |
| Compound No. 10 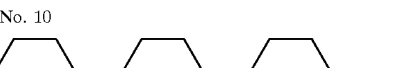 | 223.7° C. | 189.7° C. |

The compound represented by the general formula (1) of the present invention assumes a smectic phase if it is in the form of single compound. However, when the compound represented by general formula (1) is mixed with other liquid crystal compound(s), the rise in the clearing point is induced without causing the reduction of the nematic phase. Further, this is not accompanied by the rise in the lowest allowable temperature of the nematic phase of the resulting composition.

The compound represented by general formula (1) of the present invention exhibits a high chemical stability, i.e., extremely high specific resistance (high voltage holding ratio) and a good ultraviolet stability. The compound represented by general formula (1) has no chemically unstable moiety in its structure and thus is extremely stable. These characteristics are particularly useful for use in a liquid crystal composition for TFT.

Some tercyclohexane compounds have been already disclosed by H. Schubert et al. in J. de Physique, 36, 379 (1975). The compounds disclosed are limited to those terminated by alkyl groups each having the same chain length at both ends thereof. As shown in Examples below, these compounds disclosed all have an extremely low solubility with other liquid crystal compound(s).

On the contrary, the compound represented by the general formula (1) of the present invention exhibits an extremely high solubility with other liquid crystal compound(s). This cannot be analogized from the fact disclosed by H. Schubert et al.

A liquid crystal composition comprising the compound represented by general formula (1) of the present invention does not lose nematic phase even at low temperatures (e.g., −20° C., which is a temperature practically required).

The compound represented by general formula (1) of the present invention is also characterized by its great refractive index anisotropy value. It is well known by those skilled in the art that a compound having a great refractive index anisotropy has many π bonds, i.e., benzene ring, double bond and triple bond in its molecule. In other words, a compound formed only by a cyclohexane ring and a saturated alkyl group has an extremely small refractive index anisotropy value.

However, the compound represented by general formula (1) of the present invention has so great a refractive index anisotropy value that cannot be analogized from a general knowledge of those skilled in the art. As shown in Examples below, the compound of the present invention, e.g., Compound No. 10 exhibits an extrapolated refractive index anisotropy value of 0.087, which is 2.7 times that of comparative Compound 3 as a representative low viscosity compound made only of a cyclohexane ring and a saturated alkyl group (0.032). This is a surprising characteristic that cannot be easily analogized from known facts.

As described above, all compounds represented by general formula (1) of the present invention exhibit desirable physical properties. The use of a compound represented by general formula (1) wherein R, R', $Z_1$ and $Z_2$ are properly selected makes it possible to prepare a liquid crystal composition having properties according to the purpose.

Further, as described above, the compound represented by general formula (1) of the present invention exhibits excellent liquid crystal properties. Thus, the compound represented by general formula (1) of the present invention can be advantageously used for STN and TFT as well as for other purposes, e.g., liquid crystal compound for TN, liquid crystal compound for guest host mode, liquid crystal compound for polymer dispersion type liquid crystal display element, liquid crystal compound for dynamic scattering mode.

The liquid crystal composition according to the present invention preferably comprises one or more compounds represented by general formula (1) incorporated therein in an amount of from 0.1 to 99.9% by weight, preferably from 0.1 to 30% by weight, based on the total weight of the composition to provide excellent properties.

More particularly, the liquid crystal composition according to the present invention preferably comprises at least one compound selected from the group consisting of compounds represented by general formulae (2) to (9) mixed therein in addition to the first component containing at least one compound represented by the general formula (1).

Preferred among the compounds represented by general formulae (2) to (4) for use herein are the following compounds wherein $R_1$ is as defined above:

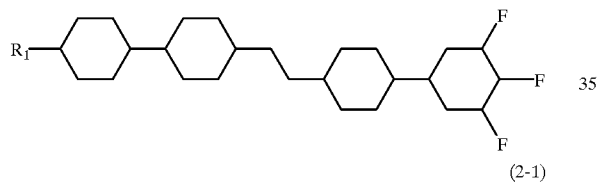
(2-1)

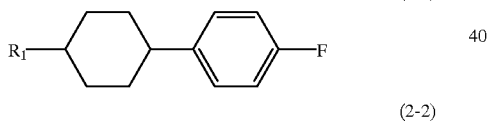
(2-2)

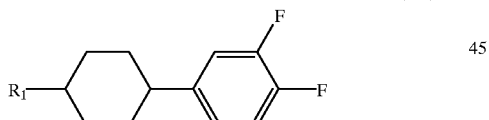
(2-3)

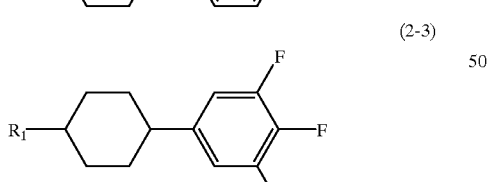
(2-4)

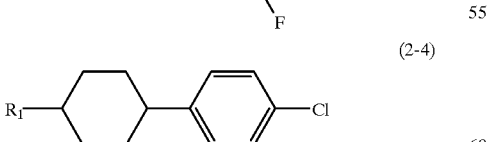
(2-5)

-continued

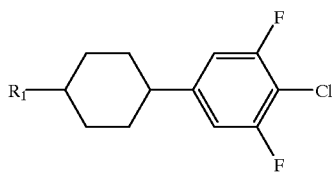
(2-6)

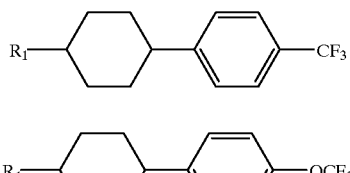
(2-7)

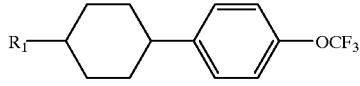
(2-8)

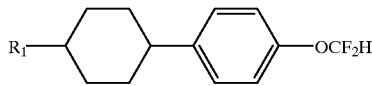
(2-9)

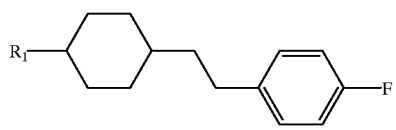
(2-10)

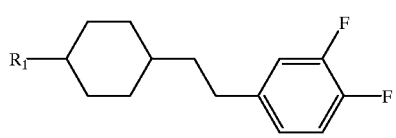
(2-11)

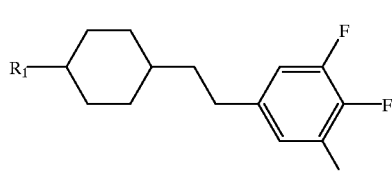
(2-12)

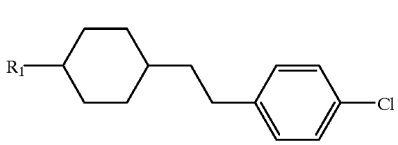
(2-13)

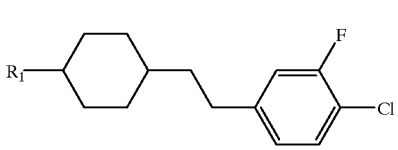
(2-14)

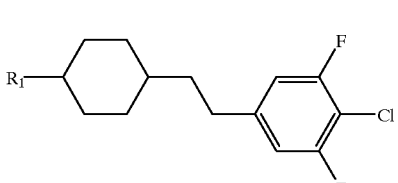
(2-15)

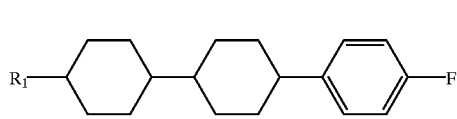
(3-1)

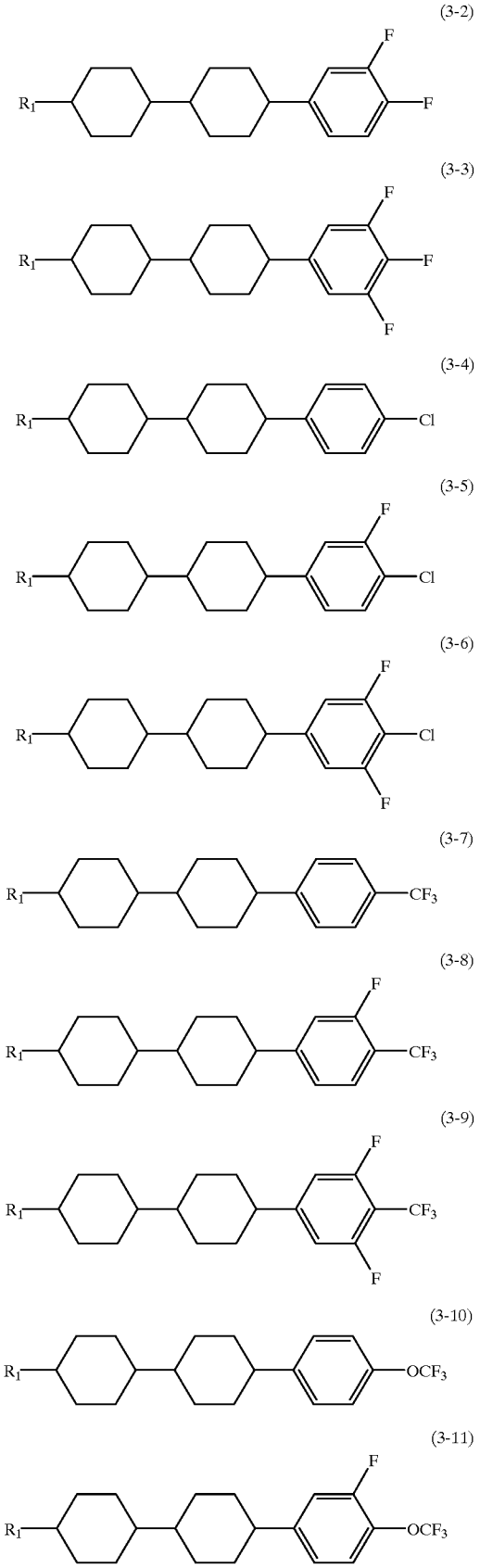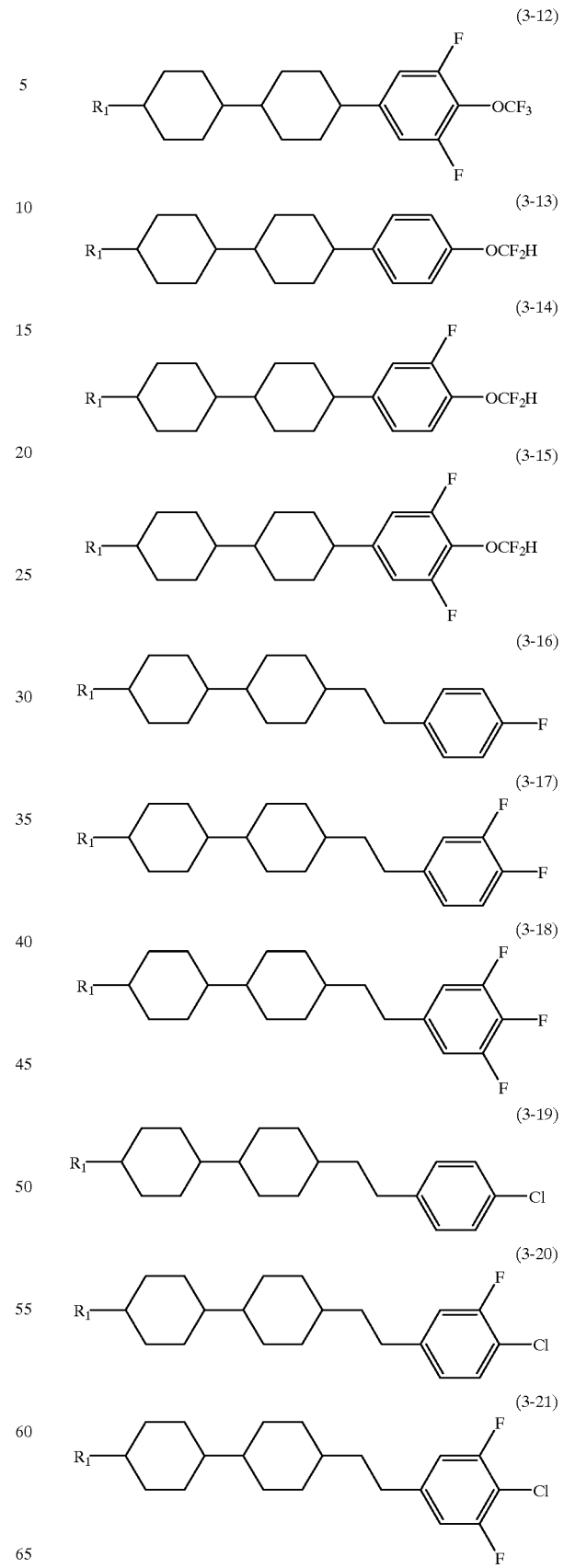

(3-22) 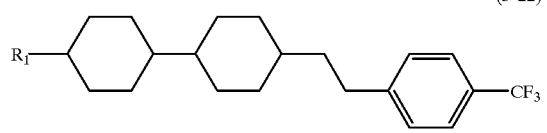
(3-23) 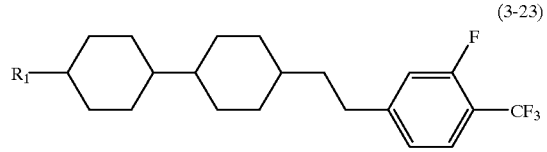
(3-24) 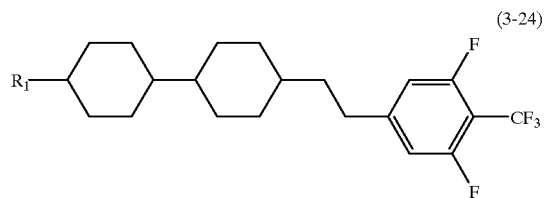
(3-25) 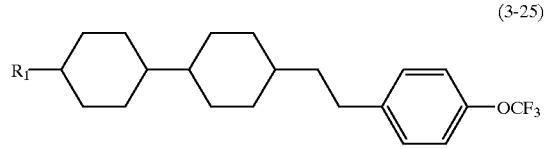
(3-26) 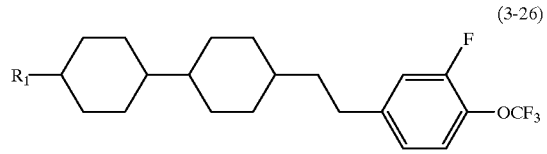
(3-27) 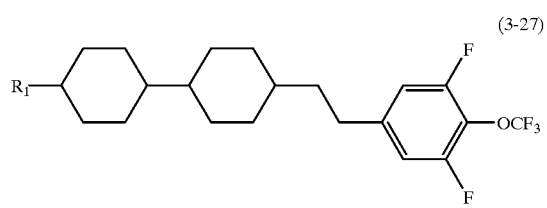
(3-28) 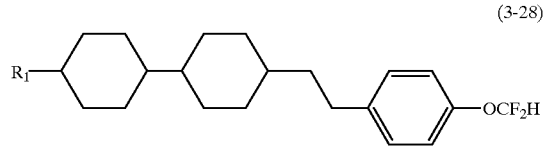
(3-29) 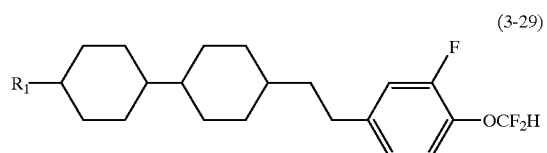
(3-30) 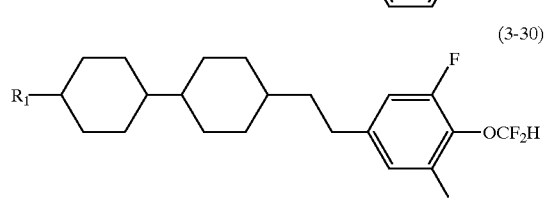
(3-31) 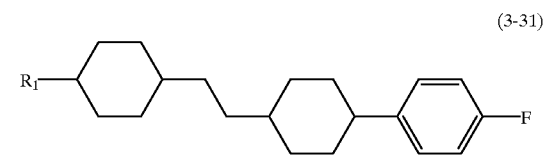
(3-32) 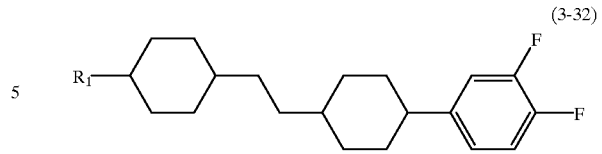
(3-33) 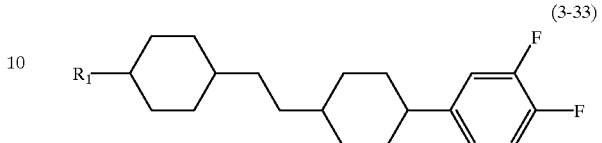
(3-34) 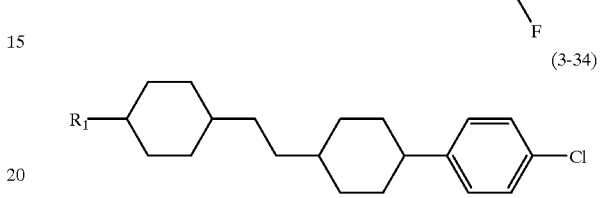
(3-35) 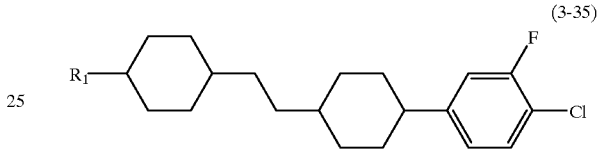
(3-36) 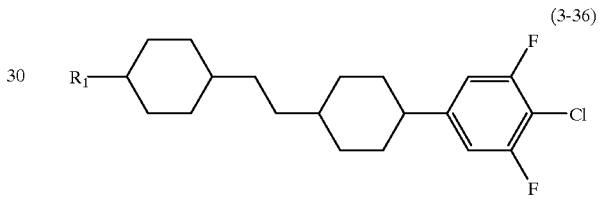
(3-37) 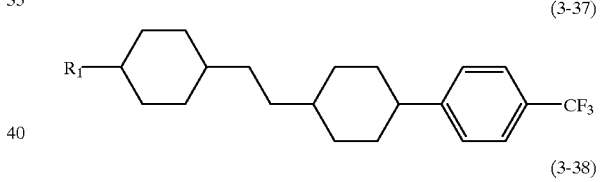
(3-38) 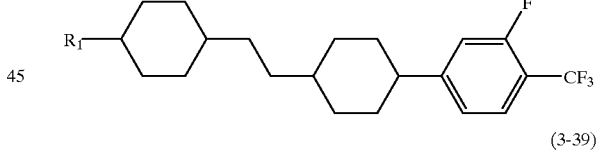
(3-39) 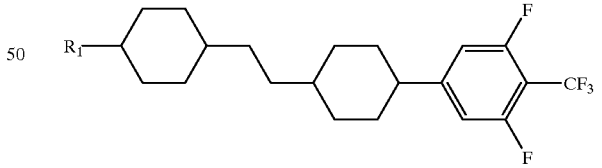
(3-40) 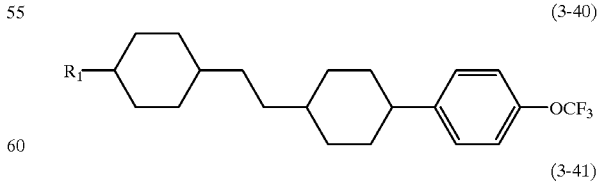
(3-41) 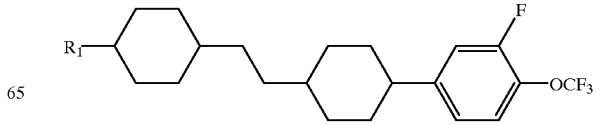

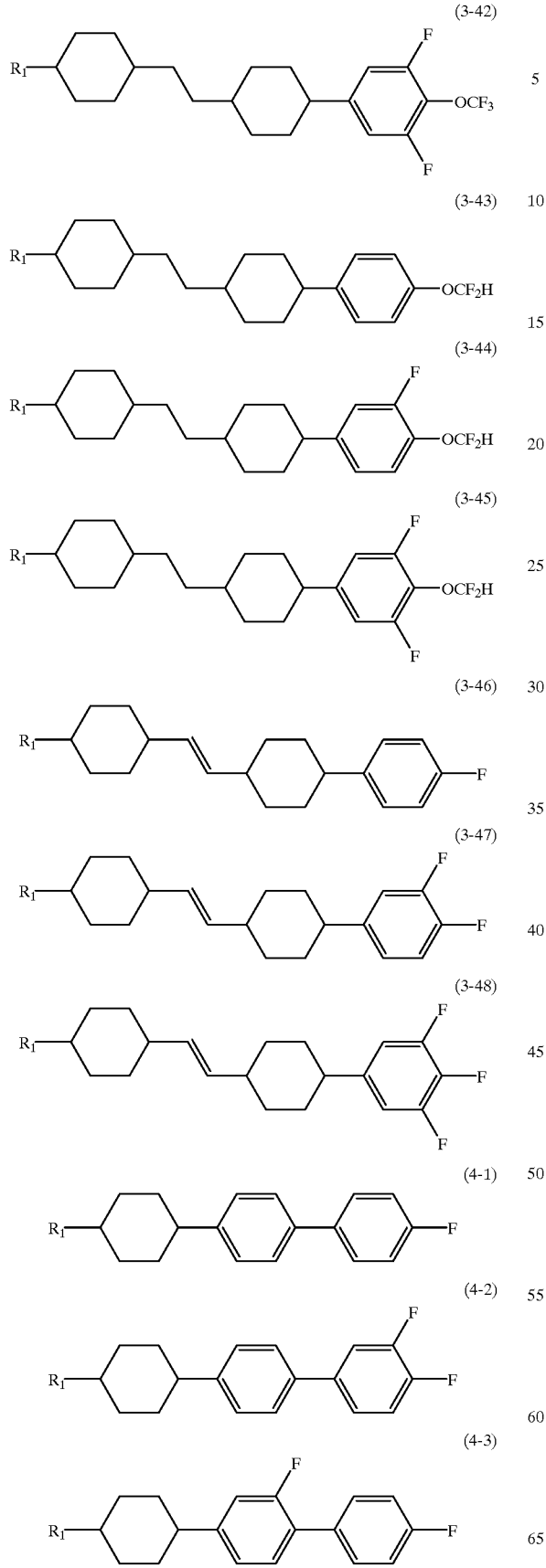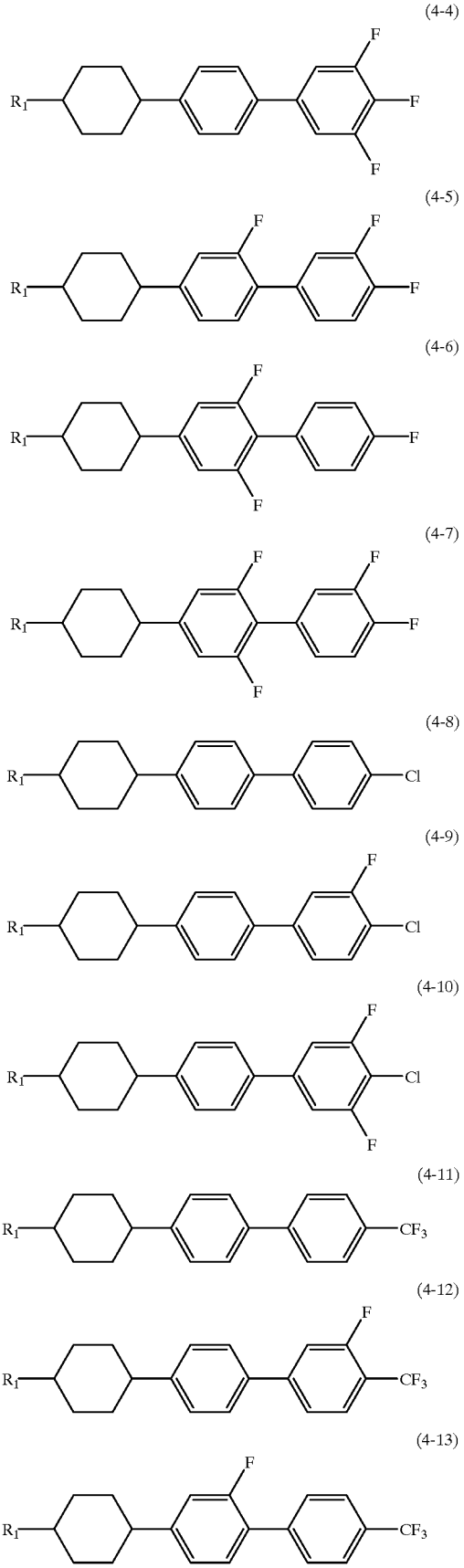

(4-14)
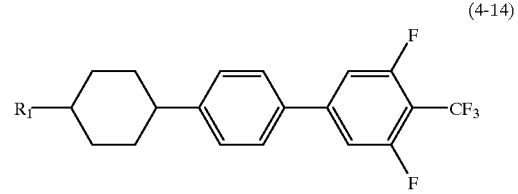
(4-15)
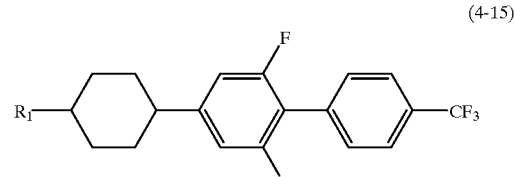
(4-16)
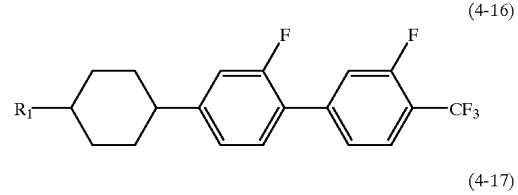
(4-17)
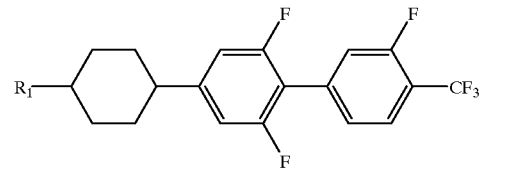
(4-18)
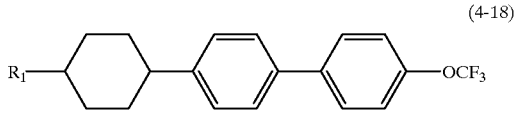
(4-19)
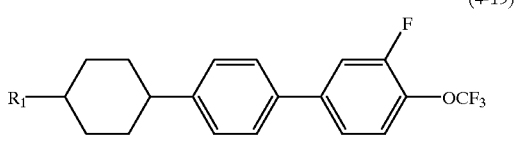
(4-20)
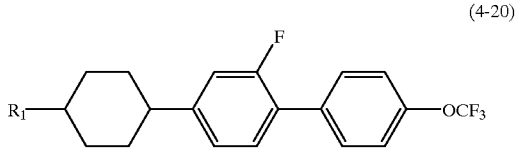
(4-21)
(4-22)
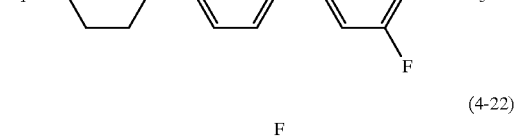
(4-23)
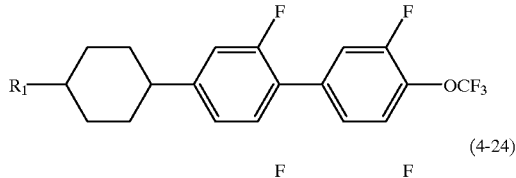
(4-24)
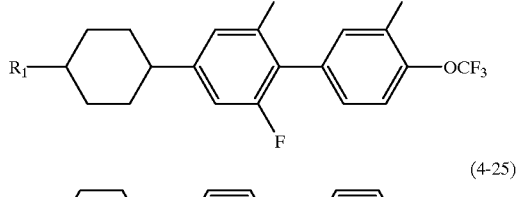
(4-25)
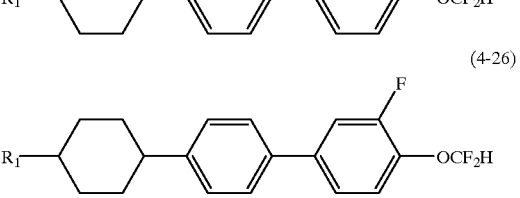
(4-26)
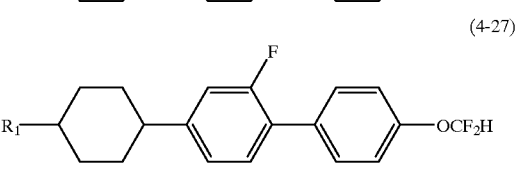
(4-27)
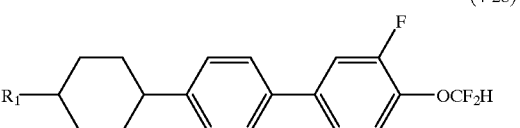
(4-28)
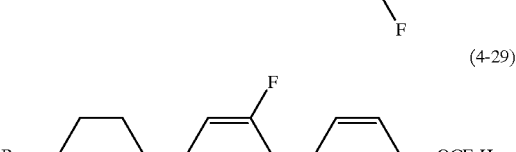
(4-29)
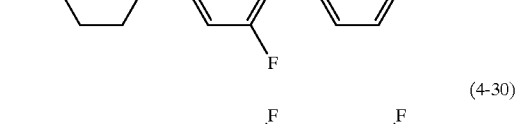
(4-30)
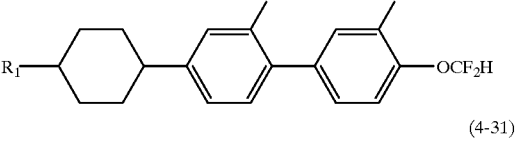
(4-31)
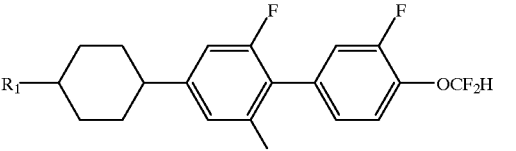
(4-32)
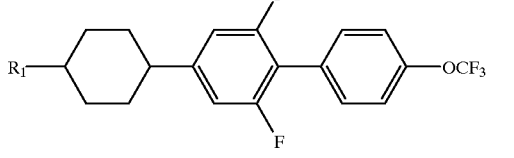

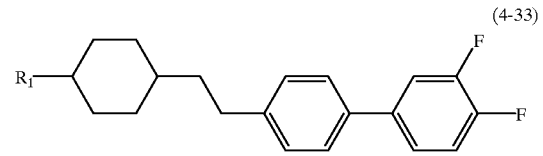 (4-33)
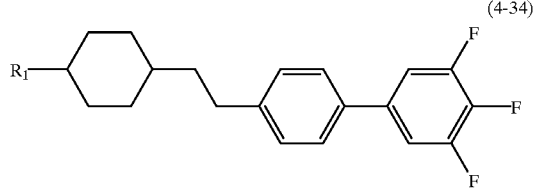 (4-34)
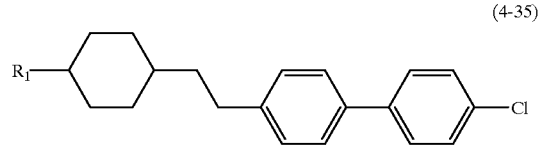 (4-35)
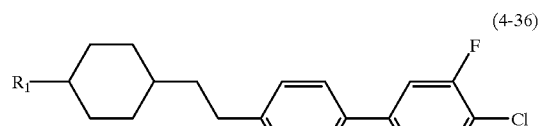 (4-36)
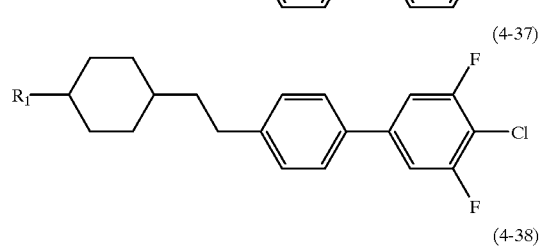 (4-37)
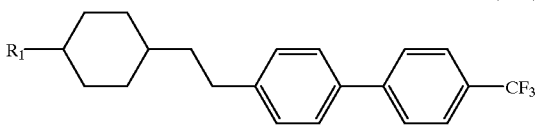 (4-38)
 (4-39)
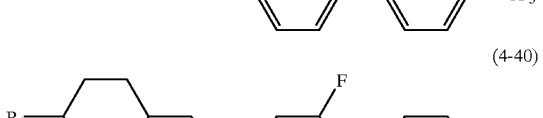 (4-40)
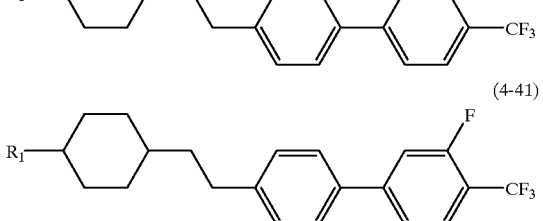 (4-41)
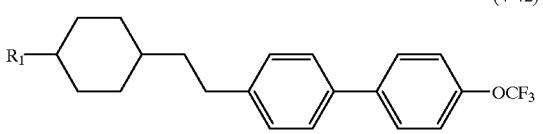 (4-42)
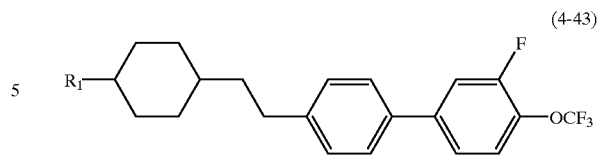 (4-43)
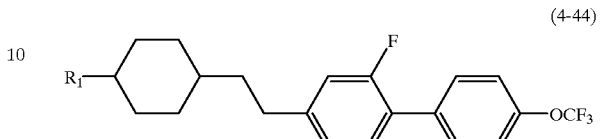 (4-44)
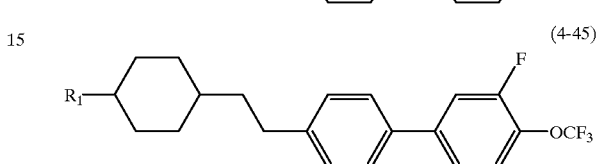 (4-45)
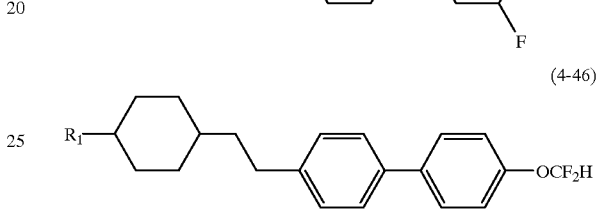 (4-46)
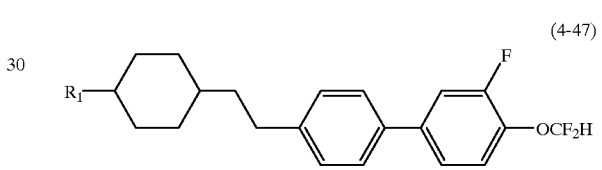 (4-47)
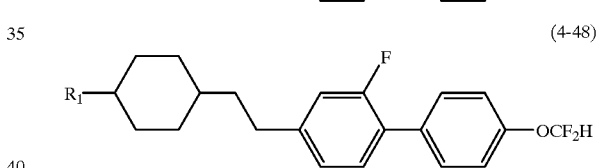 (4-48)
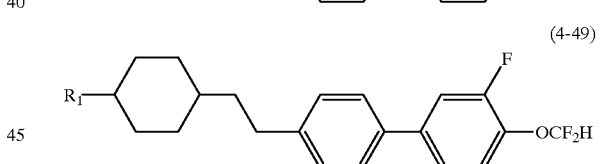 (4-49)
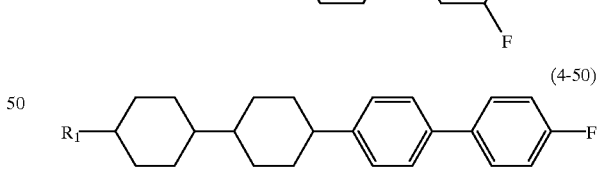 (4-50)
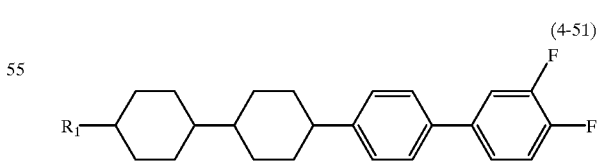 (4-51)
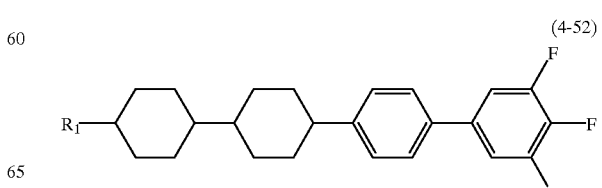 (4-52)

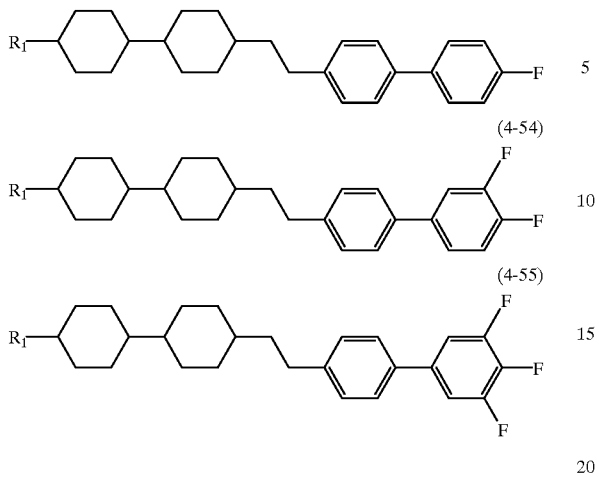

The compounds represented by general formulae (2) to (4) are compounds having a positive dielectric anisotropy and a very excellent thermal or chemical stability and thus are essential for the preparation of a liquid crystal composition for TFT (AM-LCD) which is required to have a high reliability such as high voltage holding ratio and high specific resistance.

The amount of the compounds of general formulae (2) to (4) to be used for the preparation of a liquid crystal composition for TFT generally ranges from 1 to 99% by weight, preferably from 10 to 97% by weight, more preferably from 40 to 95% by weight based on the total weight of the resulting liquid crystal composition. The liquid crystal composition may further comprise one or more compounds selected from the group consisting of the compounds represented by general formulae (5) to (9). Also in the case where a liquid crystal composition for STN display system or ordinary TN display system is prepared, the compounds represented by the general formulae (2) to (4) may be used.

Preferred among the compounds represented by the general formulae (5) to (7) of the present invention are the following compounds, wherein $R_2$, $R_3$ and $R_4$ are as defined above:

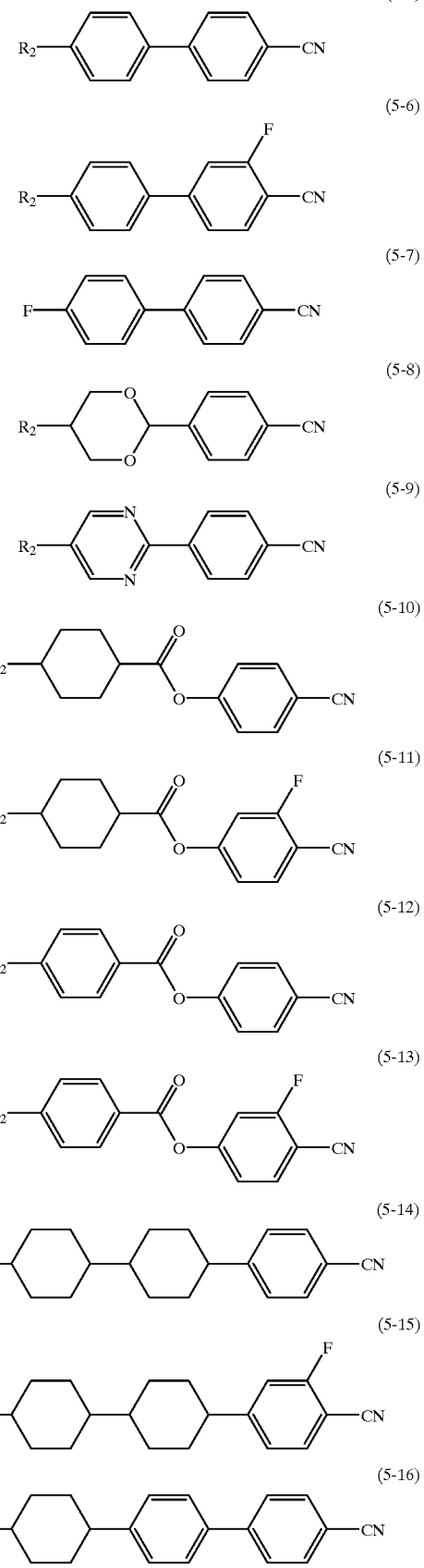

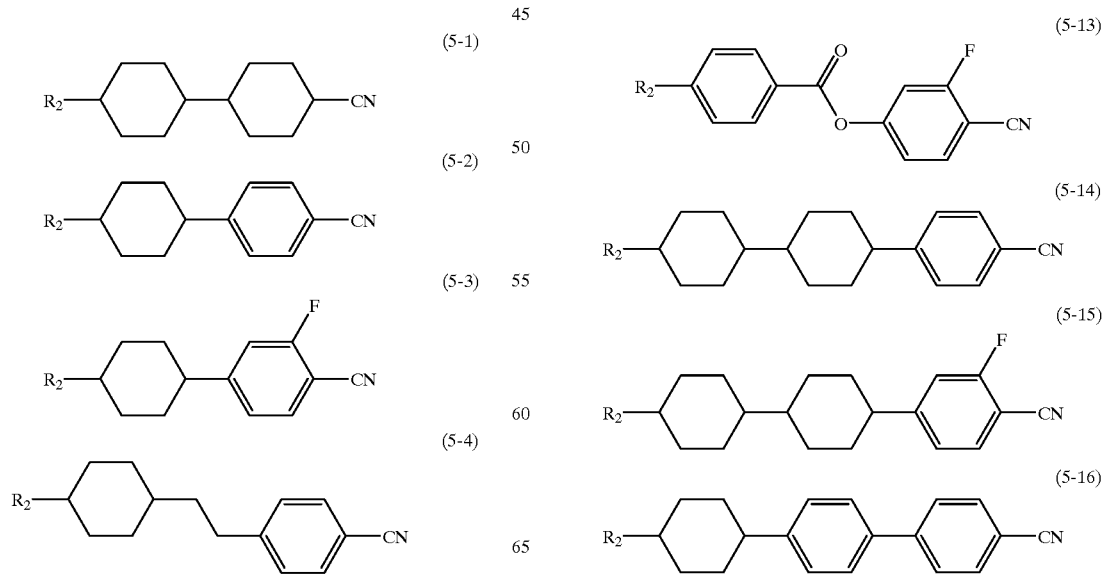

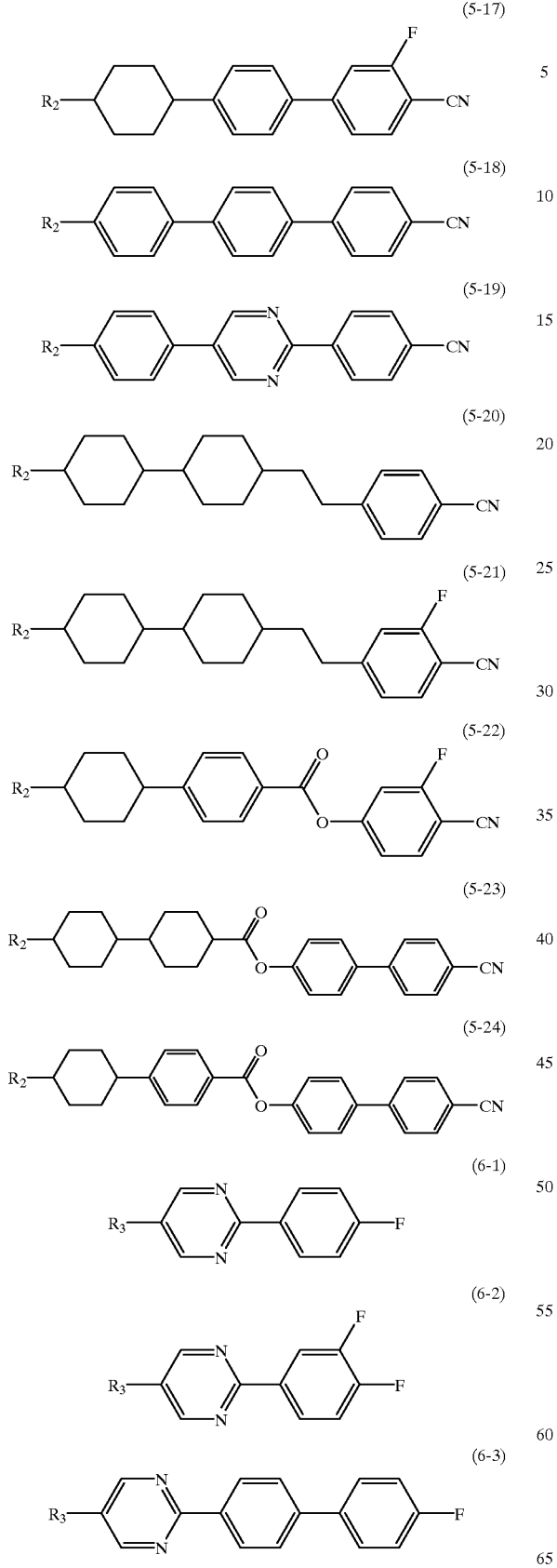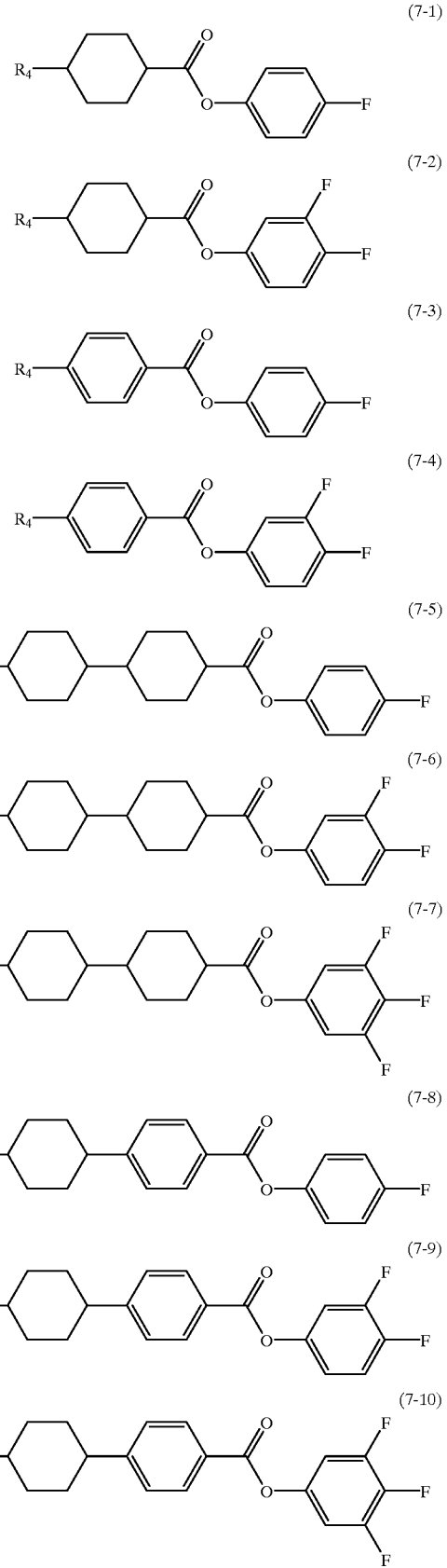

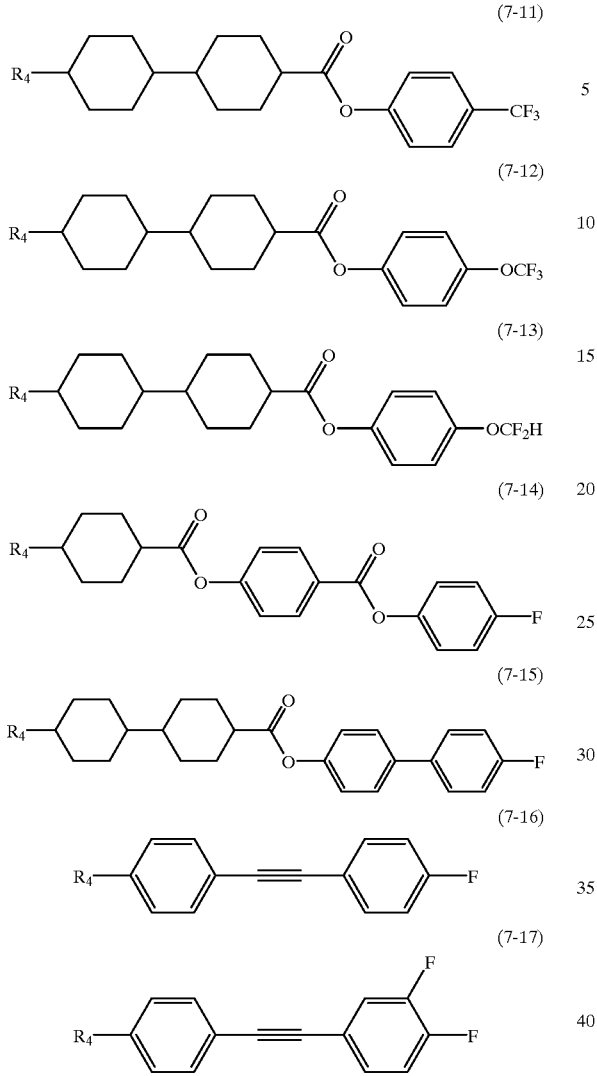

The compounds represented by general formulae (5) to (7) have a great positive dielectric anisotropy value and thus are used for reducing the threshold voltage. These compounds are also used for widening the nematic range such as adjusting viscosity, adjusting refractive index anisotropy and raising clearing point. Further, these compounds are used for improving the steepness of the threshold voltage.

Preferred among the compounds represented by general formulae (8) and (9) are the following compounds, wherein $R_5$, $R_6$, $R_7$ and $R_8$ are as defined above:

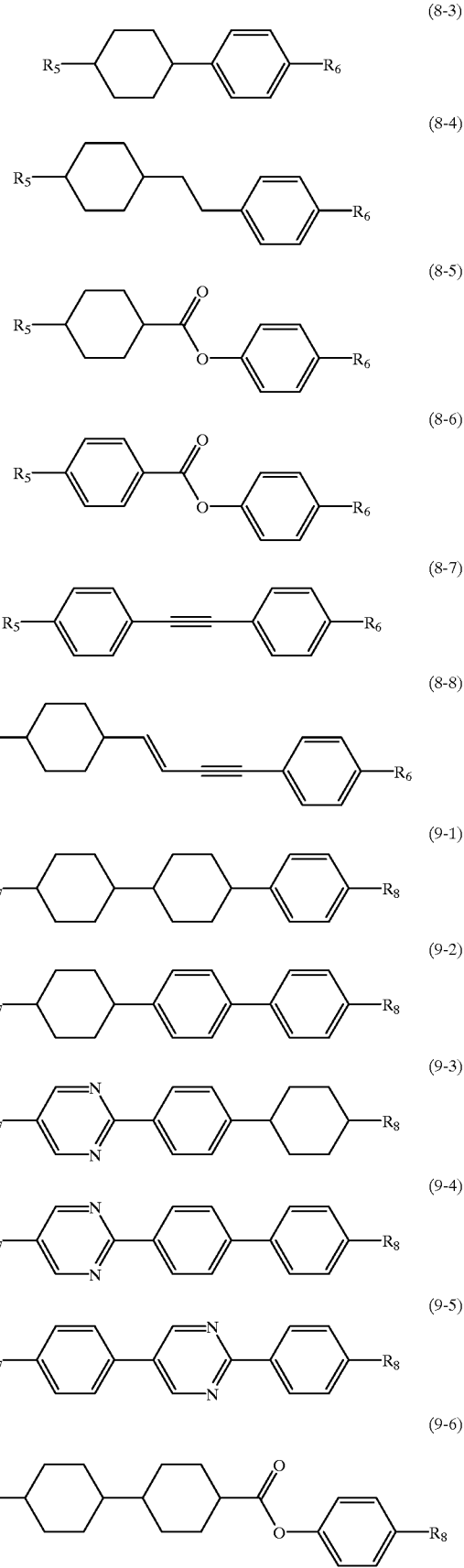

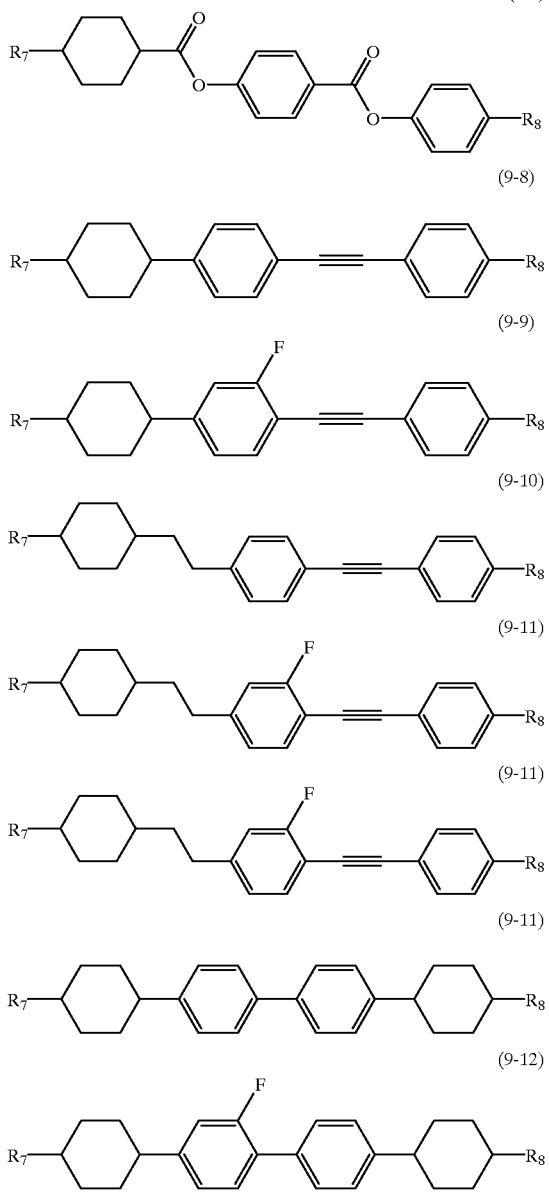

The compounds represented by general formulae (8) and (9) are compounds having a negative or small positive dielectric anisotropy value. The compound represented by general formula (8) is mainly used for reducing the viscosity and/or adjusting the refractive index anisotropy. The compound represented by general formula (9) is used for widening the nematic range such as raising the clearing point and/or for adjusting the refractive index anisotropy.

The compounds represented by general formulae (5) to (9) are particularly essential for the preparation of a liquid crystal composition for STN display system and ordinary TN display system.

The amount of the compounds of general formulae (5) to (9) to be used for the preparation of a liquid crystal composition for ordinary TN display system and STN display system generally ranges from 1 to 99% by weight, preferably from 10 to 97% by weight, more preferably from 40 to 95% by weight. The liquid crystal composition may further comprise one or more compounds selected from the group consisting of the compounds represented by general formulae (2) to (4).

The use of the liquid crystal composition according to the present invention makes it possible to improve the steepness and the viewing angle of the resulting TFT liquid crystal display element. The compound represented by general formula (1) is a low viscosity compound. Accordingly, a liquid crystal display element comprising the compound represented by general formula (1) has an improved and extremely great response.

The liquid crystal composition according to the present invention may be prepared by a conventional method. In general, a method is employed which comprises allowing various components to be dissolved in each other at a high temperature. Alternatively, a liquid crystal may be dissolved in an organic solvent that can dissolve liquid crystals therein to give a mixture from which the solvent is then distilled off under reduced pressure.

The liquid crystal composition of the present invention may comprise proper additives incorporated therein to provide improvements and optimization according to the purpose. These additives are well known by those skilled in the art and are further described in literatures. Such kinds of additives are described, for example, in Ekishou Device Handbook (Handbook for Liquid Crystal Device), pp. 192–202, edited by Nippon Gakujutsu Shinkokai and published by Nikkan Kogyo. In general, a chiral dopant or the like may be incorporated in the liquid crystal composition to induce a helical structure in the liquid crystal, thereby adjusting the twist angle to required value and inhibiting reverse-twist.

The liquid crystal composition according to the present invention may comprise a dichroic dye such as melocyanine dye, styryl dye, azo dye, azomethine dye, azoxy dye, quinophthalon dye, anthraquinone dye and tetrazine dye incorporated therein to provide a liquid crystal composition for guest host (GH) mode. The liquid crystal composition of the present invention can be used as a liquid crystal composition in a polymer dispersion type liquid crystal display element (PDLCD) such as a Nematic Curvilinear Aligned Phase (NCAP) prepared by microcapsulating a nematic liquid crystal or a polymer network liquid crystal display element (PNLCD) comprising a three-dimensional network polymer formed in a liquid crystal. Further, the liquid crystal composition of the present invention can be used as a liquid crystal composition for an electrical controlled birefringence (ECB) mode or dynamic scattering (DS) mode.

Examples of the liquid crystal composition of the present invention, which can be prepared as described above, include the following compositions:

Composition Example 1:
| | | |
|---|---|---|
|  | Compound No. 10 | 5% |
| 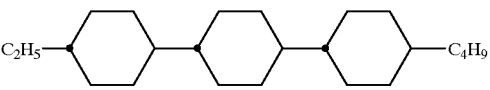 | Compound No. 11 | 5% |
|  | Compound No. 12 | 5% |
| 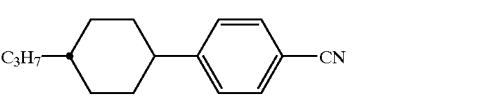 | | 20% |
|  | | 3% |
| 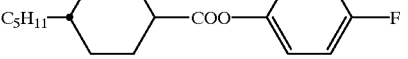 | | 3% |
| 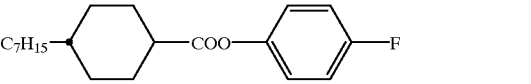 | | 1% |
| 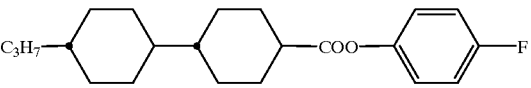 | | 1% |
| 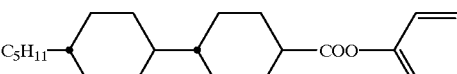 | | 5% |
| 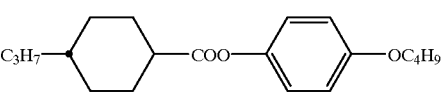 | | 5% |
| 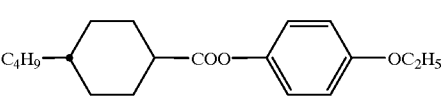 | | 5% |
| 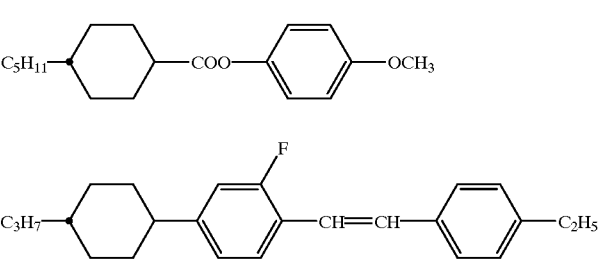 | | 4% |
| 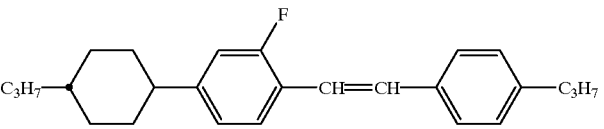 | | 4% |

-continued
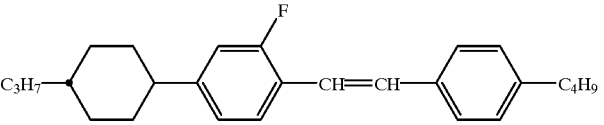 4%
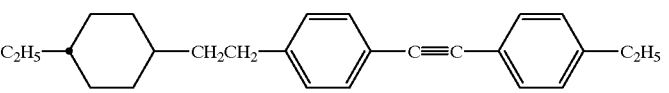 3%
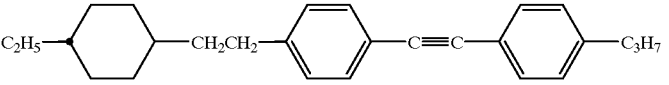 3%
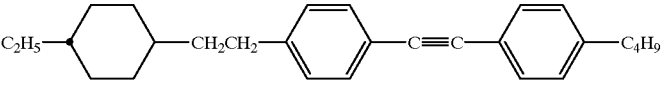 3%
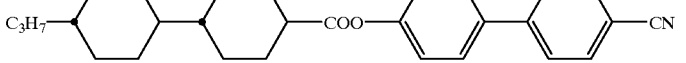 2%
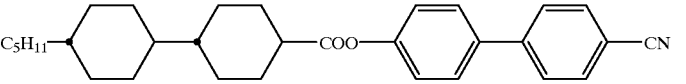 2%
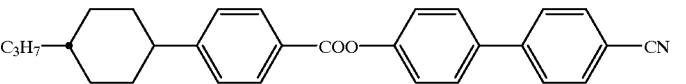 2%
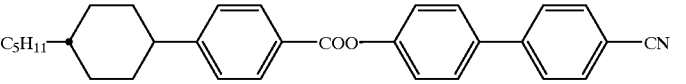 2%
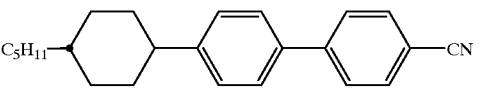 3%
 5%
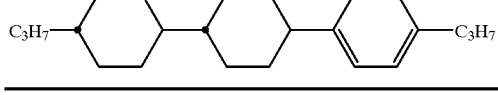 5%
Composition Example 2:
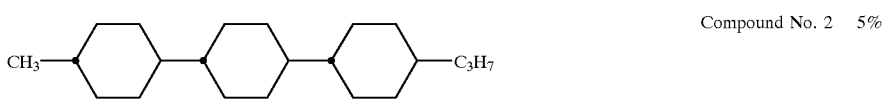 Compound No. 2   5%

-continued

| Structure | % |
|---|---|
| CH₂=CHCH₂CH₂–[Cy]–[Ph]–CN | 10% |
| CH₃CH=CHCH₂CH₂–[Cy]–[Ph]–CN | 10% |
| C₃H₇–[Cy]–[Ph]–CN | 10% |
| C₃H₇–[Cy]–[Ph(F)]–CN | 4% |
| C₃H₇OCH₂–[Ph]–COO–[Ph(F)]–CN | 4% |
| C₃H₇–[Cy]–[Cy]–C₄H₉ | 4% |
| C₂H₅–[Cy]–[Cy]–[Ph]–CH₃ | 4% |
| C₃H₇–[Cy]–[Cy]–[Ph]–OCH₃ | 4% |
| C₃H₇–[Cy]–[Cy]–[Ph]–CH₃ | 8% |
| C₃H₇–[Cy]–[Cy]–[Ph]–C₃H₇ | 10% |
| C₂H₅–[Cy]–CH₂CH₂–[Ph]–C≡C–[Ph]–C₂H₅ | 2% |
| C₂H₅–[Cy]–CH₂CH₂–[Ph]–C≡C–[Ph]–C₄H₉ | 3% |
| C₃H₇–[Cy]–CH₂CH₂–[Ph]–C≡C–[Ph]–C₂H₅ | 4% |

-continued
 4%
 4%
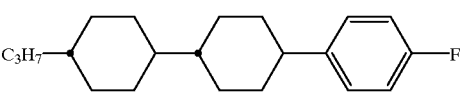 5%
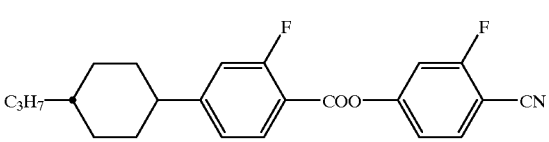 5%
Composition Example 3:
| | | |
|---|---|---|
| 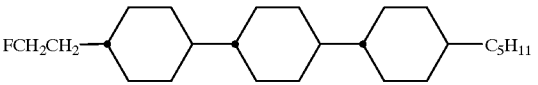 | Compound No. 59 | 5% |
|  | Compound No. 74 | 5% |
| 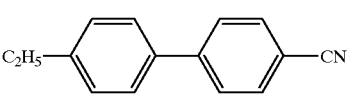 | | 12% |
| 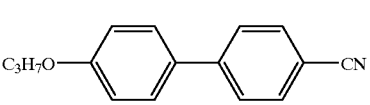 | | 6% |
| 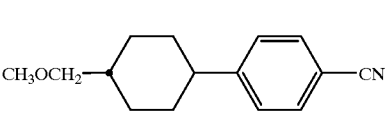 | | 14% |
| 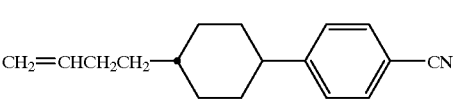 | | 12% |
| 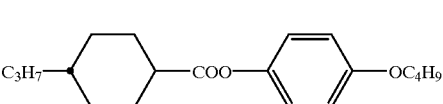 | | 1.6% |
| 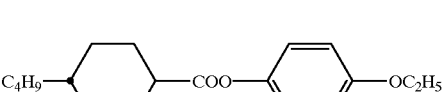 | | 1.2% |

-continued
| Structure | % |
|---|---|
| 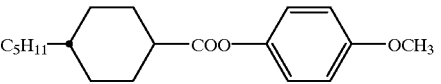 | 1.2% |
| 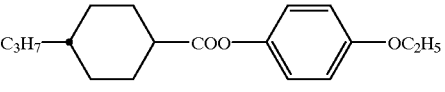 | 1% |
| 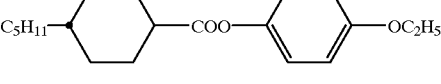 | 0.8% |
| 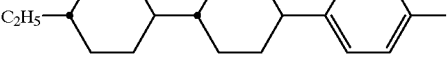 | 6% |
| 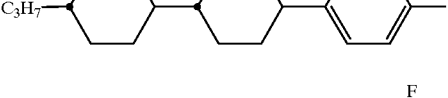 | 6% |
| 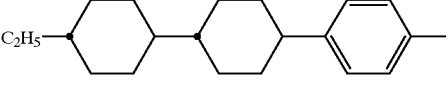 | 4% |
| 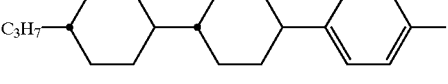 | 5% |
| 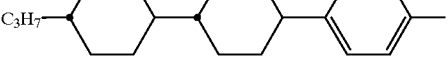 | 4.2% |
| 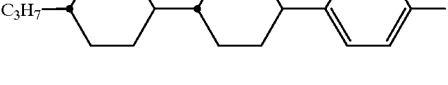 | 10% |
| 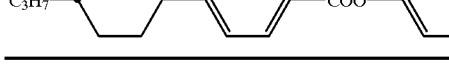 | 5% |
Composition Example 4:
| Structure | | |
|---|---|---|
| 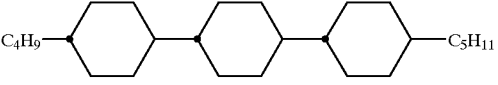 | Compound No. 25 | 3% |
| 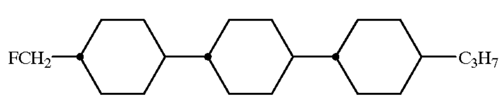 | Compound No. 48 | 3% |

-continued

| Structure | % |
|---|---|
| C₂H₅–⟨phenyl⟩–⟨phenyl⟩–CN | 8% |
| CH₃OCH₂–⟨cyclohexyl⟩–⟨phenyl⟩–CN | 12% |
| C₂H₅–⟨cyclohexyl⟩–⟨cyclohexyl⟩–⟨phenyl⟩–CN | 3% |
| C₃H₇–⟨cyclohexyl⟩–⟨cyclohexyl⟩–⟨phenyl⟩–CN | 4% |
| C₂H₅–⟨cyclohexyl⟩–⟨cyclohexyl⟩–⟨phenyl⟩–CH₃ | 4% |
| C₃H₇–⟨cyclohexyl⟩–⟨cyclohexyl⟩–⟨phenyl⟩–CH₃ | 4% |
| C₃H₇–⟨cyclohexyl⟩–⟨cyclohexyl⟩–⟨phenyl⟩–C₃H₇ | 4% |
| C₃H₇–⟨cyclohexyl⟩–⟨cyclohexyl⟩–⟨phenyl⟩–OCH₃ | 5% |
| C₃H₇–⟨cyclohexyl⟩–⟨cyclohexyl⟩–⟨phenyl⟩–F | 7% |
| CH₃OCH₂–⟨cyclohexyl⟩–⟨cyclohexyl⟩–C₃H₇ | 8% |
| CH₃OCH₂–⟨cyclohexyl⟩–⟨phenyl⟩–C₅H₁₁ | 5% |
| C₃H₇–⟨cyclohexyl⟩–⟨cyclohexyl⟩–CH₂CH₂CH=CH₂ | 3% |
| C₃H₇–⟨cyclohexyl⟩–⟨cyclohexyl⟩–COO–⟨phenyl⟩–⟨phenyl⟩–F | 3% |
| C₄H₉OCH₂CH₂O–⟨cyclohexyl⟩–⟨phenyl⟩–CN | 7% |

-continued
17%
Composition Example 5:
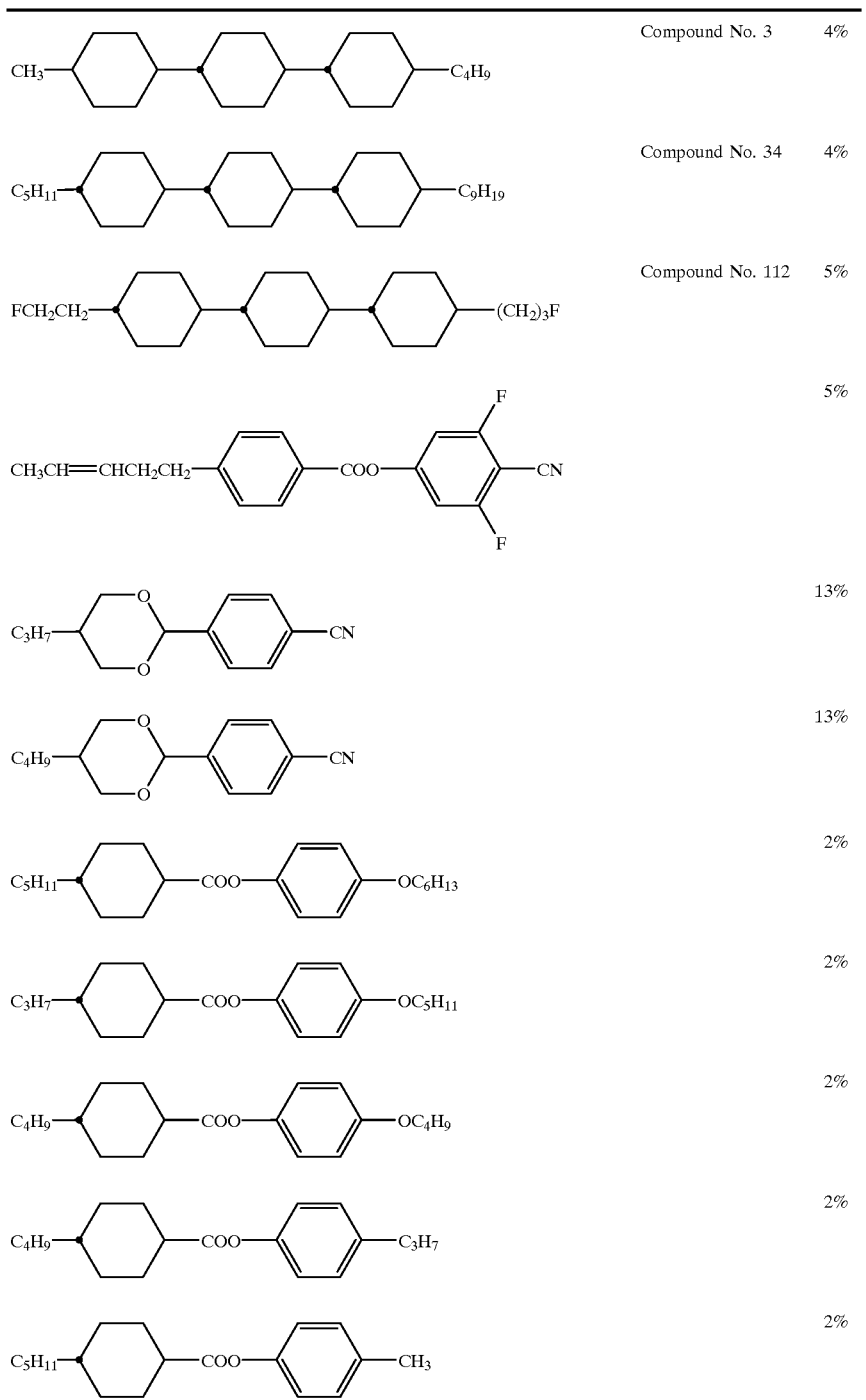
| | | |
|---|---|---|
| Compound No. 3 | 4% | |
| Compound No. 34 | 4% | |
| Compound No. 112 | 5% | |
| | 5% | |
| | 13% | |
| | 13% | |
| | 2% | |
| | 2% | |
| | 2% | |
| | 2% | |
| | 2% | |

| | |
|---|---|
| 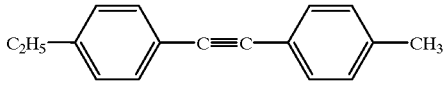 | 5% |
|  | 5% |
|  | 5% |
| 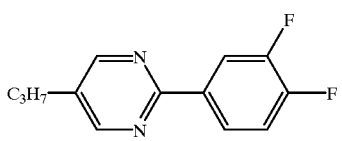 | 12% |
| 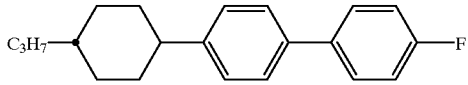 | 6% |
| 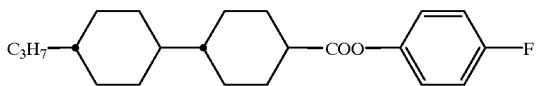 | 4% |
| 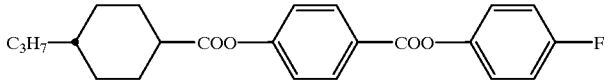 | 3% |
| 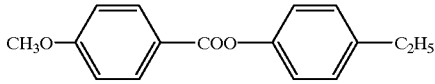 | 3% |
| 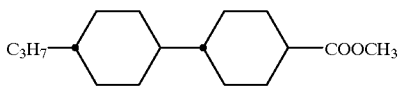 | 3% |
Composition Example 6:
| | |
|---|---|
| 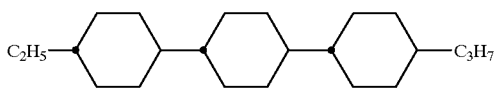 | Compound No. 10 5% |
| 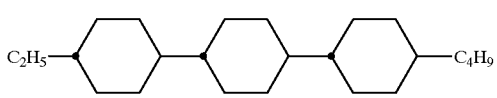 | Compound No. 11 5% |
| 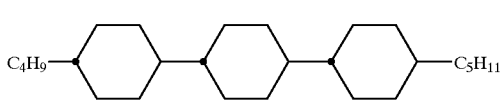 | Compound No. 25 5% |

-continued

| Structure | | |
|---|---|---|
| FCH₂-[Cy]-[Cy]-[Cy]-C₃H₇ | Compound No. 48 | 5% |
| C₄H₉-[Ph]-[Ph]-CN | | 6% |
| C₅H₁₁-[Ph]-[Ph]-CN | | 8% |
| C₂H₅-[Ph]-C≡C-[Ph]-CH₃ | | 8% |
| C₃H₇-[Pyrimidine]-[Ph]-C₂H₅ | | 5% |
| C₄H₉-[Pyrimidine]-[Ph]-C₂H₅ | | 5% |
| C₃H₇-[Pyrimidine]-[Ph]-[Ph]-F | | 6% |
| C₄H₉-[Pyrimidine]-[Ph]-[Ph]-F | | 6% |
| C₅H₁₁-[Pyrimidine]-[Ph]-[Ph]-F | | 6% |
| CH₂=CH-[Cy]-[Cy]-[Ph]-CH₃ | | 5% |
| CH₂=CHCH₂-[Cy]-[Cy]-[Ph]-CH₃ | | 5% |
| C₂H₅-[Cy]-CH₂CH₂-[Ph]-C≡C-[Ph]-C₂H₅ | | 4% |
| C₂H₅-[Cy]-CH₂CH₂-[Ph]-C≡C-[Ph]-C₃H₇ | | 4% |
| C₂H₅-[Cy]-CH₂CH₂-[Ph]-C≡C-[Ph]-C₄H₉ | | 4% |

-continued
| | |
|---|---|
| 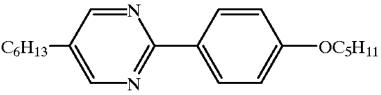 | 2% |
| 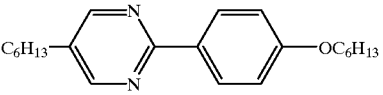 | 2% |
| 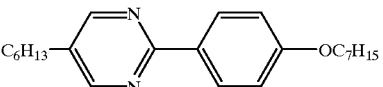 | 2% |
| 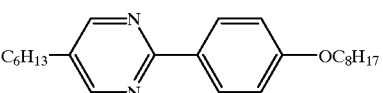 | 2% |
Composition Example 7:
| | | |
|---|---|---|
| 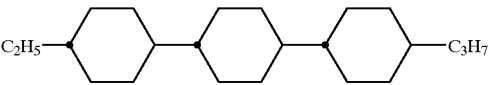 | Compound No. 10 | 3% |
| 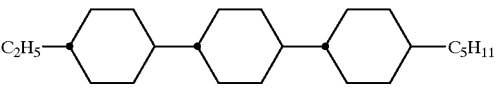 | Compound No. 12 | 3% |
| 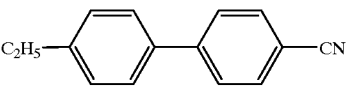 | | 9% |
| 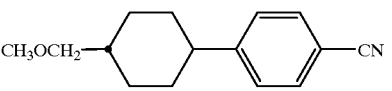 | | 10% |
| 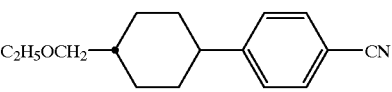 | | 7% |
| 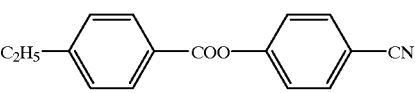 | | 7% |
| 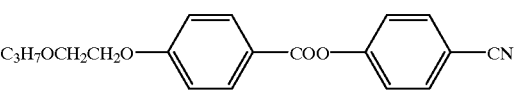 | | 5% |
| 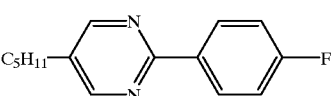 | | 8% |

-continued
| Structure | % |
|---|---|
| 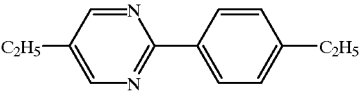 | 2% |
| 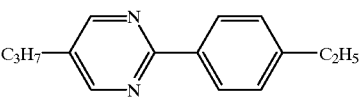 | 2% |
| 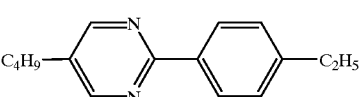 | 2% |
|  | 5% |
| 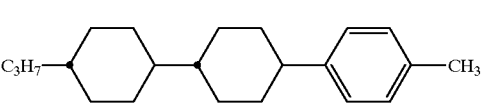 | 5% |
| 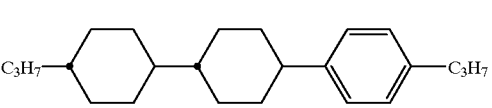 | 10% |
| 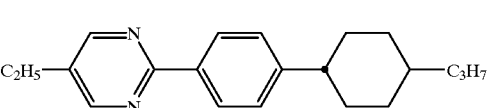 | 5% |
| 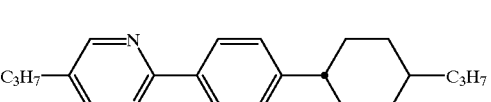 | 5% |
|  | 5% |
| 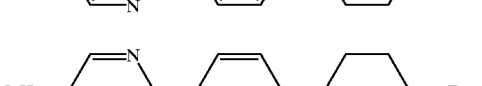 | 2% |
| 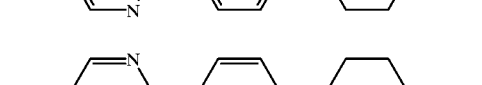 | 2% |
| 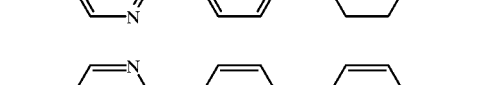 | 3% |

Composition Example 8:
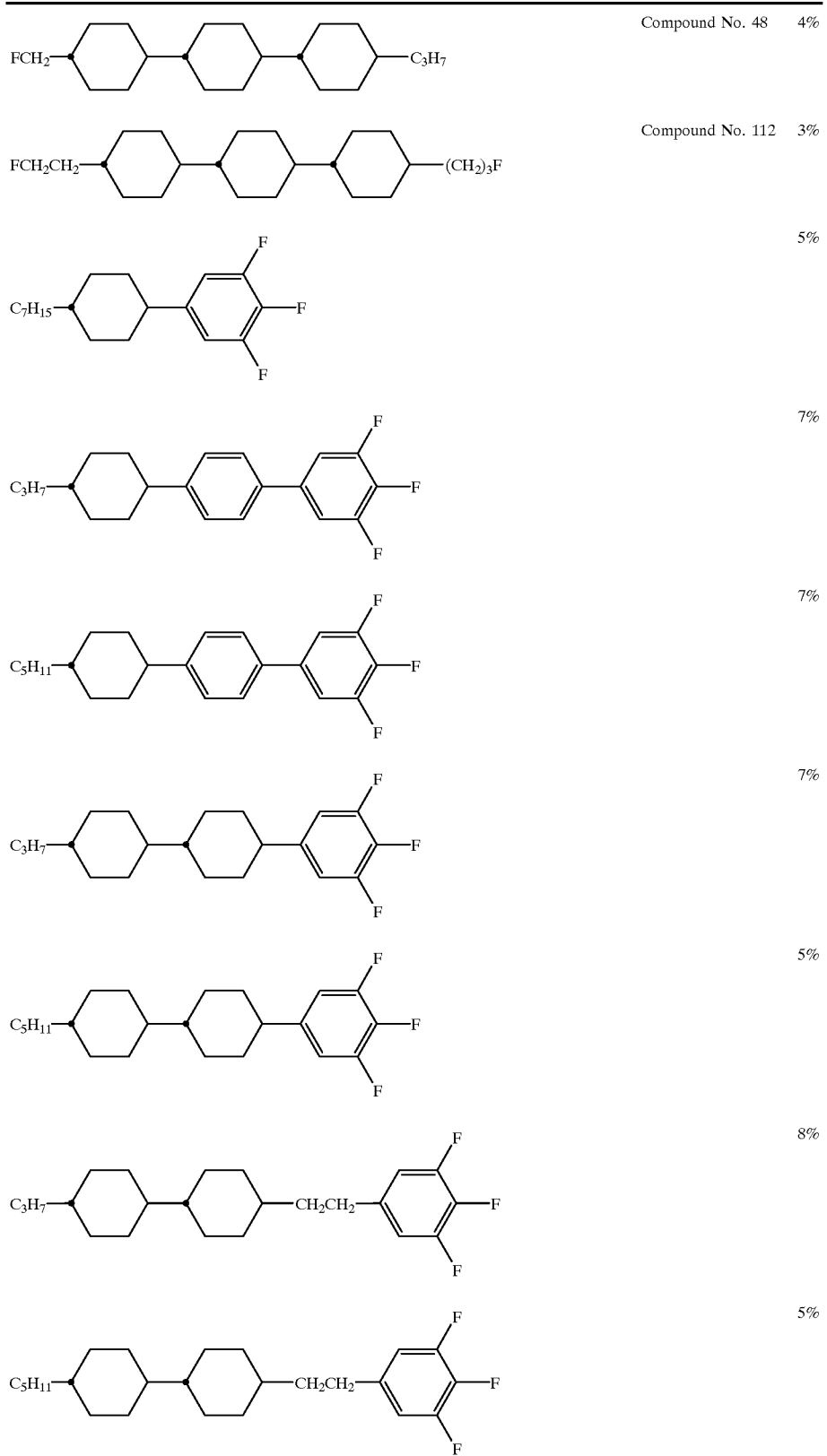

-continued
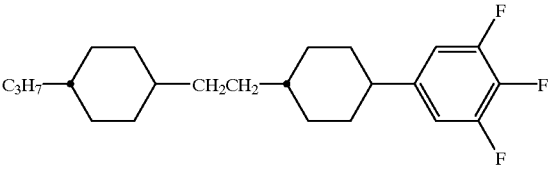 8%
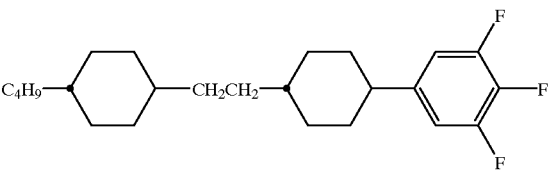 8%
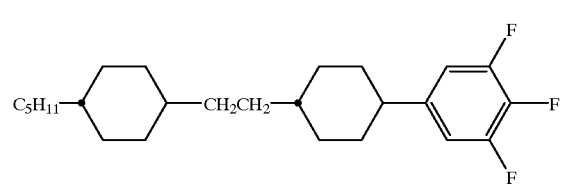 8%
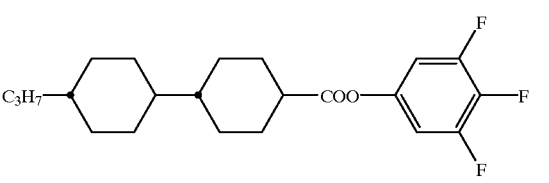 5%
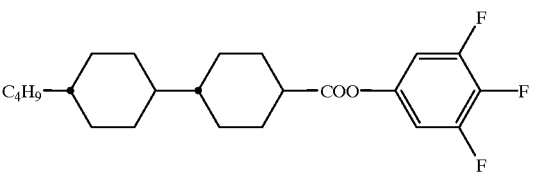 3%
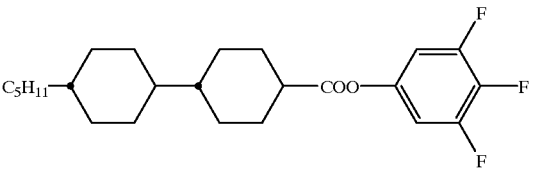 3%
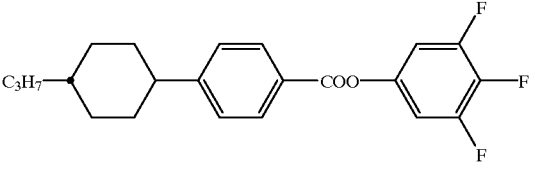 2%
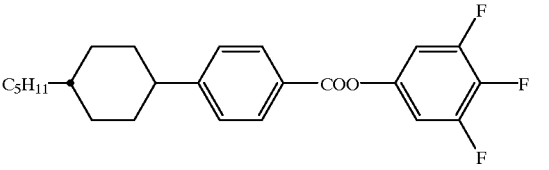 2%

-continued
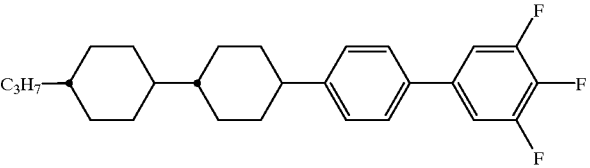 2%
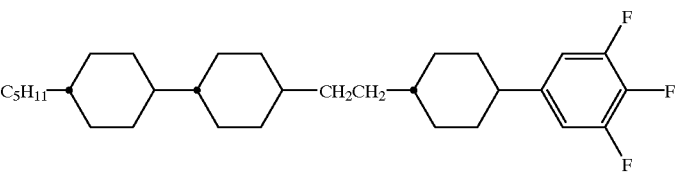 2%
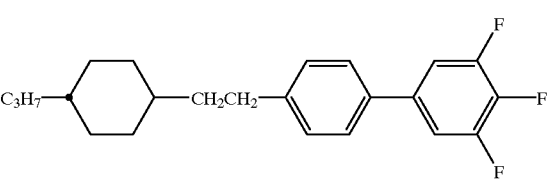 3%
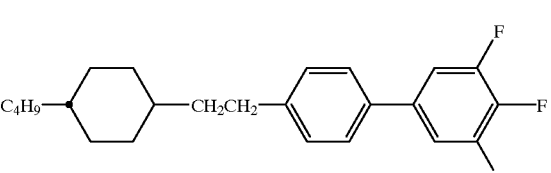 3%
Composition Example 9:
| | | |
|---|---|---|
| 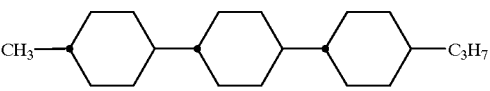 | Compound No. 2 | 5% |
| 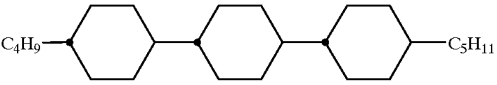 | Compound No. 25 | 5% |
| 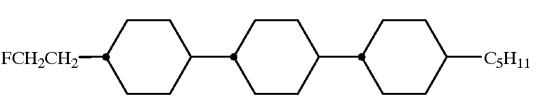 | Compound No. 59 | 5% |
| 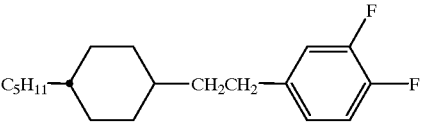 | | 4% |
| 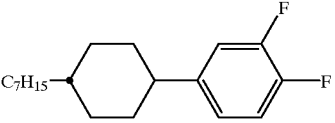 | | 10% |

-continued
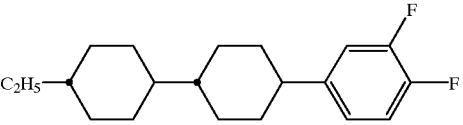 11%
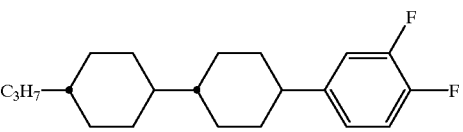 11%
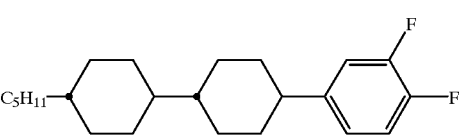 11%
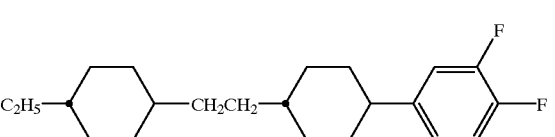 12%
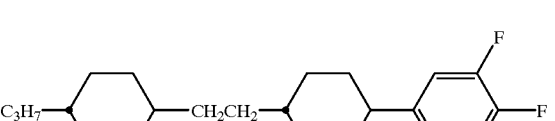 6%
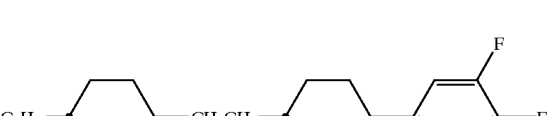 12%
 2%
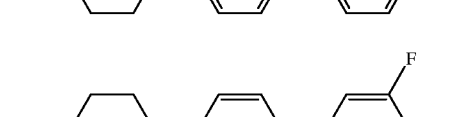 2%
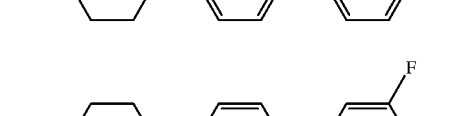 4%
Composition Example 10:
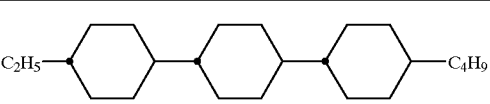 Compound No. 11   3%

-continued

| Structure | | |
|---|---|---|
| FCH₂–Cy–Cy–Cy–C₃H₇ | Compound No. 48 | 3% |
| C₇H₁₅–Cy–Ph(3-F,4-F) | | 5% |
| C₃H₇–Cy–Ph–OC₂H₅ | | 16% |
| C₃H₇–Cy–Cy–C₄H₉ | | 3% |
| C₂H₅–Cy–Cy–Ph(3-F,4-F) | | 10% |
| C₃H₇–Cy–Cy–Ph(3-F,4-F) | | 10% |
| C₅H₁₁–Cy–Cy–Ph(3-F,4-F) | | 10% |
| C₂H₅–Cy–CH₂CH₂–Cy–Ph(3-F,4-F) | | 10% |
| C₃H₇–Cy–CH₂CH₂–Cy–Ph(3-F,4-F) | | 5% |
| C₅H₁₁–Cy–CH₂CH₂–Cy–Ph(3-F,4-F) | | 10% |
| C₂H₅–Cy–Cy–Ph(3-F,4-F,5-F) | | 3% |

-continued
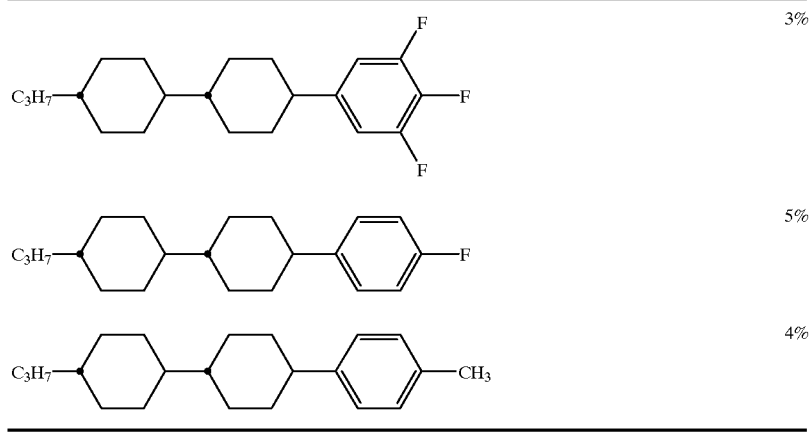
Composition Example 11:
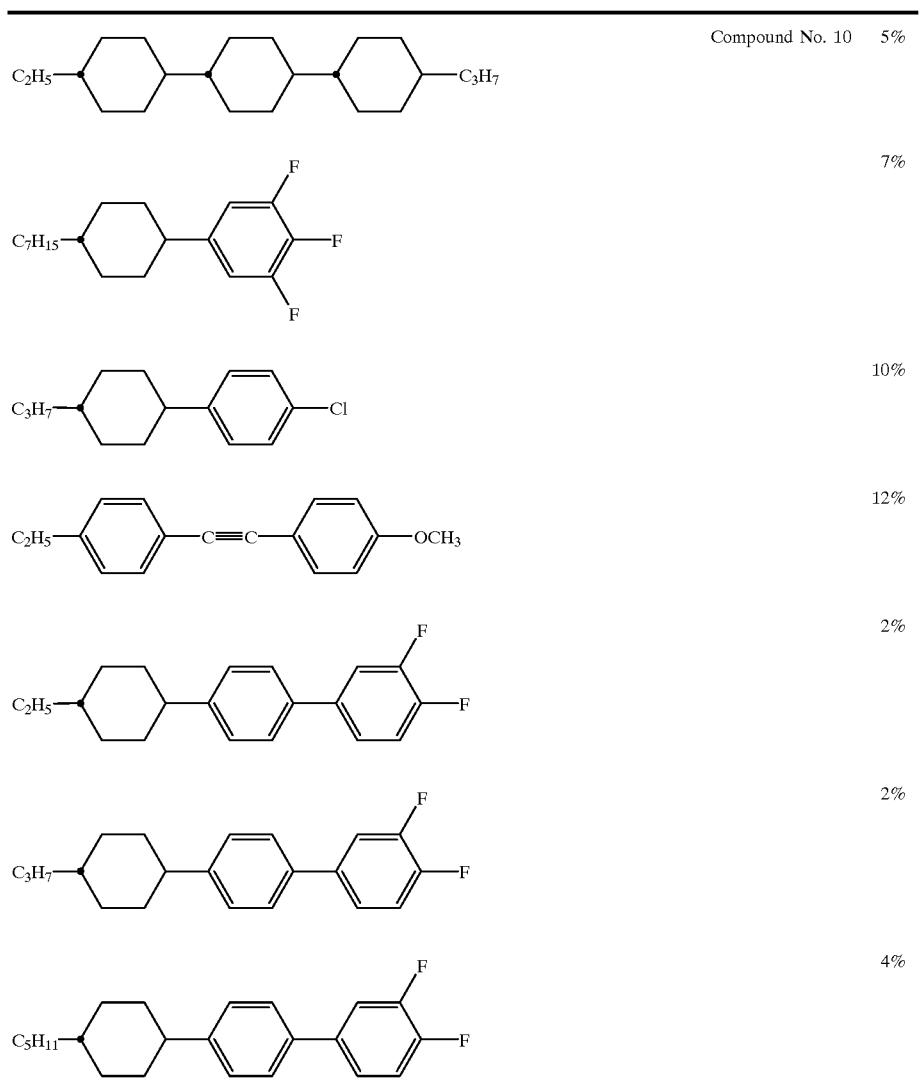

-continued
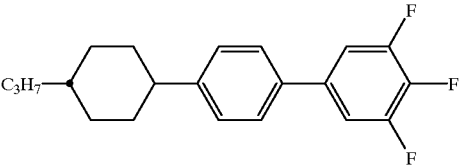 10%
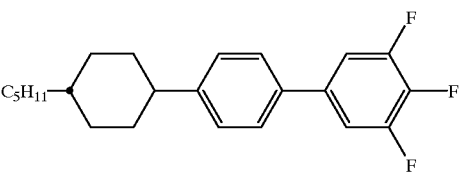 10%
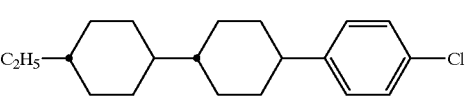 10%
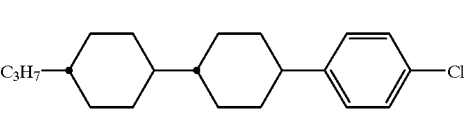 5%
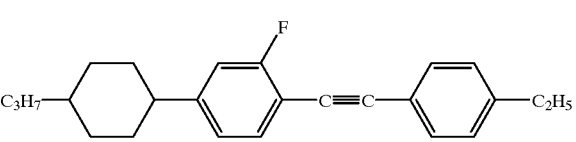 4%
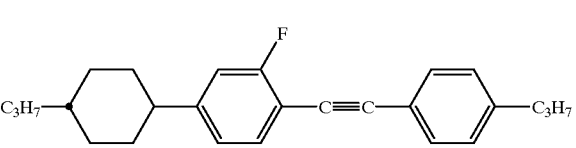 4%
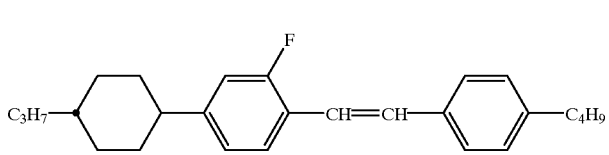 4%
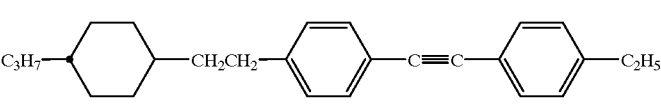 3%
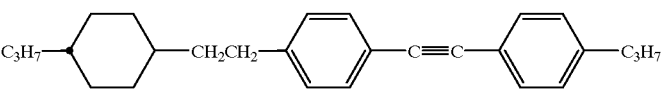 3%
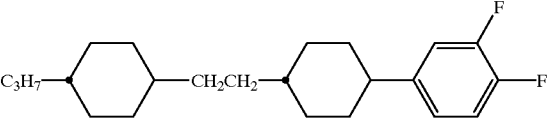 3%
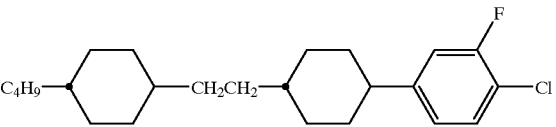 2%

Composition Example 12:

| Structure | Label | % |
|---|---|---|
| CH₃—[Cy]—[Cy]—[Cy]—C₃H₇ | Compound No. 2 | 5% |
| C₂H₅—[Cy]—[Cy]—[Cy]—C₃H₇ | Compound No. 10 | 5% |
| C₄H₉—[Cy]—[Cy]—[Cy]—C₅H₁₁ | Compound No. 25 | 5% |
| C₅H₁₁—[Cy]—[Ph]—F | | 3% |
| C₆H₁₃—[Cy]—[Ph]—F | | 3% |
| C₇H₁₅—[Cy]—[Ph]—F | | 3% |
| C₃H₇—[Cy]—[Cy]—[Ph]—OCHF₂ | | 4% |
| C₅H₁₁—[Cy]—[Cy]—[Ph]—OCHF₂ | | 4% |
| C₃H₇—[Cy]—[Cy]—[Ph(2,6-F₂)]—OCHF₂ | | 10% |
| C₅H₁₁—[Cy]—[Cy]—[Ph(2,6-F₂)]—OCHF₂ | | 10% |
| C₂H₅—[Cy]—[Cy]—[Ph]—OCF₃ | | 5% |
| C₃H₇—[Cy]—[Cy]—[Ph]—OCF₃ | | 5% |

-continued
 5%
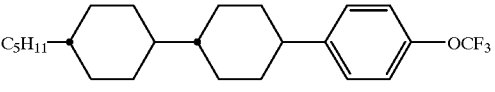 5%
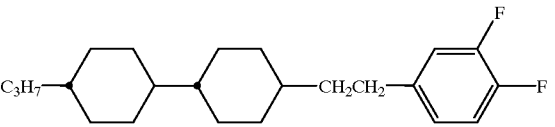 10%
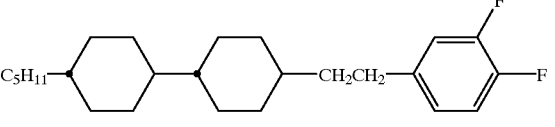 10%
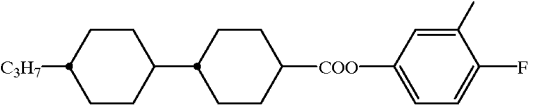 4%
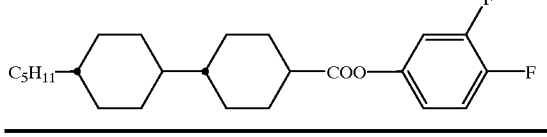 4%
Composition Example 13:
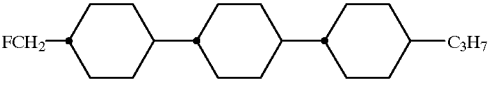 Compound No. 48 5%
 Compound No. 59 3%
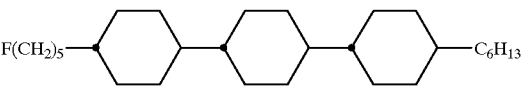 Compound No. 81 3%
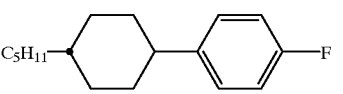 13%
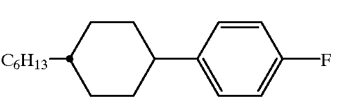 13%

-continued
| | |
|---|---|
| 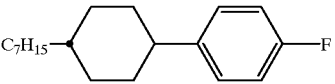 | 13% |
|  | 4% |
|  | 4% |
| 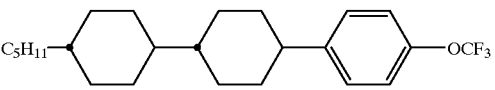 | 4% |
| 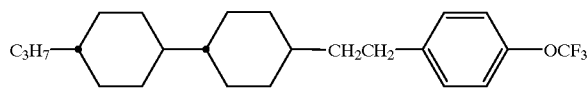 | 5% |
| 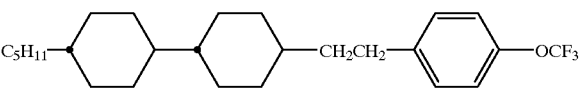 | 5% |
| 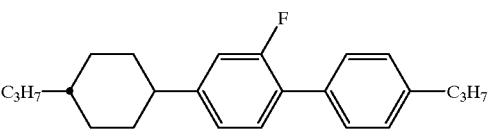 | 4% |
| 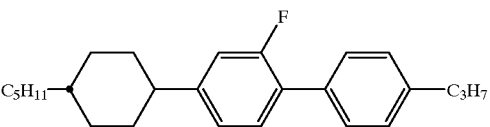 | 4% |
| 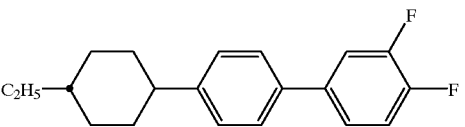 | 5% |
| 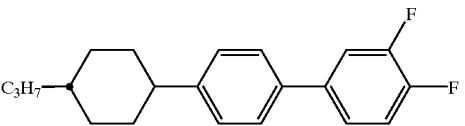 | 5% |
| 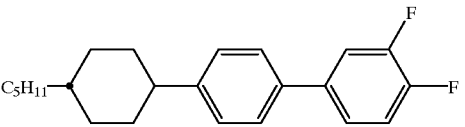 | 10% |

Composition Example 14:
| | | |
|---|---|---|
|  | Compound No. 11 | 5% |
|  | Compound No. 12 | 5% |
| 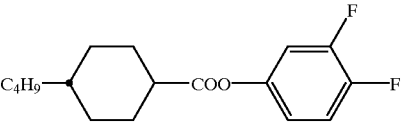 | | 5% |
| 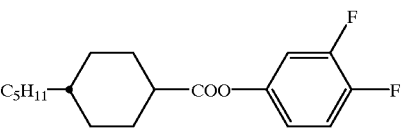 | | 5% |
| 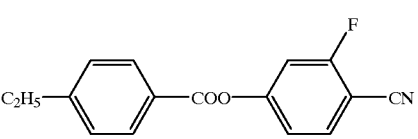 | | 6% |
| 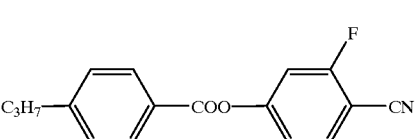 | | 6% |
|  | | 6% |
|  | | 6% |
| 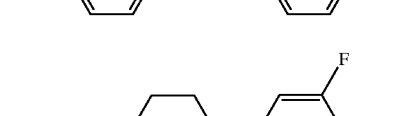 | | 6% |
| 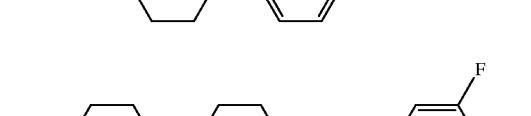 | | 5% |
| 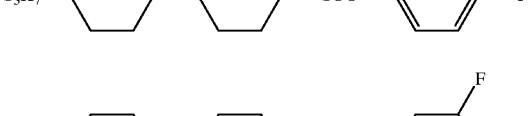 | | 5% |

-continued

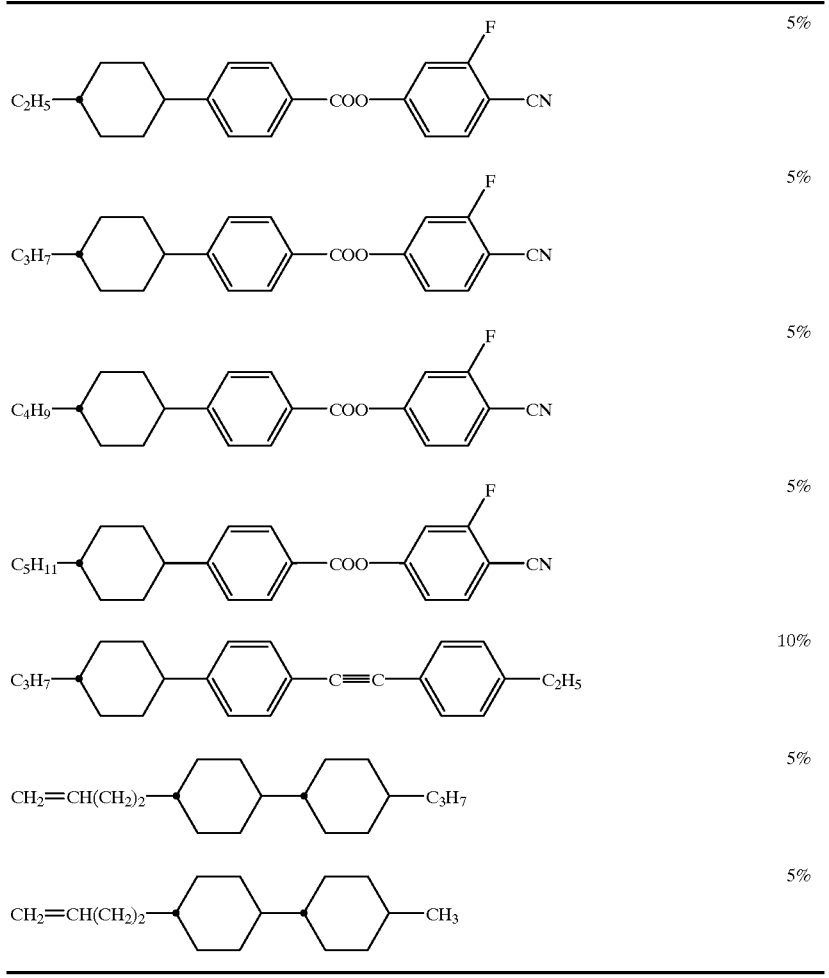

The compound represented by general formula (1) of the present invention can be easily prepared by ordinary organic chemical synthesis methods. For example, methods described in "Organic Synthesis", "Organic Reactions", "Jikken Kagaku Koza (Institute of Experimental Chemistry)", etc. may be properly used in combination to provide an easy synthesis of the compound represented by general formula (1). Details of the above preparation method are described, for example, in Ekishou Device Handbook (Handbook for Liquid Crystal Device), pp. 146–154.

As described above, the compound represented by general formula (1) can be easily synthesized by ordinary organic chemical synthesis methods. For example, the following representative synthesis examples can be used to prepare the compound represented by general formula (1) without problem. In the following reaction scheme, $R_8$ represents an alkyl group, p represents an integer, and R, R', $Z_1$, $Z_2$ and X are as defined above.

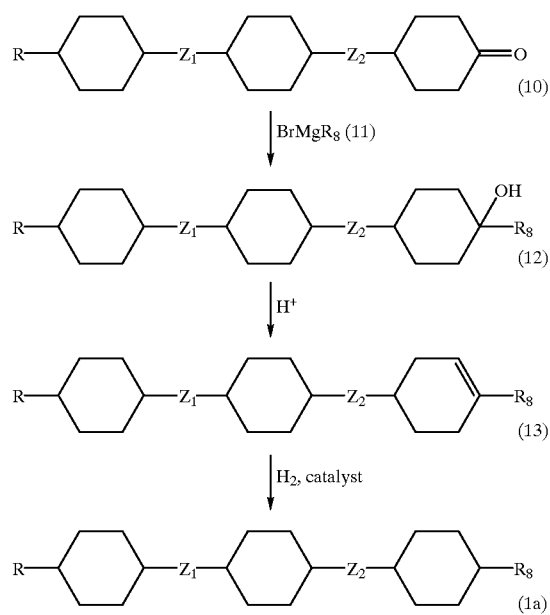

The cyclohexanone compound represented by general formula (10), which can be prepared according to the method described in JP-A-59-7122 (The term "JP-A" as used herein means an "unexamined published Japanese patent application") corresponding to U.S. Pat. No. 4,477,369, can be acted on by a Grignard reagent or corresponding lithium reagent to obtain an alcohol form represented by general formula (12). The cyclohexene derivative represented by general formula (13) obtained by the dehydration reaction of the alcohol form under an acidic condition is then allowed to undergo hydrogenation reaction to prepare the compound represented by general formula (1a). Examples of the acid for use in the dehydration reaction include sulfuric acid, p-toluenesulfonic acid or acidic ion exchange resins. Examples of the catalyst for use in the hydrogenation reaction include an industrial catalyst such as palladium carbon, palladium platinum and Raney nickel catalyst.

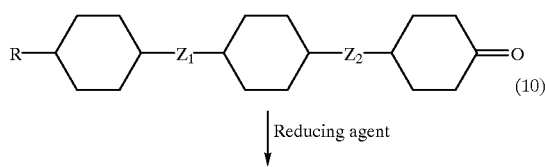

-continued

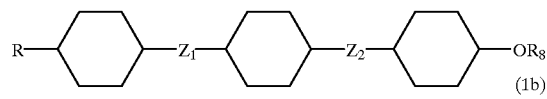

Further, the compound represented by general formula (1) wherein R' is an alkoxy group (represented by the above formula (1b)) can be prepared by a process which comprises reducing the carbonyl group in the cyclohexane compound represented by general formula (10) to give an alcohol form represented by general formula (14), and etherifying the alcohol form under a basic condition. Examples of the reducing agent for use in this synthesis method include ordinary reducing agents such as sodium borohydride and lithium aluminum hydride. The compound (14) can also be obtained by subjecting the compound (10) to the hydrogenation reaction in the presence of the catalyst as described above. The basic condition in the etherification may be made by using a general-purpose basic compound such as sodium hydride, sodium carbonate and potassium carbonate.

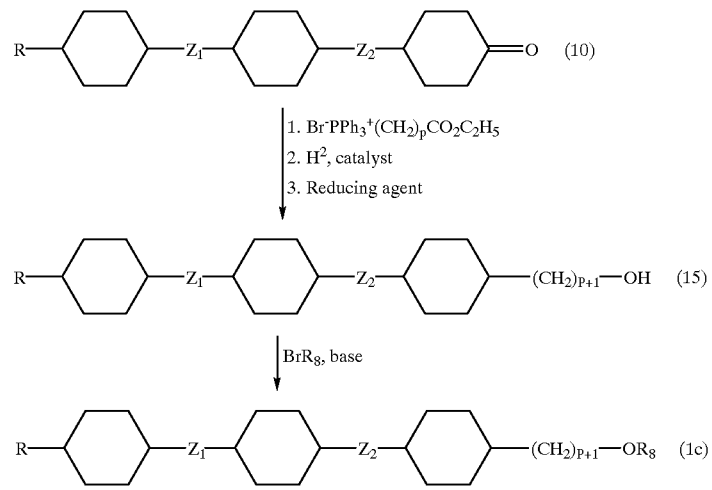

-continued

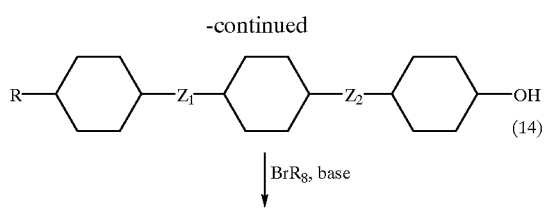

The cyclohexanone compound represented by general formula (10) can be allowed to undergo carbonization reaction in accordance with the method described in Japanese Patent Application No. 6-6629 (corresponding to WO 95/20021) to obtain an alcohol form represented by the general formula (15). The alcohol form can then be acted on by an alkyl halide under the above described basic condition to prepare the compound represented by general formula (1) wherein R' is an alkoxyalkyl group (represented by the above formula (1c)).

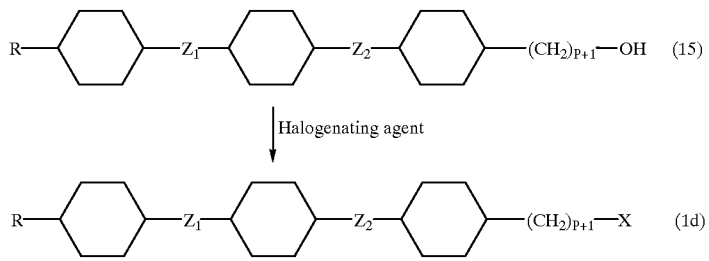

The alcohol form represented by general formula (15) obtained by the above described preparation method can be acted on by various halogenating agents to prepare the compound represented by general formula (1) wherein R' is a halogenated alkyl group (represented by the above formula (1d)). The halogenation may be accomplished by any method. In order to obtain a fluoride, diethylamino sulfur trifluoride (M. Hudlicky, "Organic Reactions", 35, 513 (1988)), diethylamino hexafluoropropene (Ishikawa, "Bulletin of the Chemical Society of Japan", 52 (11), 3377 (1979)), etc. may be preferably used. In order to obtain a chloride, the use of an ordinary chlorinating agent such as thionyl chloride fully meets the purpose.

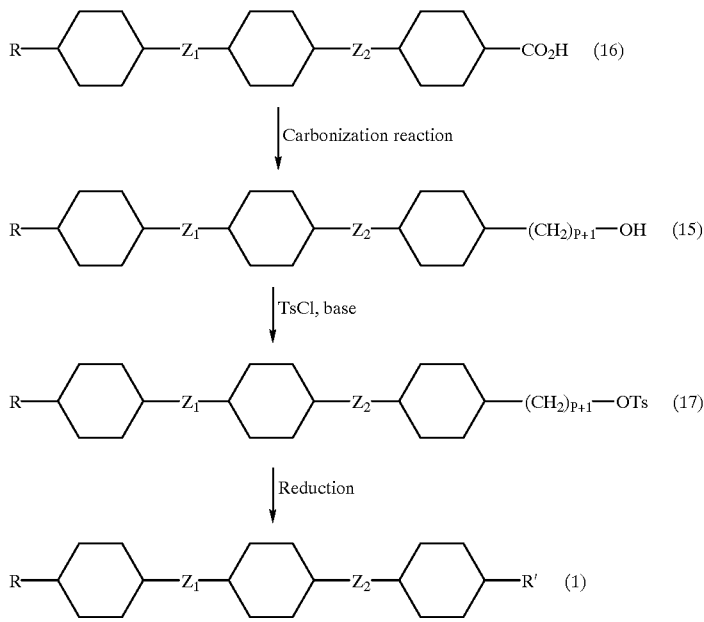

A carboxylic acid or ester thereof described in JP-B-3-20378 may be used instead of the cyclohexanone compound represented by general formula (10) as a starting material. That is, the hydroxyl group in the alcohol form represented by general formula (15) obtained by the carbonization reaction of a carboxylic acid represented by general formula (16) is converted to a leaving group such as tosyl group and halogen (particularly iodine). The resulting compound is then allowed to undergo reductive elimination reaction to prepare the compound represented by general formula (1). Alternatively, the compound represented by general formula (17) can be subjected to the above described halogenation to prepare the compound represented by general formula (1) wherein R' is a halogenated alkyl group.

The process for the preparation of the compound for use in the present invention and the use thereof will be described in detail with reference to the following examples, but the present invention should not be construed as being limited thereto. In the following examples, C, N, S and I represent crystal, nematic phase, smectic phase and isotropic liquid, respectively. The unit of phase transfer temperature is ° C.

EXAMPLE 1

[Preparation of 4-propyl-4"-fluoromethyl-1,1':4',1"-tercyclohexane (compound represented by general formula (1) wherein R represents a propyl group, R' represents a fluoromethyl group, and $Z_1$ and $Z_2$ each represent a covalent bond; Compound No. 48)]

To a mixture of 53.4 mmol of lithium aluminum hydride and 50 ml of tetrahydrofuran (THF) was added dropwise 50 ml of THF solution of 71.2 mmol of 4-propyl-4"-ethoxycarbonyl-1,1':4',1"-tercyclohexane prepared in accordance with the method described in JP-B-3-20378 at a temperature of not higher than 15° C. over 40 minutes. The resulting suspension was stirred at room temperature overnight.

200 ml of ethyl acetate, 100 ml of water and 100 ml of 6 M hydrochloric acid were then successively added to the reaction solution at a temperature kept to not higher than 10° C. A white solid which had been left undissolved was withdrawn by filtration.

The cake thus obtained was thoroughly washed with 6 M hydrochloric acid, water and diethyl ether, and then dried under reduced pressure to obtain 70.1 mmol of 4-propyl-4"-hydroxymethyl-1,1':4',1"-tercyclohexane in the form of colorless crystal.

To a suspension of 37.4 mmol of 4-propyl-4"-hydroxymethyl-1,1':4',1"-tercyclohexane in 140 ml of methylene chloride was then added 74.8 mmol of diethylamino sulfur trifluoride at a temperature of not higher than 10° C. The reaction mixture was then stirred at room temperature overnight.

The reaction solution was then poured into 300 ml of water to separate the methylene chloride phase therefrom. The methylene chloride phase was then concentrated. The residue was subjected to silica gel column chromatography (eluate: heptane), and then recrystallized from a 1:1 mixture of heptane and ethanol so that it was purified to obtain 18.2 mmol of the objective compound. The various spectrum data of the compound thus obtained gave a good proof of its structure. The compound thus obtained assumed a liquid crystal phase and exhibited a (S-I) phase transfer point of 219.6° C.

EXAMPLE 2

[Preparation of 4-propyl-4"-ethyl-1,1':4',1"-tercyclohexane (compound represented by general formula (1) wherein R represents a propyl group, R' represents an ethyl group; and $Z_1$ and $Z_2$ each represent a covalent bond; Compound No. 10)]

To a mixture of 58 mmol of 4-(4-(4-propylcyclohexyl) cyclohexyl)cyclohexanone prepared in accordance with the method described in JP-A-59-7122 (corresponding to U.S. Pat. No. 4,477,369) and 50 ml of THF was added dropwise 90 mmol of THF solution of ethyl magnesium bromide at a temperature of not higher than 10° C. The reaction mixture was then stirred at room temperature for 3 hours.

To the reaction solution was then added 100 ml of 6 M hydrochloric acid. The reaction mixture was then extracted twice with 50 ml of ethyl acetate. The resulting ethyl acetate phase was then separated from the reaction mixture. The solvent was then distilled off the ethyl acetate phase. To the residue were then added 100 ml of toluene and 1 g of p-toluenesulfonic acid monohydrate. The reaction mixture was then heated under reflux while water was being removed for 3 hours.

The reaction system was then allowed to cool. To the reaction solution was then added 100 ml of water. The resulting separated toluene phase was then washed with saturated sodium hydrogencarbonate. The toluene phase thus washed was separated, and then dried over magnesium sulfate anhydride. The solvent was then distilled off the residue to obtain crude 4-(4-(4-propylcyclohexyl) cyclohexyl)-1-ethylcyclohexene. The crude product was then purified through silica gel column chromatography (eluate:heptane) to obtain 49 mmol of 4-(4-(4-propylcyclohexyl)cyclohexyl)-1-ethylcyclohexene.

A mixture of 49 mmol of 4-(4-(4-propylcyclohexyl) cyclohexyl)-1-ethylcyclohexene, 50 ml of ethanol, 100 ml of toluene and 2.5 g of 5% palladium carbon was stirred in an atmosphere of hydrogen for 15 hours. The catalyst used was then removed by filtration. The solvents were then distilled off the reaction solution. The residue was then purified by silica gel column chromatography (eluate:heptane) and subsequently by recrystallization (1:1 mixture of heptane and ethanol) to obtain 21 mmol of the objective compound. The various spectrum data of the compound thus obtained gave a good proof of its structure. The compound thus obtained assumed a liquid crystal phase and exhibited a (S-I) phase transfer point of 223.7° C.

EXAMPLE 3

The following compounds were prepared in accordance with the methods described in Examples 1, 2 or the above described examples of the preparation method. The compounds described in Examples 1 and 2 are also given again below.

Compound No. 1
    4-Methyl-4"-ethyl-1,1':4',1"-tercyclohexane
Compound No. 2
    4-Methyl-4"-propyl-1,1':4',1"-tercyclohexane (S-I transfer point: 207.8° C.)
Compound No. 3
    4-Methyl-4"-butyl-1,1':4',1"-tercyclohexane (S-I transfer point: 244.6° C.)
Compound No. 4
    4-Methyl-4"-pentyl-1,1':4',1"-tercyclohexane
Compound No. 5
    4-Methyl-4"-hexyl-1,1':4',1"-tercyclohexane
Compound No. 6
    4-Methyl-4"-heptyl-1,1':4',1"-tercyclohexane
Compound No. 7
    4-Methyl-4"-octyl-1,1':4',1"-tercyclohexane
Compound No. 8
    4-Methyl-4"-nonyl-1,1':4',1"-tercyclohexane
Compound No. 9
    4-Methyl-4"-decyl-1,1':4',1"-tercyclohexane
Compound No. 10
    4-Ethyl-4"-propyl-1,1':4',1"-tercyclohexane (S-I transfer point: 223.7° C.)
Compound No. 11
    4-Ethyl-4"-butyl-1,1':4',1"-tercyclohexane (S-I transfer point: 240.5° C.)
Compound No. 12
    4-Ethyl-4"-pentyl-1,1':4',1"-tercyclohexane
Compound No. 13
    4-Ethyl-4"-hexyl-1,1':4',1"-tercyclohexane
Compound No. 14
    4-Ethyl-4"-heptyl-1,1':4',1"-tercyclohexane
Compound No. 15
    4-Ethyl-4"-octyl-1,1':4',1"-tercyclohexane
Compound No. 16
    4-Ethyl-4"-nonyl-1,1':4',1"-tercyclohexane
Compound No. 17
    4-Ethyl-4"-decyl-1,1':4',1"-tercyclohexane
Compound No. 18
    4-Propyl-4"-butyl-1,1':4',1"-tercyclohexane
Compound No. 19
    4-Propyl-4"-pentyl-1,1':4',1"-tercyclohexane
Compound No. 20
    4-Propyl-4"-hexyl-1,1':4',1"-tercyclohexane
Compound No. 21
    4-Propyl-4"-heptyl-1,1':4',1"-tercyclohexane
Compound No. 22
    4-Propyl-4"-octyl-1,1':4',1"-tercyclohexane
Compound No. 23
    4-Propyl-4"-nonyl-1,1':4',1"-tercyclohexane
Compound No. 24
    4-Propyl-4"-decyl-1,1':4',1"-tercyclohexane
Compound No. 25
    4-Butyl-4"-pentyl-1,1':4',1"-tercyclohexane (S-I transfer point: 243.8° C.)
Compound No. 26
    4-Butyl-4"-hexyl-1,1':4',1"-tercyclohexane
Compound No. 27
    4-Butyl-4"-heptyl-1,1':4',1"-tercyclohexane
Compound No. 28
    4-Butyl-4"-octyl-1,1':4',1"-tercyclohexane Compound No. 29
4-Butyl-4"-nonyl-1,1':4',1"-tercyclohexane
Compound No. 30
4-Butyl-4"-decyl-1,1':4',1"-tercyclohexane
Compound No. 31
4-Pentyl-4"-hexyl-1,1':4',1"-tercyclohexane
Compound No. 32
4-Pentyl-4"-heptyl-1,1':4',1"-tercyclohexane
Compound No. 33
4-Pentyl-4"-octyl-1,1':4',1"-tercyclohexane
Compound No. 34
4-Pentyl-4"-nonyl-1,1':4',1"-tercyclohexane (S-I transfer point: 252.6° C.)
Compound No. 35
4-Pentyl-4"-decyl-1,1':4',1"-tercyclohexane
Compound No. 36
4-Hexyl-4"-heptyl-1,1':4',1"-tercyclohexane
Compound No. 37
4-Hexyl-4"-octyl-1,1':4',1"-tercyclohexane
Compound No. 38
4-Hexyl-4"-nonyl-1,1':4',1"-tercyclohexane
Compound No. 39
4-Hexyl-4"-decyl-1,1':4',1"-tercyclohexane
Compound No. 40
4-Heptyl-4"-octyl-1,1':4',1"-tercyclohexane
Compound No. 41
4-Heptyl-4"-nonyl-1,1':4',1"-tercyclohexane
Compound No. 42
4-Heptyl-4"-decyl-1,1':4',1"-tercyclohexane
Compound No. 43
4-Octyl-4"-nonyl-1,1':4',1"-tercyclohexane
Compound No. 44
4-Octyl-4"-decyl-1,1':4',1"-tercyclohexane
Compound No. 45
4-Nonyl-4"-decyl-1,1':4',1"-tercyclohexane
Compound No. 46
4-Fluoromethyl-4"-methyl-1,1':4',1"-tercyclohexane
Compound No. 47
4-Fluoromethyl-4"-ethyl-1,1':4',1"-tercyclohexane
Compound No. 48
4-Fluoromethyl-4"-propyl-1,1':4',1"-tercyclohexane (S-I transfer point: 219.6° C.)
Compound No. 49
4-Fluoromethyl-4"-butyl-1,1':4',1"-tercyclohexane
Compound No. 50
4-Fluoromethyl-4"-pentyl-1,1':4',1"-tercyclohexane
Compound No. 51
4-Fluoromethyl-4"-hexyl-1,1':4',1"-tercyclohexane
Compound No. 52
4-Fluoromethyl-4"-heptyl-1,1':4',1"-tercyclohexane
Compound No. 53
4-Fluoromethyl-4"-octyl-1,1':4',1"-tercyclohexane
Compound No. 54
4-Fluoromethyl-4"-nonyl-1,1':4',1"-tercyclohexane
Compound No. 55
4-Fluoromethyl-4"-decyl-1,1':4',1"-tercyclohexane
Compound No. 56
4-(2-Fluoroethyl)-4"-ethyl-1,1':4',1"-tercyclohexane
Compound No. 57
4-(2-Fluoroethyl)-4"-propyl-1,1':4',1"-tercyclohexane
Compound No. 58
4-(2-Fluoroethyl)-4"-butyl-1,1':4',1"-tercyclohexane
Compound No. 59
4-(2-Fluoroethyl)-4"-pentyl-1,1':4',1"-tercyclohexane (S-I transfer point: 252.5° C.)
Compound No. 60
4-(2-Fluoroethyl)-4"-hexyl-1,1':4',1"-tercyclohexane
Compound No. 61
4-(2-Fluoroethyl)-4"-heptyl-1,1':4',1"-tercyclohexane
Compound No. 62
4-(2-Fluoroethyl)-4"-octyl-1,1':4',1"-tercyclohexane
Compound No. 63
4-(2-Fluoroethyl)-4"-nonyl-1,1':4',1"-tercyclohexane
Compound No. 64
4-(2-Fluoroethyl)-4"-decyl-1,1':4',1"-tercyclohexane
Compound No. 65
4-(3-Fluoropropyl)-4"-propyl-1,1':4',1"-tercyclohexane
Compound No. 66
4-(3-Fluoropropyl)-4"-butyl-1,1':4',1"-tercyclohexane
Compound No. 67
4-(3-Fluoropropyl)-4"-pentyl-1,1':4',1"-tercyclohexane
Compound No. 68
4-(3-Fluoropropyl)-4"-hexyl-1,1':4',1"-tercyclohexane
Compound No. 69
4-(3-Fluoropropyl)-4"-heptyl-1,1':4',1"-tercyclohexane
Compound No. 70
4-(3-Fluoropropyl)-4"-octyl-1,1':4',1"-tercyclohexane
Compound No. 71
4-(3-Fluoropropyl)-4"-nonyl-1,1':4',1"-tercyclohexane
Compound No. 72
4-(3-Fluoropropyl)-4"-decyl-1,1':4',1"-tercyclohexane
Compound No. 73
4-(4-Fluorobutyl)-4"-butyl-1,1':4',1"-tercyclohexane
Compound No. 74
4-(4-Fluorobutyl)-4"-pentyl-1,1':4',1"-tercyclohexane (S-I transfer point: 255.7° C.)
Compound No. 75
4-(4-Fluorobutyl)-4"-hexyl-1,1':4',1"-tercyclohexane
Compound No. 76
4-(4-Fluorobutyl)-4"-heptyl-1,1':4',1"-tercyclohexane
Compound No. 77
4-(4-Fluorobutyl)-4"-octyl-1,1':4',1"-tercyclohexane
Compound No. 78
4-(4-Fluorobutyl)-4"-nonyl-1,1':4',1"-tercyclohexane
Compound No. 79
4-(4-Fluorobutyl)-4"-decyl-1,1':4',1"-tercyclohexane
Compound No. 80
4-(5-Fluoropentyl)-4"-pentyl-1,1':4',1"-tercyclohexane
Compound No. 81
4-(5-Fluoropentyl)-4"-hexyl-1,1':4',1"-tercyclohexane (S-I transfer point: 268.3° C.)
Compound No. 82
4-(5-Fluoropentyl)-4"-heptyl-1,1':4',1"-tercyclohexane
Compound No. 83
4-(5-Fluoropentyl)-4"-octyl-1,1':4',1"-tercyclohexane
Compound No. 84
4-(5-Fluoropentyl)-4"-nonyl-1,1':4',1"-tercyclohexane
Compound No. 85
4-(5-Fluoropentyl)-4"-decyl-1,1':4',1"-tercyclohexane
Compound No. 86
4-(6-Fluorohexyl)-4"-hexyl-1,1':4',1"-tercyclohexane
Compound No. 87
4-(6-Fluorohexyl)-4"-heptyl-1,1':4',1"-tercyclohexane
Compound No. 88
4-(6-Fluorohexyl)-4"-octyl-1,1':4',1"-tercyclohexane
Compound No. 89
4-(6-Fluorohexyl)-4"-nonyl-1,1':4',1"-tercyclohexane
Compound No. 90
4-(6-Fluorohexyl)-4"-decyl-1,1':4',1"-tercyclohexane
Compound No. 91
4-(6-Fluorohexyl)-4"-heptyl-1,1':4',1"-tercyclohexane
Compound No. 92
4-(7-Fluoroheptyl)-4"-octyl-1,1':4',1"-tercyclohexane
Compound No. 93

4-(7-Fluoroheptyl)-4"-nonyl-1,1':4',1"-tercyclohexane
Compound No. 94
4-(7-Fluoroheptyl)-4"-decyl-1,1':4',1"-tercyclohexane
Compound No. 95
4-(8-Fluorooctyl)-4"-octyl-1,1':4',1"-tercyclohexane
Compound No. 96
4-(8-Fluorooctyl)-4"-nonyl-1,1':4',1"-tercyclohexane
Compound No. 97
4-(8-Fluorooctyl)-4"-decyl-1,1':4',1"-tercyclohexane
Compound No. 98
4-(9-Fluorononyl)-4"-nonyl-1,1':4',1"-tercyclohexane
Compound No. 99
4-(9-Fluorononyl)-4"-decyl-1,1':4',1"-tercyclohexane
Compound No. 100
4-(10-Fluorodecyl)-4"-decyl-1,1':4',1"-tercyclohexane
Compound No. 101
4-Fluoromethyl-4"-fluoromethyl-1,1':4',1"-tercyclohexane
Compound No. 102
4-Fluoromethyl-4"-(2-fluoroethyl)-1,1':4',1"-tercyclohexane
Compound No. 103
4-Fluoromethyl-4"-(3-fluoropropyl)-1,1':4',1"-tercyclohexane
Compound No. 104
4-Fluoromethyl-4"-(4-fluorobutyl)-1,1':4',1"-tercyclohexane
Compound No. 105
4-Fluoromethyl-4"-(5-fluoropentyl)-1,1':4',1"-tercyclohexane
Compound No. 106
4-Fluoromethyl-4"-(6-fluorohexyl)-1,1':4',1"-tercyclohexane
Compound No. 107
4-Fluoromethyl-4"-(7-fluoroheptyl)-1,1':4',1"-tercyclohexane
Compound No. 108
4-Fluoromethyl-4"-(8-fluorooctyl)-1,1':4',1"-tercyclohexane
Compound No. 109
4-Fluoromethyl-4"-(4-fluorononyl)-1,1':4',1"-tercyclohexane
Compound No. 110
4-Fluoromethyl-4"-(10-fluorodecyl)-1,1':4',1"-tercyclohexane
Compound No. 111
4-(2-Fluoroethyl)-4"-(2-fluoroethyl)-1,1':4',1"-tercyclohexane
Compound No. 112
4-(2-Fluoroethyl)-4"-(3-fluoropropyl)-1,1':4',1"-tercyclohexane (S-I transfer point: 243.7° C.)
Compound No. 113
4-(2-Fluoroethyl)-4"-(4-fluorobutyl)-1,1':4',1"-tercyclohexane
Compound No. 114
4-(2-Fluoroethyl)-4"-(5-fluoropentyl)-1,1':4',1"-tercyclohexane
Compound No. 115
4-(2-Fluoroethyl)-4"-(6-fluorohexyl)-1,1':4',1"-tercyclohexane
Compound No. 116
4-(2-Fluoroethyl)-4"-(7-fluoroheptyl)-1,1':4',1"-tercyclohexane
Compound No. 117
4-(2-Fluoroethyl)-4"-(8-fluorooctyl)-1,1':4',1"-tercyclohexane
Compound No. 118
4-(2-Fluoroethyl)-4"-(9-fluorononyl)-1,1':4',1"-tercyclohexane
Compound No. 119
4-(2-Fluoroethyl)-4"-(10-fluorodecyl)-1,1':4',1"-tercyclohexane
Compound No. 120
4-(3-Fluoropropyl)-4"-(3-fluoroproyl)-1,1':4',1"-tercyclohexane
Compound No. 121
4-(3-Fluoropropyl)-4"-(4-fluorobutyl)-1,1':4',1"-tercyclohexane
Compound No. 122
4-(3-Fluoropropyl)-4"-(5-fluoropentyl)-1,1':4',1"-tercyclohexane
Compound No. 123
4-(3-Fluoropropyl)-4"-(6-fluorohexyl)-1,1':4',1"-tercyclohexane
Compound No. 124
4-(3-Fluoropropyl)-4"-(7-fluoroheptyl)-1,1':4',1"-tercyclohexane
Compound No. 125
4-(3-Fluoropropyl)-4"-(8-fluorooctyl)-1,1':4',1"-tercyclohexane
Compound No. 126
4-(3-Fluoropropyl)-4"-(9-fluorononyl)-1,1':4',1"-tercyclohexane
Compound No. 127
4-(3-Fluoropropyl)-4"-(10-fluorodecyl)-1,1':4',1"-tercyclohexane
Compound No. 128
4-(4-Fluorobutyl)-4"-(4-fluorobutyl)-1,1':4',1"-tercyclohexane
Compound No. 129
4-(4-Fluorobutyl)-4"-(5-fluoropentyl)-1,1':4',1"-tercyclohexane
Compound No. 130
4-(4-Fluorobutyl)-4"-(6-fluorohexyl)-1,1':4',1"-tercyclohexane
Compound No. 131
4-(4-Fluorobutyl)-4"-(7-fluoroheptyl)-1,1':4',1"-tercyclohexane
Compound No. 132
4-(4-Fluorobutyl)-4"-(8-fluorooctyl)-1,1':4',1"-tercyclohexane
Compound No. 133
4-(4-Fluorobutyl)-4"-(9-fluorononyl)-1,1':4',1"-tercyclohexane
Compound No. 134
4-(4-Fluorobutyl)-4"-(10-fluorodecyl)-1,1':4',1"-tercyclohexane
Compound No. 135
4-(5-Fluoropentyl)-4"-(5-fluoropentyl)-1,1':4',1"-tercyclohexane
Compound No. 136
4-(5-Fluoropentyl)-4"-(6-fluorohexyl)-1,1':4',1"-tercyclohexane
Compound No. 137
4-(5-Fluoropentyl)-4"-(7-fluoroheptyl)-1,1':4',1"-tercyclohexane
Compound No. 138
4-(5-Fluoropentyl)-4"-(8-fluorooctyl)-1,1':4',1"-tercyclohexane
Compound No. 139
4-(5-Fluoropentyl)-4"-(9-fluorononyl)-1,1':4',1"-tercyclohexane
Compound No. 140
4-(5-Fluoropentyl)-4"-(10-fluorodecyl)-1,1':4',1"-tercyclohexane Compound No. 141
  4-(6-Fluorohexyl)-4"-(6-fluorohexyl)-1,1':4',1"-tercyclohexane
Compound No. 142
  4-(6-Fluorohexyl)-4"-(7-fluoroheptyl)-1,1':4',1"-tercyclohexane
Compound No. 143
  4-(6-Fluorohexyl)-4"-(8-fluorooctyl)-1,1':4',1"-tercyclohexane
Compound No. 144
  4-(6-Fluorohexyl)-4"-(9-fluorononyl)-1,1':4',1"-tercyclohexane
Compound No. 145
  4-(6-Fluorohexyl)-4"-(10-fluorodecyl)-1,1':4',1"-tercyclohexane
Compound No. 146
  4-(6-Fluorohexyl)-4"-(7-fluoroheptyl)-1,1':4',1"-tercyclohexane
Compound No. 147
  4-(7-Fluoroheptyl)-4"-(8-fluorooctyl)-1,1':4',1"-tercyclohexane
Compound No. 148
  4-(7-Fluoroheptyl)-4"-(9-fluorononyl)-1,1':4',1"-tercyclohexane
Compound No. 149
  4-(7-Fluoroheptyl)-4"-(10-fluorodecyl)-1,1':4',1"-tercyclohexane
Compound No. 150
  4-(8-Fluorooctyl)-4"-(8-fluorooctyl)-1,1':4',1"-tercyclohexane
Compound No. 151
  4-(8-Fluorooctyl)-4"-(9-fluorononyl)-1,1':4',1"-tercyclohexane
Compound No. 152
  4-(8-Fluorooctyl)-4"-(10-fluorodecyl)-1,1':4',1"-tercyclohexane
Compound No. 153
  4-(9-Fluorononyl)-4"-(9-fluorononyl)-1,1':4',1"-tercyclohexane
Compound No. 154
  4-(9-Fluorononyl)-4"-(10-fluorodecyl)-1,1':4',1"-tercyclohexane
Compound No. 155
  4-(10-Fluorodecyl)-4"-(10-fluorodecyl)-1,1':4',1"-tercyclohexane
Compound No. 156
  4-(4-(2-(4-Propylcyclohexyl)ethyl)cyclohexyl)-1-propylcyclohexane
Compound No. 157
  4-(4-(2-(4-Propylcyclohexyl)ethyl)cyclohexyl)-1-butylcyclohexane
Compound No. 158
  4-(4-(2-(4-Propylcyclohexyl)ethyl)cyclohexyl)-1-pentylcyclohexane
Compound No. 159
  4-(4-(2-(4-Propylcyclohexyl)ethyl)cyclohexyl)-1-hexylcyclohexane
Compound No. 160
  4-(4-(2-(4-Propylcyclohexyl)ethyl)cyclohexyl)-1-nonylcyclohexane
Compound No. 161
  4-(4-(2-(4-Butylcyclohexyl)ethyl)cyclohexyl)-1-propylcyclohexane
Compound No. 162
  4-(4-(2-(4-Butylcyclohexyl)ethyl)cyclohexyl)-1-pentylcyclohexane
Compound No. 163
  4-(4-(2-(4-Butylcyclohexyl)ethyl)cyclohexyl)-1-heptylcyclohexane
Compound No. 164
  4-(4-(2-(4-Pentylcyclohexyl)ethyl)cyclohexyl)-1-ethylcyclohexane
Compound No. 165
  4-(4-(2-(4-Pentylcyclohexyl)ethyl)cyclohexyl)-1-propylcyclohexane
Compound No. 166
  4-(4-(2-(4-Pentylcyclohexyl)ethyl)cyclohexyl)-1-pentylcyclohexane
Compound No. 167
  4-(4-(2-(4-Pentylcyclohexyl)ethyl)cyclohexyl)-1-octylcyclohexane
Compound No. 168
  4-(4-(2-(4-Hexylcyclohexyl)ethyl)cyclohexyl)-1-methylcyclohexane
Compound No. 169
  4-(4-(2-(4-Hexylcyclohexyl)ethyl)cyclohexyl)-1-propylcyclohexane
Compound No. 170
  4-(4-(2-(4-Hexylcyclohexyl)ethyl)cyclohexyl)-1-pentylcyclohexane
Compound No. 171
  4-(4-(2-(4-Hexylcyclohexyl)ethyl)cyclohexyl)-1-octylcyclohexane
Compound No. 172
  4-(4-(2-(4-Heptylcyclohexyl)ethyl)cyclohexyl)-1-ethylcyclohexane
Compound No. 173
  4-(4-(2-(4-Heptylcyclohexyl)ethyl)cyclohexyl)-1-propylcyclohexane
Compound No. 174
  4-(4-(2-(4-Heptylcyclohexyl)ethyl)cyclohexyl)-1-pentylcyclohexane
Compound No. 175
  4-(4-(2-(4-Octylcyclohexyl)ethyl)cyclohexyl)-1-pentylcyclohexane
Compound No. 176
  4-(4-(2-(4-Nonylcyclohexyl)ethyl)cyclohexyl)-1-nonylcyclohexane
Compound No. 177
  4-(4-(2-(4-Decylcyclohexyl)ethyl)cyclohexyl)-1-pentylcyclohexane
Compound No. 178
  4-(4-(2-(4-(3-Fluoropropyl)cyclohexyl)ethyl)cyclohexyl)-1-propylcyclohexane
Compound No. 179
  4-(4-(2-(4-Propylcyclohexyl)ethyl)cyclohexyl)-1-(4-fluorobutyl)cyclohexane
Compound No. 180
  4-(4-(2-(4-(3-Fluoropropyl)cyclohexyl)ethyl)cyclohexyl)-1-(5-fluoropentyl)cyclohexane
Compound No. 181
  4-(4-(2-(4-(3-Fluoropropyl)cyclohexyl)ethyl)cyclohexyl)-1-hexylcyclohexane
Compound No. 182
  4-(4-(2-(4-(3-Fluoropropyl)cyclohexyl)ethyl)cyclohexyl)-1-nonylcyclohexane
Compound No. 183
  4-(4-(2-(4-Butylcyclohexyl)ethyl)cyclohexyl)-1-(3-fluoropropyl)cyclohexane
Compound No. 184
  4-(4-(2-(4-(4-Fluorobutyl)cyclohexyl)ethyl)cyclohexyl)-1-(5-fluoropentyl)cyclohexane
Compound No. 185
  4-(4-(2-(4-(3-Fluorobutyl)cyclohexyl)ethyl)cyclohexyl)-1-heptylcyclohexane Compound No. 186
4-(4-(2-(4-Pentylcyclohexyl)ethyl)cyclohexyl)-1-(2-fluoroethyl)cyclohexane
Compound No. 187
4-(4-(2-(4-Pentylcyclohexyl)ethyl)cyclohexyl)-1-(3-fluoropropyl)cyclohexane
Compound No. 188
4-(4-(2-(4-(5-Fluoropentyl)cyclohexyl)ethyl)cyclohexyl)-1-pentylcyclohexane
Compound No. 189
4-(4-(2-(4-(5-Fluoropentyl)cyclohexyl)ethyl)cyclohexyl)-1-octylcyclohexane
Compound No. 190
4-(4-(2-(4-Hexylcyclohexyl)ethyl)cyclohexyl)-1-fluoromethylcyclohexane
Compound No. 191
4-(4-(2-(4-Hexylcyclohexyl)ethyl)cyclohexyl)-1-(3-fluoropropyl)cyclohexane
Compound No. 192
4-(4-(2-(4-(6-Fluorohexyl)cyclohexyl)ethyl)cyclohexyl)-1-(5-fluoropentyl)cyclohexane
Compound No. 193
4-(4-(2-(4-(6-Fluorohexyl)cyclohexyl)ethyl)cyclohexyl)-1-octylcyclohexane
Compound No. 194
4-(4-(2-(4-Heptylcyclohexyl)ethyl)cyclohexyl)-1-(2-fluoroethyl)cyclohexane
Compound No. 195
4-(4-(2-(4-Heptylcyclohexyl)ethyl)cyclohexyl)-1-(3-fluoropropyl)cyclohexane
Compound No. 196
4-(4-(2-(4-Heptylcyclohexyl)ethyl)cyclohexyl)-1-(5-fluoropentyl)cyclohexane
Compound No. 197
4-(4-(2-(4-(10-Fluorodecyl)cyclohexyl)ethyl)cyclohexyl)-1-(5-fluoropentyl)cyclohexane
Compound No. 198
4-(2-(4-(2-(4-Propylcyclohexyl)ethyl)cyclohexyl)ethyl-1-propylcyclohexane
Compound No. 199
4-(2-(4-(2-(4-Propylcyclohexyl)ethyl)cyclohexyl)ethyl-1-pentylcyclohexane
Compound No. 200
4-(2-(4-(2-(4-Butylcyclohexyl)ethyl)cyclohexyl)ethyl-1-pentylcyclohexane
Compound No. 201
4-(2-(4-(2-(4-Pentylcyclohexyl)ethyl)cyclohexyl)ethyl-1-pentylcyclohexane
Compound No. 202
4-(2-(4-(2-(4-Pentylcyclohexyl)ethyl)cyclohexyl)ethyl-1-hexylcyclohexane
Compound No. 203
4-(2-(4-(2-(4-Hexylcyclohexyl)ethyl)cyclohexyl)ethyl-1-hexylcyclohexane
Compound No. 204
4-(2-(4-(2-(4-Hexylcyclohexyl)ethyl)cyclohexyl)ethyl-1-octylcyclohexane
Compound No. 205
4-(2-(4-(2-(4-Octylcyclohexyl)ethyl)cyclohexyl)ethyl-1-decylcyclohexane
Compound No. 206
4-(2-(4-(2-(4-(3-Fluoropropyl)cyclohexyl)ethyl)cyclohexyl)ethyl-1-propylcyclohexane
Compound No. 207
4-(2-(4-(2-(4-(3-Fluoropropyl)cyclohexyl)ethyl)cyclohexyl)ethyl-1-pentylcyclohexane
Compound No. 208
4-(2-(4-(2-(4-Butylcyclohexyl)ethyl)cyclohexyl)ethyl-1-(5-fluoropentyl)cyclohexane
Compound No. 209
4-(2-(4-(2-(4-(5-Fluoropentyl)cyclohexyl)ethyl)cyclohexyl)ethyl-1-(5-fluoropentyl)cyclohexane
Compound No. 210
4-(2-(4-(2-(4-(5-Fluoropentyl)cyclohexyl)ethyl)cyclohexyl)ethyl-1-hexylcyclohexane
Compound No. 211
4-(2-(4-(2-(4-(6-Chlorohexyl)cyclohexyl)ethyl)cyclohexyl)ethyl-1-hexylcyclohexane
Compound No. 212
4-(2-(4-(2-(4-(6-Fluorohexyl)cyclohexyl)ethyl)cyclohexyl)ethyl-1-octylcyclohexane
Compound No. 213
4-(2-(4-(2-(4-(8-Fluorooctyl)cyclohexyl)ethyl)cyclohexyl)ethyl-1-decylcyclohexane

EXAMPLE 4 (USAGE EXAMPLE 1)

A liquid crystal composition B, comprising 24% of 4-(4-propylcyclohexyl)benzonitrile, 36% of 4-(4-pentylcyclohexyl)benzonitrile, 25% of 4-(4-heptylcyclohexyl) benzonitrile and 15% of 4-(4-4-pentylcyclohexyl)phenyl) benzonitrile was prepared. This nematic liquid crystal exhibited a clearing point of 72.4° C., a threshold voltage of 1.78 V as determined with a cell thickness of 9 μm, a dielectric anisotropy value of 11.0, a refractive index anisotropy value of 0.137 and a viscosity of 27.0 mPaS at 20° C.

95% of $B_1$ and 5% of 4-propyl-4"-ethyl-1,1':4',1"-tercyclohexane (Compound No. 10), which had been obtained as a compound of the present invention in Example 2, were mixed to prepare a liquid crystal composition $A_1$. $A_1$ exhibited a clearing point of 77.6° C., a threshold voltage of 1.82 V as determined with a cell thickness of 8.7 μm, a dielectric anisotropy value of 10.4, a refractive index anisotropy value of 0.135 and a viscosity of 26.6 mPaS at 20° C. From these results were calculated extrapolated clearing point, extrapolated refractive index anisotropy value and extrapolated viscosity as follows:

Extrapolated clearing point: 189.7° C.
Extrapolated refractive index anisotropy value: 0.087
Extrapolated viscosity: 20.4 mPas The composition thus obtained was then allowed to stand in a −20° C. freezer for 60 days. As a result, neither crystal nor smectic phase was deposited. $A_1$ was also measured for voltage holding ratio. The result was 99.8% at 100° C.

Comparative Example 1

The above described comparative Compounds 1 and 2 were prepared in accordance with the method described in JP-B-62-39136 (corresponding to U.S. Pat. No. 4,422,951). These comparative compounds exhibited the following phase transfer temperatures:
Comparative Compound 1:
  C-S transfer point: 20.9° C.,
  S-I transfer point: 177.5° C.
Comparative Compound 2:
  C-S transfer point: 79.6° C.,
  S-N transfer point: 128.9° C.,
  S-N transfer point: 203.2° C.

95% of $B_1$ was then mixed with 5% of comparative Compounds 1 and 2 to obtain liquid crystal compositions $A_2$ and $A_3$, respectively. The extrapolated clearing point, extrapolated refractive index anisotropy value and extrapolated viscosity of these liquid crystal compositions were as follows:

Comparative Compound 1:
 Extrapolated clearing point: 130.1° C.
 Extrapolated refractive index anisotropy value: 0.126
 Extrapolated viscosity: 27.1 mPaS
Comparative Compound 2:
 Extrapolated clearing point: 174.8° C.
 Extrapolated refractive index anisotropy value: 0.132
 Extrapolated viscosity: 36.1 mPaS Comparative Example 2

The above described comparative Compound 3 was prepared in accordance with the method described in JP-B-63-10137. The comparative compound exhibited C-S transfer point of 20.7° C. and S-I transfer point of 95.2° C.

95% of $B_1$ was then mixed with 5% of comparative Compound 3 to obtain a liquid crystal composition $A_4$. The liquid crystal composition $A_4$ exhibited an extrapolated clearing point of 60.8° C., an extrapolated refractive index anisotropy value of 0.032 and an extrapolated viscosity of −15.9 mPaS.

Comparative Example 3

4-Butyl-4'-butyl-1,1':4',1"-tercyclohexane was prepared in accordance with the method described in J. de Physique, 36, 379 (1975). 95% of $B_1$ was mixed with 5% of this compound to obtain a liquid crystal composition $A_5$. The liquid crystal composition $A_5$ was allowed to stand in a −20° C. freezer. On the third days, a smectic phase appeared.

EXAMPLE 5 (USAGE EXAMPLE 2)

A liquid crystal composition having the following formulation was prepared. The structure of the various compounds used in the following examples are shown in accordance with the abbreviation set forth in Table 1.

TABLE 1

Symbolizing Metod of compounds
R—($A_1$)—$Z_1$————————$Z_n$—($A_n$)——X

| 1) Left Terminal R— | Symbol | 3) Linkage —$Z_1$—,—$Z_2$— | Symbol |
|---|---|---|---|
| $C_nH_{2n+1}$— | n— | —$C_2H_4$— | 2 |
| $C_nH_{2n+1}O$— | nO— | —$C_4H_8$— | 4 |
| $C_nH_{2n+1}OC_mH_{2m}$— | nOm— | —COO— | E |
| $CH_2$=CH— | V— | —C≡C— | T |
| $CH_2$=$CHC_nH_{2n}$— | Vn— | —CH=CH— | V |
| $C_nH_{2n+1}CH$=$CHC_mH_{2m}$— | nVm— | —$CF_2O$— | CF2O |
| $C_nH_{2n+1}CH$=$CHC_mH_{2m}CH$=$CHC_kH_{2k}$— | nVmVk— | —$OCF_2$— | OCF2 |
| $C_nH_{2n+1}CC_mH_{2m}$—<br>‖<br>$CH_2$ | nVem— | | |

| 2) Ring Structure —($A_1$)——, —($A_n$)—— | Symbol | 4) Right Terminal —X | Symbol |
|---|---|---|---|
| 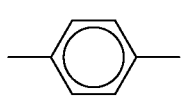 | B | —F | —F |
| 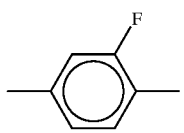 | B(F) | —Cl | —CL |
| 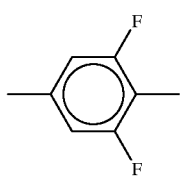 | B(F,F) | —CN | —C |
|  | H | —$CF_3$ | —CF3 |
| 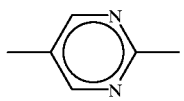 | Py | —$OCF_3$ | —OCF3 |

TABLE 1-continued

Symbolizing Metod of compounds
R—(A₁)—Z₁————————Z_n—(A_n)——X

| Structure | Symbol | Group | X symbol |
|---|---|---|---|
| (1,3-dioxane ring) | D | —OCF₂H | —OCF2H |
| (cyclohexene ring) | Ch | —C_nH_{2n+1} | —n |
| | | —OC_nH_{2n+1} | —On |
| | | —COOCH₃ | —EMe |
| | | —C_nH_{2n}CH=CH₂ | —nV |
| | | —C_mH_{2m}CH=CHC_nH_{2n+1} | —mVn |
| | | —C_mH_{2m}CH=CHC_nH_{2n}F | —mVnF |
| | | —CH=CF₂ | —VFF |

5) Symbolizing Examples ex. 1   3-H2B(F,F)B(F)—F

C₃H₇—(cyclohexyl)—C₂H₄—(2,6-difluorophenyl)—(3,4-difluorophenyl)—F ex. 2   3-HB(F)TB-2

C₃H₇—(cyclohexyl)—(3-fluorophenyl)—C≡C—(phenyl)—C₂H₅ ex. 3   1V2-BEB(F,F)—C

CH₃CH=CHCH₂CH₂—(phenyl)—COO—(3,5-difluorophenyl)—CN

| Composition: | |
|---|---|
| 2-HHH-3 (Compound No. 10) | 3.0% |
| 2-HHH-4 (Compound No. 11) | 2.0% |
| 1V2-BEB (F, F)-C | 5.0% |
| 3-HB-C | 25.0% |
| 1-BTB-3 | 5.0% |
| 2-BTB-1 | 10.0% |
| 3-HH-4 | 11.0% |
| 3-HHB-1 | 11.0% |
| 3-HHB-3 | 4.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

The above described composition exhibited the following physical properties. In this and the following Examples, the viscosity ($\eta$) was measured at a temperature of 20° C., and the refractive index anisotropy ($\Delta n$), dielectric anisotropy ($\Delta \epsilon$), threshold voltage ($V_{th}$) and twist pitch (P) were each measured at a temperature of 25.0° C.

P was measured when a chiral material (Cholesteryl Nonanoate) having an asymmetric carbon atom was added in an amount of 2.0 parts based on the total amount (100 parts) of the composition.

Physical properties: $T_{N-I}$=90.6° C.

$\eta$=15.7 mpa·s $\Delta n$=0.160

$\Delta \epsilon$=7.1

$V_{th}$=2.10 V

P=11.3 $\mu$m

EXAMPLE 6 (USAGE EXAMPLE 3)

| Composition: | | |
|---|---|---:|
| | 1-HHH-3 (Compound No. 2) | 2.0% |
| | 2-HHH-3 (Compound No. 10) | 2.0% |
| | V2-HB-C | 12.0% |
| | 1V2-HB-C | 12.0% |
| | 3-HB-C | 24.0% |
| | 3-HB(F)-C | 5.0% |
| | 2-BTB-1 | 2.0% |
| | 3-HH-4 | 8.0% |
| | 3-HH-VFF | 6.0% |
| | 2-HHB-C | 3.0% |
| | 3-HHB-C | 6.0% |
| | 3-HB(F)TB-2 | 8.0% |
| | 3-H2BTB-2 | 5.0% |
| | 3-H2BTB-3 | 5.0% |

Physical properties: $T_{N-I}$=86.9° C.

$\eta$=18.5 mpa·s $\Delta n$=0.147

$\Delta \epsilon$=8.7

$V_{th}$=1.99 V

EXAMPLE 7 (USAGE EXAMPLE 4)

| Composition: | | |
|---|---|---:|
| | 2-HHH-4 (Compound No. 11) | 2.0% |
| | 4-HHH-5 (Compound No. 25) | 2.0% |
| | 2-HHH-3 (Compound No. 10) | 2.0% |
| | 3-HHH-1F (Compound No. 48) | 2.0% |
| | 2O1-BEB(F)-C | 5.0% |
| | 3O1-BEB(F)-C | 15.0% |
| | 4O1-BEB(F)-C | 13.0% |
| | 5O1-BEB(F)-C | 13.0% |
| | 2-HHB(F)-C | 15.0% |
| | 3-HHB(F)-C | 15.0% |
| | 3-HB(F)TB-2 | 4.0% |
| | 3-HB(F)TB-3 | 4.0% |
| | 3-HB(F)TB-4 | 4.0% |
| | 3-HHB-1 | 2.0% |
| | 3-HHB-O1 | 2.0% |

Physical properties: $T_{N-I}$=91.0° C.

$\eta$=87.3 mPa·s $\Delta n$=0.146

$\Delta \epsilon$=31.0

$V_{th}$=0.87 V

EXAMPLE 8 (USAGE EXAMPLE 5)

| Composition: | | |
|---|---|---:|
| | 4-HHH-5 (Compound No. 25) | 3.0% |
| | 3-HHH-1F (Compound No. 48) | 3.0% |
| | 5-PyB-F | 4.0% |
| | 3-PyB(F)-F | 4.0% |
| | 2-BB-C | 5.0% |
| | 4-BB-C | 4.0% |
| | 5-BB-C | 5.0% |
| | 2-PyB-2 | 2.0% |
| | 3-PyB-2 | 2.0% |
| | 4-PyB-2 | 2.0% |
| | 6-PyB-O5 | 3.0% |
| | 6-PyB-O6 | 3.0% |
| | 6-PyB-O7 | 3.0% |
| | 6-PyB-O8 | 3.0% |
| | 3-PyBB-F | 6.0% |
| | 4-PyBB-F | 6.0% |
| | 5-PyBB-F | 6.0% |
| | 3-HHB-3 | 8.0% |
| | 2-H2BTB-2 | 4.0% |
| | 2-H2BTB-3 | 4.0% |
| | 2-H2BTB-4 | 5.0% |
| | 3-H2BTB-2 | 5.0% |
| | 3-H2BTB-3 | 5.0% |
| | 3-H2BTB-4 | 5.0% |

Physical properties: $T_{N-I}$=93.0° C.

$\eta$=34.8 mPa·s $\Delta n$=0.200

$\Delta \epsilon$=6.5

$V_{th}$=2.25 V

EXAMPLE 9 (USAGE EXAMPLE 6)

| Composition: | | |
|---|---|---:|
| | 2-HHH-3 (Compound No. 10) | 3.0% |
| | 3-DB-C | 10.0% |
| | 4-DB-C | 10.0% |
| | 2-BEB-C | 12.0% |
| | 3-BEB-C | 4.0% |
| | 3-PyB(F)-F | 6.0% |
| | 3-HEB-O4 | 8.0% |
| | 4-HEB-O2 | 6.0% |
| | 5-HEB-O1 | 6.0% |
| | 3-HEB-O2 | 5.0% |
| | 5-HEB-O2 | 4.0% |
| | 5-HEB-5 | 5.0% |
| | 4-HEB-5 | 5.0% |
| | 1O-BEB-2 | 4.0% |
| | 3-HHB-1 | 3.0% |
| | 3-HHEBB-C | 3.0% |
| | 3-HBEBB-C | 3.0% |
| | 5-HBEBB-C | 3.0% |

Physical properties: $T_{N-I}$=69.1° C.

$\eta$=39.3 mPa·s $\Delta n$=0.120

$\Delta \epsilon$=11.5

$V_{th}$=1.30 V

EXAMPLE 10 (USAGE EXAMPLE 7)

| Composition: | | |
|---|---|---:|
| | 2-HHH-4 (Compound No. 11) | 1.0% |
| | 1-HHH-3 (Compound No. 2) | 2.0% |
| | 3-HB-C | 18.0% |
| | 5-HB-C | 3.0% |
| | 1O1-HB-C | 10.0% |
| | 3-HB(F)-C | 10.0% |
| | 2-PyB-2 | 2.0% |
| | 3-PyB-2 | 2.0% |
| | 4-PyB-2 | 2.0% |
| | 1O1-HH-3 | 7.0% |
| | 2-BTB-O1 | 7.0% |
| | 3-HHB-1 | 7.0% |
| | 3-HHB-F | 4.0% |
| | 3-HHB-O1 | 4.0% |
| | 3-HHB-3 | 5.0% |
| | 3-H2BTB-2 | 3.0% |
| | 3-H2BTB-3 | 3.0% |
| | 2-PyBH-3 | 4.0% |
| | 3-PyBH-3 | 3.0% |
| | 3-PyBB-2 | 3.0% |

Physical properties:

$T_{N-I}$=79.5° C.

η=17.9 mPa·s

Δn=0.139

Δε=8.1

$V_{th}$=1.76 V

EXAMPLE 11 (USAGE EXAMPLE 8)

| Composition: | | |
|---|---|---|
| 4-HHH-5 (Compound No. 25) | | 3.0% |
| 3-HHH-1F (Compound No. 48) | | 3.0% |
| 2O1-BEB(F)-C | | 5.0% |
| 3O1-BEB(F)-C | | 12.0% |
| 5O1-BEB(F)-C | | 4.0% |
| 1V2-BEB(F,F)-C | | 10.0% |
| 3-HH-EMe | | 10.0% |
| 3-HB-O2 | | 18.0% |
| 3-HHEB-F | | 3.0% |
| 5-HHEB-F | | 3.0% |
| 3-HBEB-F | | 4.0% |
| 2O1-HBEB(F)-C | | 2.0% |
| 3-HB(F)EB(F)-C | | 2.0% |
| 3-HBEB(F,F)-C | | 2.0% |
| 3-HHB-F | | 4.0% |
| 3-HHB-O1 | | 4.0% |
| 3-HHB-3 | | 7.0% |
| 3-HEBEB-F | | 2.0% |
| 3-HEBEB-1 | | 2.0% |

Physical properties: $T_{N-I}$=75.9° C.

η=36.0 mPa·s

Δn=0.113

Δε=23.6

$V_{th}$=0.98 V

EXAMPLE 12 (USAGE EXAMPLE 9)

| Composition: | | |
|---|---|---|
| 2-HHH-4 (Compound No. 11) | | 3.0% |
| 1-HHH-3F (Compound No. 2) | | 2.0% |
| 2O1-BEB(F)-C | | 5.0% |
| 3O1-BEB(F)-C | | 12.0% |
| 5O1-BEB(F)-C | | 4.0% |
| 1V2-BEB(F,F)-C | | 16.0% |
| 3-HB-O2 | | 10.0% |
| 3-HH-4 | | 3.0% |
| 3-HHB-F | | 3.0% |
| 3-HHB-1 | | 3.0% |
| 3-HHB-O1 | | 4.0% |
| 3-HBEB-F | | 4.0% |
| 3-HHEB-F | | 7.0% |
| 5-HHEB-F | | 7.0% |
| 3-H2BTB-2 | | 4.0% |
| 3-H2BTB-3 | | 4.0% |
| 3-H2BTB-4 | | 4.0% |
| 3-HB(F)TB-2 | | 5.0% |

Physical properties: $T_{N-I}$=90.5° C.

η=40.2 mPa·s

Δn=0.141

Δε=28.2

$V_{th}$=1.01 V

EXAMPLE 13 (USAGE EXAMPLE 10)

| Composition: | | |
|---|---|---|
| 32-HHH-1F (Compound No. 48) | | 3.0% |
| 4-HHH-5 (Compound No. 25) | | 2.0% |
| 2-BEB-C | | 12.0% |
| 3-BEB-C | | 4.0% |
| 4-BEB-C | | 6.0% |
| 3-HB-C | | 28.0% |
| 3-HEB-O4 | | 12.0% |
| 4-HEB-O2 | | 8.0% |
| 5-HEB-O1 | | 8.0% |
| 3-HEB-O2 | | 6.0% |
| 5-HHB-O2 | | 5.0% |
| 3-HHB-1 | | 2.0% |
| 3-HHB-O1 | | 4.0% |

Physical properties: $T_{N-I}$=62.5° C.

η=25.8 mPa·s

Δn=0.112

Δε=10.1

$V_{th}$=1.36 V

EXAMPLE 14 (USAGE EXAMPLE 11)

| Composition: | | |
|---|---|---|
| 2-HHH-3 (Compound No. 10) | | 2.0% |
| 1-HHH-3 (Compound No. 2) | | 2.0% |
| 2-BEB-C | | 10.0% |
| 5-BB-C | | 12.0% |
| 7-BB-C | | 7.0% |
| 1-BTB-3 | | 7.0% |
| 2-BTB-1 | | 10.0% |
| 1O-BEB-2 | | 10.0% |
| 1O-BEB-5 | | 12.0% |
| 2-HHB-1 | | 4.0% |
| 3-HHB-F | | 4.0% |
| 3-HHB-1 | | 3.0% |
| 3-HHB-O1 | | 4.0% |
| 3-HHB-3 | | 13.0% |

Physical properties: $T_{N-I}$=66.7° C.

η=20.1 mPa·s

Δn=0.159

Δε=6.5

$V_{th}$=1.79 V

EXAMPLE 15 (USAGE EXAMPLE 12)

| Composition: | | |
|---|---|---|
| 2-HHH-3 (Compound No. 10) | | 2.0% |
| 2-HHH-4 (Compound No. 11) | | 2.0% |
| 2-HHB(F)-F | | 17.0% |
| 3-HHB(F)-F | | 17.0% |
| 5-HHB(F)-F | | 16.0% |
| 2-H2HB(F)-F | | 10.0% |
| 3-H2HB(F)-F | | 5.0% |
| 5-H2HB(F)-F | | 6.0% |
| 2-HBB(F)-F | | 6.0% |
| 3-HBB(F)-F | | 6.0% |
| 5-HBB(F)-F | | 13.0% |

Physical properties: $T_{N-I}$=102.6° C.

η=25.4 mPa·s

Δn=0.093

Δε=4.8

$V_{th}$=2.25 V

P=81.8 μm

EXAMPLE 16 (USAGE EXAMPLE 13)

| Composition: | 3-HHH-1F (Compound No. 48) | 3.0% |
|---|---|---|
| | 2-HHH-3 (Compound No. 10) | 2.0% |
| | 7-HB(F)-F | 5.0% |
| | 5-H2B(F)-F | 5.0% |
| | 3-HB-O2 | 10.0% |
| | 3-HH-4 | 5.0% |
| | 2-HHB(F)-F | 10.0% |
| | 3-HHB(F)-F | 10.0% |
| | 5-HHB(F)-F | 10.0% |
| | 3-H2HB(F)-F | 5.0% |
| | 2-HBB(F)-F | 3.0% |
| | 3-HBB(F)-F | 3.0% |
| | 5-HBB(F)-F | 6.0% |
| | 2-H2BB(F)-F | 5.0% |
| | 3-H2BB(F)-F | 6.0% |
| | 3-HHB-1 | 3.0% |
| | 3-HHB-O1 | 5.0% |
| | 3-HHB-3 | 4.0% |

Physical properties: $T_{N-I}$=88.5° C.

η=18.3 mPa·s

Δn=0.091

Δε=3.3

$V_{th}$=2.66 V

EXAMPLE 17 (USAGE EXAMPLE 14)

| Composition: | 4-HHH-5 (Compound No. 25) | 2.0% |
|---|---|---|
| | 2-HHH-3 (Compound No. 10) | 1.0% |
| | 7-HB(F,F)-F | 3.0% |
| | 3-HB-O2 | 7.0% |
| | 2-HHB(F)-F | 10.0% |
| | 3-HHB(F)-F | 10.0% |
| | 5-HHB(F)-F | 10.0% |
| | 2-HBB(F)-F | 9.0% |
| | 3-HBB(F)-F | 9.0% |
| | 5-HBB(F)-F | 16.0% |
| | 2-HBB-F | 4.0% |
| | 3-HBB-F | 4.0% |
| | 3-HBB(F,F)-F | 5.0% |
| | 5-HBB(F,F)-F | 10.0% |

Physical properties: $T_{N-I}$=86.0° C.

η=24.9 mPa·s

Δn=0.113

Δε=5.6

$V_{th}$=2.03 V

EXAMPLE 18 (USAGE EXAMPLE 15)

| Composition: | 3-HHH-1F (Compound No. 48) | 3.0% |
|---|---|---|
| | 7-HB(F,F)-F | 5.0% |
| | 3-H2HB(F,F)-F | 12.0% |
| | 4-H2HB(F,F)-F | 10.0% |
| | 5-H2HB(F,F)-F | 10.0% |
| | 3-HHB(F,F)-F | 10.0% |
| | 4-HHB(F,F)-F | 5.0% |
| | 3-HH2B(F,F)-F | 15.0% |
| | 5-HH2B(F,F)-F | 6.0% |
| | 3-HBB(F,F)-F | 12.0% |
| | 5-HBB(F,F)-F | 12.0% |

Physical properties: $T_{N-I}$=73.6° C.

η=28.2 mPa·s

Δn=0.084

Δε=8.3

$V_{th}$=1.61 V

EXAMPLE 19 (USAGE EXAMPLE 16)

| Composition: | 2-HHH-3 (Compound No. 10) | 2.0% |
|---|---|---|
| | 3-HHH-1F (Compound No. 48) | 2.0% |
| | 7-HB(F,F)-F | 7.0% |
| | 3-H2HB(F,F)-F | 12.0% |
| | 4-H2HB(F,F)-F | 4.0% |
| | 3-HHB(F,F)-F | 10.0% |
| | 4-HHB(F,F)-F | 5.0% |
| | 3-HBB(F,F)-F | 10.0% |
| | 3-HHEB(F,F)-F | 10.0% |
| | 4-HHEB(F,F)-F | 3.0% |
| | 5-HHEB(F,F)-F | 3.0% |
| | 2-HBEB(F,F)-F | 3.0% |
| | 3-HHEB(F,F)-F | 5.0% |
| | 5-HBEB(F,F)-F | 3.0% |
| | 3-HDB(F,F)-F | 15.0% |
| | 3-HHBB(F,F)-F | 6.0% |

Physical properties: $T_{N-I}$=75.6° C.

η=34.0 mPa·s

Δn=0.084

Δε=12.5

$V_{th}$=1.42 V

EXAMPLE 20 (USAGE EXAMPLE 17)

| Composition: | 2-HHH-4 (Compound No. 11) | 1.0% |
|---|---|---|
| | 4-HHH-5 (Compound No. 25) | 3.0% |
| | 3-HB-CL | 10.0% |
| | 5-HB-CL | 6.0% |
| | 7-HB-CL | 4.0% |
| | 101-HH-5 | 3.0% |
| | 2-HBB(F)-F | 8.0% |
| | 3-HBB(F)-F | 8.0% |
| | 5-HBB(F)-F | 14.0% |
| | 4-HHB-CL | 8.0% |
| | 5-HHB-CL | 4.0% |
| | 3-H2HB(F)-CL | 4.0% |
| | 3-HBB(F,F)-F | 10.0% |
| | 5-H2BB(F,F)-F | 9.0% |
| | 3-HB(F)VB-2 | 4.0% |
| | 3-HB(F)VB-3 | 4.0% |

Physical properties: $T_{N-I}$=92.4° C.

η=21.3 mPa·s

Δn=0.128

Δε=4.7

$V_{th}$=2.33 V

EXAMPLE 21 (USAGE EXAMPLE 18)

| Composition: | | |
|---|---|---|
| 1-HHH-3 (Compound No. 2) | | 2.0% |
| 2-HHH-3 (Compound No. 10) | | 2.0% |
| 3-HHB(F,F)-F | | 9.0% |
| 3-H2HB(F,F)-F | | 8.0% |
| 4-H2HB(F,F)-F | | 8.0% |
| 5-H2HB(F,F)-F | | 8.0% |
| 3-HBB(F,F)-F | | 21.0% |
| 5-HBB(F,F)-F | | 20.0% |
| 3-H2BB(F,F)-F | | 10.0% |
| 5-HHBB(F,F)-F | | 3.0% |
| 3-HH2BB(F,F)-F | | 3.0% |
| 5-HHEBB-F | | 2.0% |
| 101-HBBH-5 | | 4.0% |

Physical properties: $T_{N-I}$=94.8° C.

$\eta$=33.9 mPa·s $\Delta n$=0.113

$\Delta\epsilon$=8.9

$V_{th}$=1.75 V

EXAMPLE 22 (USAGE EXAMPLE 19)

| Composition: | | |
|---|---|---|
| 2-HHH-3 (Compound No. 10) | | 2.0% |
| 2-HHH-4 (Compound No. 11) | | 1.0% |
| 5-HB-F | | 12.0% |
| 6-HB-F | | 10.0% |
| 7-HB-F | | 7.0% |
| 2-HHB-OCF3 | | 7.0% |
| 3-HHB-OCF3 | | 11.0% |
| 4-HHB-OCF3 | | 7.0% |
| 5-HHB-OCF3 | | 5.0% |
| 3-HH2B-OCF3 | | 4.0% |
| 3-HHB(F,F)-OCF3 | | 5.0% |
| 3-HBB(F)-F | | 10.0% |
| 5-HBB(F)-F | | 10.0% |
| 3-HH2B(F)-F | | 3.0% |
| 3-HB(F)BH-3 | | 3.0% |
| 5-HBBH-3 | | 3.0% |

Physical properties: $T_{N-I}$=86.4° C.

$\eta$=15.3 mPa·s $\Delta n$=0.091

$\Delta\epsilon$=4.4

$V_{th}$=2.42 V

EXAMPLE 23 (USAGE EXAMPLE 20)

| Composition: | | |
|---|---|---|
| 4-HHH-5 (Compound No. 25) | | 2.0% |
| 3-HHH-1F (Compound No. 48) | | 1.0% |
| 5-H4HB(F,F)-F | | 7.0% |
| 5-H4HB-CCF3 | | 15.0% |
| 3-H4HB(F,F)-CF3 | | 8.0% |
| 5-H4HB(F,F)-CF3 | | 10.0% |
| 3-HB-CL | | 6.0% |
| 5-HB-CL | | 5.0% |
| 2-H2BB(F)-F | | 5.0% |
| 3-H2BB(F)-F | | 10.0% |
| 5-HVHB(F,F)-F | | 5.0% |
| 3-HHB-OCF3 | | 3.0% |
| 3-H2HB-OCF3 | | 3.0% |
| V-HHB(F)-F | | 5.0% |
| 3-HChB(F)-F | | 5.0% |
| 5-HHEB-OCF3 | | 2.0% |

-continued

| | |
|---|---|
| 3-HBEB(F,F)-F | 5.0% |
| 5-HH-V2F | 3.0% |

Physical properties: $T_{N-I}$=70.9° C.

$\eta$=24.8 mPa·s $\Delta n$=0.089

$\Delta\epsilon$=8.0

$V_{th}$=1.78 V

EXAMPLE 24 (USAGE EXAMPLE 21)

| Composition: | | |
|---|---|---|
| 2-HHH-3 (Compound No. 10) | | 3.0% |
| 2-HHB(F)-F | | 2.0% |
| 3-HHB(F)-F | | 2.0% |
| 5-HHB(F)-F | | 2.0% |
| 2-HBB(F)-F | | 6.0% |
| 3-HBB(F)-F | | 6.0% |
| 5-HBB(F)-F | | 10.0% |
| 2-H2BB(F)-F | | 9.0% |
| 3-H2BB(F)-F | | 9.0% |
| 3-HBB(F,F)-F | | 25.0% |
| 5-HBB(F,F)-F | | 19.0% |
| 101-HBBH-4 | | 4.0% |
| 101-HBBH-5 | | 3.0% |

Physical properties: $T_{N-I}$=94.1° C.

$\eta$=35.0 mPa·s $\Delta n$=0.133

$\Delta\epsilon$=7.2

$V_{th}$=1.93 V

As described above, the compound represented by general formula (1) of the present invention has the following excellent properties:

(1) It has a low viscosity;

(2) It has a wide temperature range within which it assumes a liquid crystal phase, particularly a high clearing point, or causes no reduction of the nematic phase temperature range when incorporated in a liquid crystal composition;

(3) It is stable to external factors such as heat and light;

(4) It has a good solubility with other liquid-crystalline compounds; and (5) It has an appropriate refractive index anisotropy.

The use of the compound represented by general formula (1) of the present invention having such excellent properties makes it possible to obtain a liquid crystal composition having excellent properties.

While the invention has been described in detail and with reference to specific examples thereof, it will be apparent to one skilled in the art that various changes and modifications can be made therein without departing from the spirit and scope thereof.

What is claimed is:

1. A liquid-crystalline compound, represented by the following general formula (1):

(1)

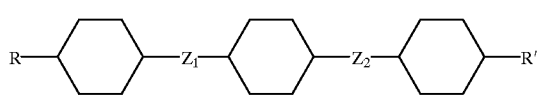

wherein R and R' each independently represents a $C_{1-20}$ alkyl or halogenated $C_{1-20}$ alkyl group or a group obtained by replacing one or more —$CH_2$— groups in the alkyl or halogenated alkyl group by any of —O—, —S—, —CH=CH— or —C≡C—, provided that two or more —$CH_2$— groups are not consecutively replaced by either —O— or —S—; at least one of R and R' being a halogenated alkyl group other than a $CF_3$-terminated alkyl group; and $Z_1$ and $Z_2$ each independently represents a covalent bond or 1,2-ethylene group.

2. The liquid-crystalline compound according to claim 1, which is selected from the group consisting of compounds represented by formulae (1-1-2), (1-1-3), (1-2-2), (1-2-3), (1-3-2), (1-3-3), (1-4-2) and (1-4-3):

(1-1-2)

(1-1-3)

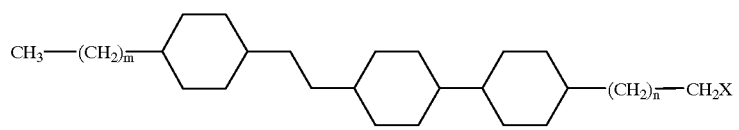
(1-2-2)

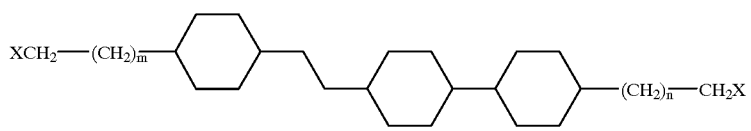
(1-2-3)

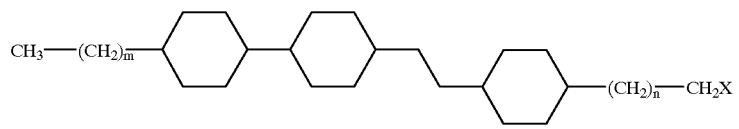
(1-3-2)

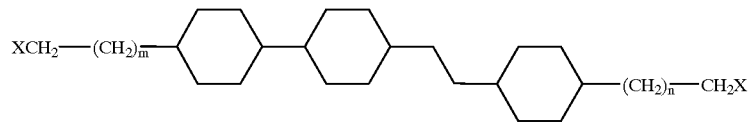
(1-3-3)

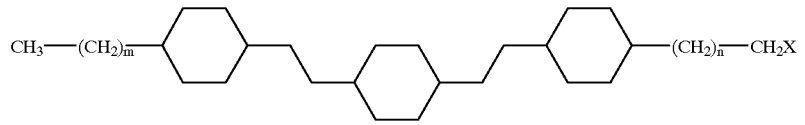
(1-4-2)

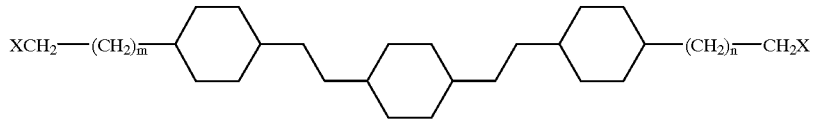
(1-4-3)

wherein X represents a fluorine or chlorine atom, and m and n each independently represents an integer of from 0 to 19.

3. The liquid-crystalline compound according to claim 2, which is selected from the group consisting of compounds of formulae (1-1-2), (1-2-2), (1-3-2) and (1-4-2) wherein X is a fluorine atom.

4. The liquid-crystalline compound according to claim 2, which is selected from the group consisting of compounds of formulae (1-1-3), (1-2-3), (1-3-3) and (1-4-3) wherein X is a fluorine atom.

5. The liquid-crystalline compound according to claim 2, which is represented by formula (1-1-2) wherein n is O and X is a fluorine atom.

6. The liquid-crystalline compound according to claim 1, wherein both R and R' are a halogenated alkyl group.

7. A liquid crystal composition comprising at least two compounds, at least one of which is a liquid-crystalline compound represented by the following general formula (1):

(1)

wherein R and R' each independently represents a $C_{1-20}$ alkyl or halogenated $C_{1-20}$ alkyl group or a group obtained by replacing one or more —$CH_2$— groups in the alkyl or halogenated alkyl group by any of —O—, —S—, —CH=CH— or —C≡C—, provided that two or more —$CH_2$— groups are not consecutively replaced by either —O— or —S—; at least one of R and R' being a halogenated alkyl group other than a $CF_3$-terminated alkyl group; and $Z_1$ and $Z_2$ each independently represents a covalent bond or 1,2-ethylene group.

8. The liquid crystal composition according to claim 7, wherein both R and R' of the liquid-crystalline compound are a halogenated alkyl group.

9. A liquid crystal display element comprising the liquid crystal composition as claimed in claim 6.

10. The liquid crystal composition according to claim 7, wherein the at least one liquid-crystalline compound is selected from the group consisting of compounds represented by formulae (1-1-2), (1-1-3), (1-2-2), (1-2-3), (1-3-2), (1-3-3), (1-4-2) and (1-4-3):

(1-1-2)

(1-1-3)

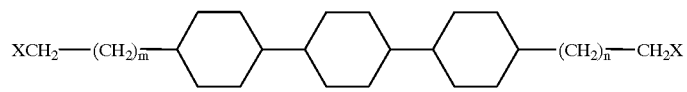

(1-2-2)

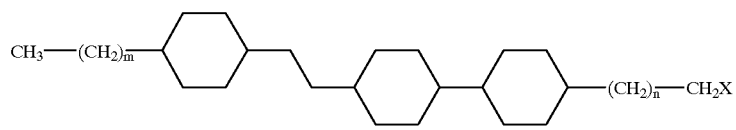

(1-2-3)

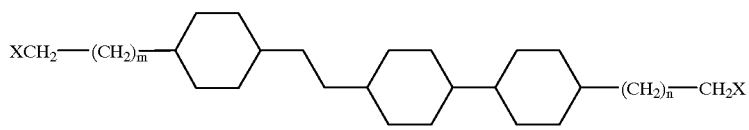

(1-3-2)

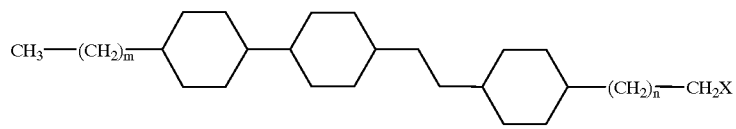

(1-3-3)

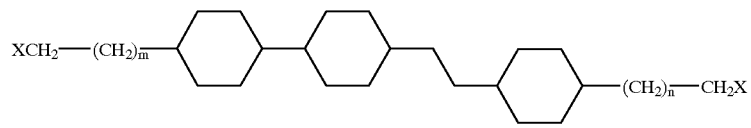

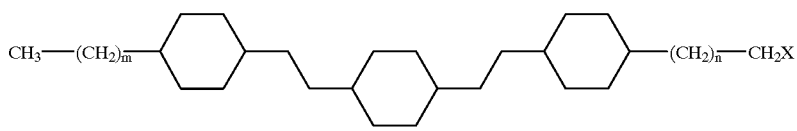

(1-4-2)

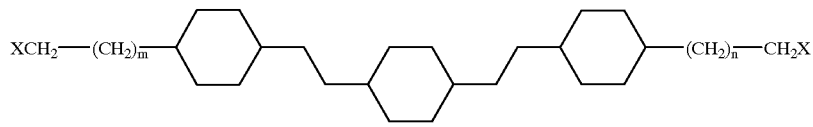

(1-4-3)

wherein X represents a fluorine or chlorine atom, and m and n each independently represents an integer of from 0 to 19.

11. The liquid crystal composition according to claim 7, wherein the at least one liquid-crystalline compound is selected from the group consisting of compounds of formulae (1-1-2), (1-2-3), (1-3-2) and (1-4-2) wherein X is a fluorine atom.

12. The liquid crystal composition according to claim 7, wherein the at least one liquid-crystalline compound is selected from the group consisting of compounds of formulae (1-1-3), (1-2-3), (1-3-3) and (1-4-3) wherein X is a fluorine atom.

13. The liquid crystal composition according to claim 7, wherein the at least one liquid-crystalline compound is represented by formula (1-1-2) wherein n is 0 and X is a fluorine atom.

14. A liquid crystal composition comprising at least one liquid-crystalline compound represented by the following general formula (1):

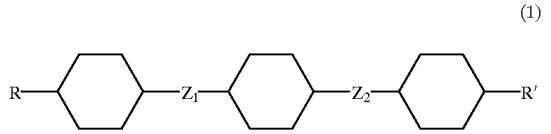

(1)

wherein R and R' each independently represents a $C_{1-20}$ alkyl or halogenated $C_{1-20}$ alkyl group or a group obtained by replacing one or more —$CH_2$— groups in the alkyl or halogenated alkyl group by any of —O—, —S—, —CH=CH— or —C≡C—, provided that two or more —$CH_2$— groups are not consecutively replaced by either —O— or —S—; at least one of R and R' being a halogenated alkyl group other than a $CF_3$-terminated alkyl group; and $Z_1$ and $Z_2$ each independently represents a covalent bond or 1,2-ethylene group; and at least one compound selected from the group consisting of compounds represented by the following general formulae (2), (3) and (4):

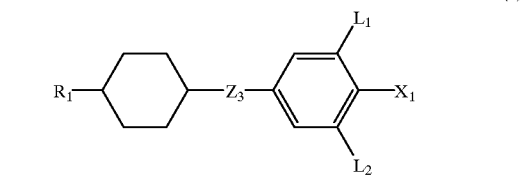

(2)

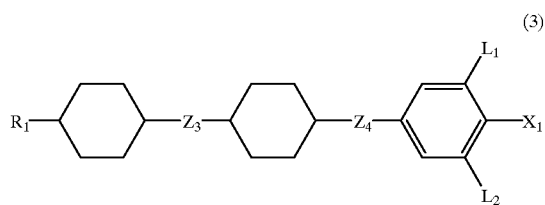

(3)

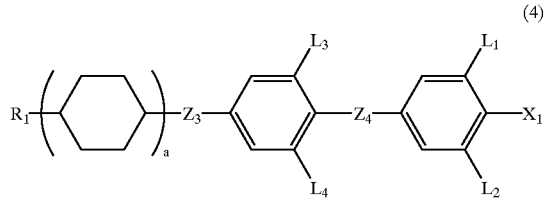

(4)

wherein $R_1$ represents a $C_{1-10}$ alkyl group; $X_1$ represents —F, —Cl, —$OCF_3$, —$OCF_2H$, —$CF_3$, —$CF_2H$ or —$CFH_2$; $L_1$, $L_2$, $L_3$ and $L_4$ each independently represents —H or —F; $Z_3$ and $Z_4$ each independently represents —$(CH_2)_2$—, —CH=CH— or a covalent bond; and a represents an integer of from 1 or 2.

15. A liquid crystal composition according to claim 14, further comprising at least one compound selected from the group consisting of compounds represented by the following general formulae (5), (6), (7), (8) and (9):

(5)

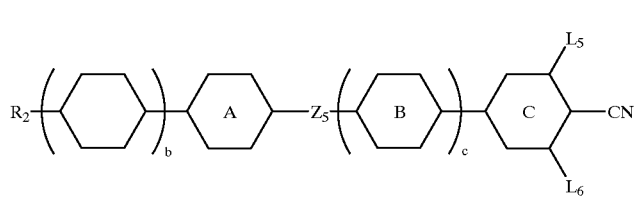

wherein $R_2$ represents —F, a $C_{1-10}$ alkyl group, a $C_{2-10}$ alkenyl group or a group obtained by replacing one or more methylene groups (—CH$_2$—) in the alkyl or alkenyl group by an oxygen atom (—O—), provided that two or more methylene groups are not consecutively replaced by an oxygen atom; the ring A represents trans-1,4-cyclohexylene group, 1,4-phenylene group or 1,3-dioxane-2,5-diyl group; the ring B represents trans-1,4-cyclohexylene group, 1,4-phenylene group or pyrimidine-2,5-diyl group; the ring C represents trans-1,4-cyclohexylene group or 1,4-phenylene group; $Z_5$ represents —(CH$_2$)$_2$—, —COO— or a covalent bond; $L_5$ and $L_6$ each independently represents —H or —F; and b and c each independently represents an integer of 0 or 1;

(6)

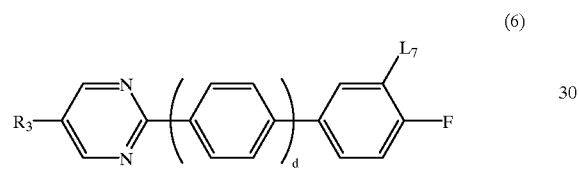

wherein $R_3$ represents a $C_{1-10}$ alkyl group; $L_7$ represents —H or —F; and d represents an integer of 0 or 1;

(7)

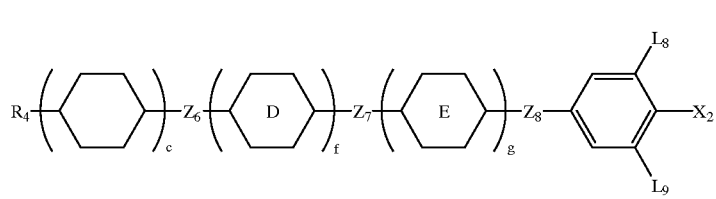

wherein $R_4$ represents a $C_{1-10}$ alkyl group; the rings D and E each independently represents trans-1,4-cyclohexylene group or 1,4-phenylene group; $Z_6$ and $Z_7$ each independently represents —COO— or a covalent bond; $Z_8$ represents —COO— or —C≡C—; $L_8$ and $L_9$ each independently represents —H or —F; $X_2$ represents —F, —OCF$_3$, —OCF$_2$H, —CF$_3$, —CF$_2$H or —CFH$_2$, provided that when $X_2$ represents —OCF$_3$, —OCF$_2$H, —CF$_3$, —CF$_2$H or —CFH$_2$, both $L_8$ and $L_9$ represent H; and e, f and g each independently represents an integer of 0 or 1;

(8)

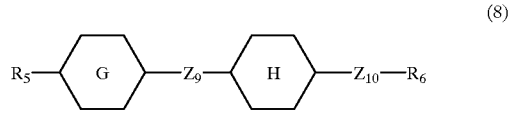

wherein $R_5$ and $R_6$ each independently represents a $C_{1-10}$ alkyl group, a $C_{2-10}$ alkenyl group or a group obtained by replacing one or more methylene groups (—CH$_2$—) in the alkyl or alkenyl group by an oxygen atom (—O—), provided that two or more methylene groups are not consecutively replaced by an oxygen atom; the ring G represents trans-1,4-cyclohexylene group, 1,4-phenylene group or pyrimidine-2,5-diyl group; the ring H represents trans-1,4-cyclohexylene group or 1,4-phenylene group; $Z_9$ represents —C≡C—, —COO—, —(CH$_2$)$_2$—, —CH=CH—C≡C— or a covalent bond; and $Z_{10}$ represents —COO— or a covalent bond; and (9)

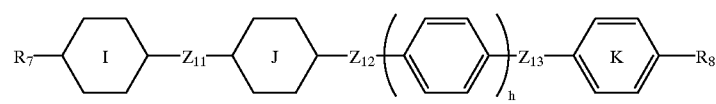

wherein $R_7$ and $R_8$ each independently represents a $C_{1-10}$ alkyl group, a $C_{2-10}$ alkenyl group or a group obtained by replacing one or more methylene groups (—CH$_2$—) in the alkenyl group by an oxygen atom (—O—), provided that two or more methylene groups are not consecutively replaced by an oxygen atom; the ring I represents trans-1,4-cyclohexylene group, 1,4-phenylene group or pyrimidine-2,5-diyl group; the ring J represents trans-1,4-cyclohexylene group, or 1,4-phenylene group or pyrimidine-2,5-diyl group one or more hydrogen atoms on which ring may be substituted by a fluorine atom; the ring K represents trans-1,4-cyclohexylene group or 1,4-phenylene group; $Z_{11}$ and $Z_{13}$ each independently represents —COO—, —(CH$_2$)$_2$— or a covalent bond; $Z_{12}$ represents —CH=CH—, —C≡C—, —COO— or a covalent bond; and h represents an integer of 0 or 1.

16. A liquid crystal display element comprising the liquid crystal composition as claimed in claim 14.

17. A liquid crystal display element comprising the liquid crystal composition as claimed in claim 15.

18. A liquid crystal composition comprising at least one liquid-crystalline compound represented by the following general formula (1):

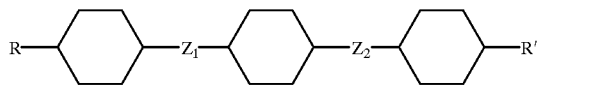
(1)

wherein R and R' each independently represents a $C_{1-20}$ alkyl or halogenated $C_{1-20}$ alkyl group or a group obtained by replacing one or more —CH$_2$— groups in the alkyl or halogenated alkyl group by any of —O—, —S—, —CH=CH— or —C≡C—, provided that two or more —CH$_2$— groups are not consecutively replaced by either —O— or —S—; at least one of R and R' being a halogenated alkyl group other than a CF$_3$-terminated alkyl group; and $Z_1$ and $Z_2$ each independently represents a covalent bond or 1,2-ethylene group; and at least one compound selected from the group consisting of compounds represented by the following general formulae (5), (6), (7), (8) and, (9):

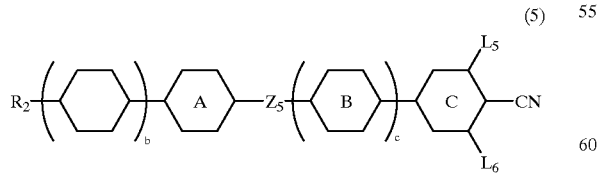
(5)

wherein $R_2$ represents —F, a $C_{1-10}$ alkyl group, a $C_{2-10}$ alkenyl group or a group obtained by replacing one or more methylene groups (—CH$_2$—) in the alkyl or alkenyl group by an oxygen atom (—O—), provided that two or more methylene groups are not consecutively replaced by an oxygen atom; the ring A represents trans-1,4-cyclohexylene group, 1,4-phenylene group or 1,3-dioxane-2,5-diyl group; the ring B represents trans-1,4-cyclohexylene group, 1,4-phenylene group or pyrimidine-2,5-diyl group; the ring C represents trans-1,4-cyclohexylene group or 1,4-phenylene group; $Z_5$ represents —(CH$_2$)$_2$—, —COO— or a covalent bond; $L_5$ and $L_6$ each independently represents —H or —F; and b and c each independently represents an integer of 0 or 1;

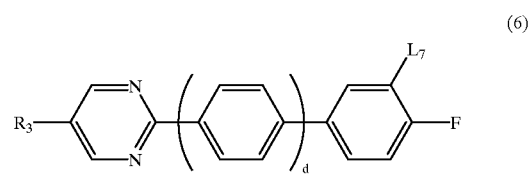
(6)

wherein $R_3$ represents a $C_{1-10}$ alkyl group; $L_7$ represents —H or —F; and d represents an integer of 0 or 1;

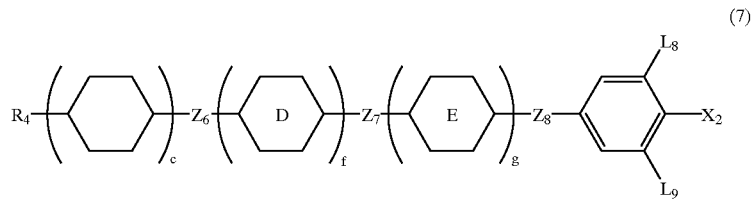
(7)

wherein $R_4$ represents a $C_{1-10}$ alkyl group; the rings D and E each independently represents trans-1,4-cyclohexylene group or 1,4-phenylene group; $Z_6$ and $Z_7$ each independently represents —COO— or a covalent bond; $Z_8$ represents —COO— or —C≡C—; $L_8$ and $L_9$ each independently represents —H or —F; $X_2$ represents —F, —OCF$_3$, —OCF$_2$H, —CF$_3$, —CF$_2$H or —CFH$_2$, provided that when $X_2$ represents —OCF$_3$, —OCF$_2$H, —CF$_3$, —CF$_2$H or —CFH$_2$, both $L_8$ and $L_9$ represent H; and e, f and g each independently represents an integer of 0 or 1;

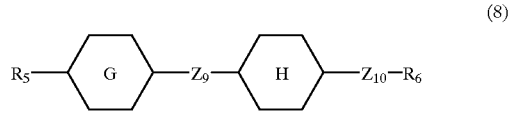
(8)

wherein $R_5$ and $R_6$ each independently represents a $C_{1-10}$ alkyl group, a $C_{2-10}$ alkenyl group or a group obtained by replacing one or more methylene groups (—CH$_2$—) in the alkyl or alkenyl group by an oxygen atom (—O—), provided that two or more methylene groups are not consecutively replaced by an oxygen atom; the ring G represents trans-1,4-cyclohelxylene group, 1,4-phenylene group or pyrimidine-2,5-diyl group; the ring H represents trans-1,4-cyclohexylene group or 1,4-phenylene group; $Z_9$ represents —C≡C—, —COO—, —(CH$_2$)$_2$—, —CH=CH—C≡C— or a covalent bond; and $Z_{10}$ represents —COO— or a covalent bond; and

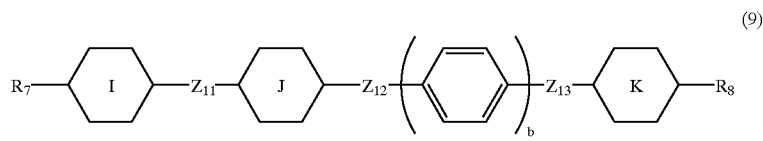

(9)

wherein $R_7$ and $R_8$ each independently represents a $C_{1-10}$ alkyl group, a $C_{2-10}$ alkenyl group or a group obtained by replacing one or more methylene groups (—$CH_2$—) in the alkenyl group by an oxygen atom (—O—), provided that two or more methylene groups are not consecutively replaced by an oxygen atom; the ring I represents trans-1, 4-cyclohexylene group, 1,4-phenylene group or pyrimidine-2,5-diyl group; the ring J represents trans-1,4-cyclohexylene group, or 1,4-phenylene group or pyrimidine-2,5-diyl group one or more hydrogen atoms on which ring may be substituted by a fluorine atom; the ring K represents trans-1, 4-cyclohexylene group or 1,4-phenylene group; $Z_{11}$ and $Z_{13}$ each independently represents —COO—, —$(CH_2)_2$— or a covalent bond; $Z_{12}$ represents —CH=CH—, —C≡C—, —COO— or a covalent bond; and h represents an integer of 0 or 1.

19. A liquid crystal display element comprising the liquid crystal composition as claimed in claim 18.

* * * * *